(12) United States Patent
Aharoni et al.

(10) Patent No.: US 10,100,322 B2
(45) Date of Patent: Oct. 16, 2018

(54) PLANT WITH ALTERED CONTENT OF STEROIDAL GLYCOALKALOIDS

(71) Applicant: YEDA RESEARCH AND DEVELOPMENT CO. LTD., Rehovot (IL)

(72) Inventors: Asaph Aharoni, Tel Aviv (IL); Maxim Itkin, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 16 days.

(21) Appl. No.: 14/895,059

(22) PCT Filed: Jun. 2, 2014

(86) PCT No.: PCT/IL2014/050497
§ 371 (c)(1),
(2) Date: Dec. 1, 2015

(87) PCT Pub. No.: WO2014/195944
PCT Pub. Date: Dec. 11, 2014

(65) Prior Publication Data
US 2016/0122775 A1    May 5, 2016

Related U.S. Application Data

(60) Provisional application No. 61/831,164, filed on Jun. 5, 2013.

(51) Int. Cl.
*C12N 15/82* (2006.01)
(52) U.S. Cl.
CPC ..... *C12N 15/8218* (2013.01); *C12N 15/8243* (2013.01); *C12N 15/8247* (2013.01)
(58) Field of Classification Search
None
See application file for complete search history.

(56) References Cited

U.S. PATENT DOCUMENTS

| | | | |
|---|---|---|---|
| 4,987,071 A | 1/1991 | Cech et al. | |
| 5,959,180 A | 9/1999 | Moehs et al. | |
| 6,326,174 B1 | 12/2001 | Joyce et al. | |
| 7,375,259 B1 | 5/2008 | Mccue et al. | |
| 7,439,419 B1 | 10/2008 | Mccue et al. | |
| 2005/0108791 A1* | 5/2005 | Edgerton | C07K 14/415 800/284 |
| 2011/0265221 A1 | 10/2011 | Abad et al. | |
| 2012/0159676 A1 | 6/2012 | Umemoto et al. | |
| 2013/0167271 A1 | 6/2013 | Umemoto et al. | |

FOREIGN PATENT DOCUMENTS

| | | |
|---|---|---|
| WO | WO 2000/066716 | 11/2000 |
| WO | WO 2011/061656 A1 | 4/2011 |
| WO | WO 2012/095843 A1 | 7/2012 |

OTHER PUBLICATIONS

Arnqvist et al. "Reduction of cholesterol and glycoalkaloid levels in transgenic potato plants by overexpression of a type 1 sterol methyltransferase cDNA." Plant Physiology 131.4 (2003): 1792-1799.
Belhaj "Plant genome editing made easy: targeted mutagenesis in model and crop plants using the CRISPR/Cas system. Plant methods" Oct. 11, 2013;9(1):1.
Cardenas et al. "GAME9 regulates the biosynthesis of steroidal alkaloids and upstream isoprenoids in the plant mevalonate pathway." Nature communications 7 (2016).
Casamitjana-Martinez et al. "Root-specific CLE19 overexpression and the sol1/2 suppressors implicate a CLV-like pathway in the control of *Arabidopsis* root meristem maintenance." Current Biology 13.16 (2003): 1435-1441.
Database NCBI "PREDICTED: ethylene-responsive transcription factor 1-like [*Solanum lycopersicum*]" GeneBank accession No. XP_004229751. URL: http:www.ncbi.nlm.nih.gov/protein/460367786?report=genbank&log$=prottop&blast_rank=2&RID=ZUTPRBJX01R. originally accessed Mar. 12, 201.
Database NCBI "PREDICTED: transcription factor BIM2-like [*Solanum lycopersicum*]" GeneBank accession No. XP_004234703.1. URL: http:www.ncbi.nlm.nih.gov/protein/460377857?report=genbank&log$=prottop&blast_rank=1&RID=TE9A3KF01R. originally accessed Mar. 12, 2013.
De Carolis et al. "2-Oxoglutarate-dependent dioxygenase and related enzymes: biochemical characterization." Phytochemistry 36.5 (1994): 1093-1107.
Dinesh-Kumar et al. "Virus-induced gene silencing. Plant Functional Genomics". 2003:287-93.
Eckert et al. "DNA polymerase fidelity and the polymerase chain reaction" Genome Research. Aug. 1, 1991;1(1):17-24.
Eich, Eckart. "Solanaceae and Convolvulaceae: Secondary metabolites: Biosynthesis, chemotaxonomy, biological and economic significance" (a handbook). Springer Science & Business Media, 2008.
Estornell et al. "A multisite gateway-based toolkit for targeted gene expression and hairpin RNA silencing in tomato fruits." Plant biotechnology journal 7.3 (2009): 298-309.
Expósito-Rodríguez et al. "Selection of internal control genes for quantitative real-time RT-PCR studies during tomato development process". BMC plant biology. Dec. 22, 2008;8(1):1.
Fernandez et al. "Flexible tools for gene expression and silencing in tomato." Plant Physiology 151.4 (2009): 1729-1740.
Fire et al. "Potent and specific genetic interference by double-stranded RNA in Caenorhabditis elegans." nature 391.6669 (1998): 806-811.

(Continued)

*Primary Examiner* — Brent T Page
(74) *Attorney, Agent, or Firm* — Mark S. Cohen; Pearl Cohen Zedek Latzer Baratz LLP

(57) ABSTRACT

The present invention relates to genetically modified plants by key genes involved in the biosynthesis of steroidal alkaloids. These plants have altered content of steroidal (glyco)alkaloids. Solanaceous crop plants with reduced content of antinutritional steroidal glycoalkaloids are provided.

32 Claims, 21 Drawing Sheets
Specification includes a Sequence Listing.

(56) References Cited

OTHER PUBLICATIONS

Guo et al. "par-1, a gene required for establishing polarity in C. elegans embryos, encodes a putative Ser/Thr kinase that is asymmetrically distributed" Cell. May 19, 1995;81(4):611-20.

Heim et al. "The basic helix-loop-helix transcription factor family in plants: a genome-wide study of protein structure and functional diversity." Molecular biology and evolution 20.5 (2003): 735-747.

Higuchi R. ch. 22 "Recombinant pcr" in PCR protocols: a guide to methods and applications. 1990;177-183.

Ingelbrecht et al. "Different 3'end regions strongly influence the level of gene expression in plant cells." The Plant Cell 1.7 (1989): 671-680.

Itkin et al. "Biosynthesis of antinutritional alkaloids in solanaceous crops is mediated by clustered genes." Science 341.6142 (2013): 175-179.

Itkin et al. "GLYCOALKALOID METABOLISM1 is required for steroidal alkaloid glycosylation and prevention of phytotoxicity in tomato." The Plant Cell 23.12 (2011): 4507-4525.

Kai et al. "Scopoletin is biosynthesized via ortho-hydroxylation of feruloyl CoA by a 2-oxoglutarate-dependent dioxygenase in *Arabidopsis thaliana*." The Plant Journal 55.6 (2008): 989-999.

Kundu, Siddhartha "Distribution and prediction of catalytic domains in 2-oxoglutarate dependent dioxygenases." BMC research notes 5.1 (2012): 1.

Li et al. "ESI-QqTOF-MS/MS and APCI-IT-MS/MS analysis of steroid saponins from the rhizomes of Dioscorea panthaica". Journal of Mass Spectrometry. Jan. 1, 2006;41(1):1-22.

Lin et al. "Putative genes involved in saikosaponin biosynthesis in *Bupleurum* species." International journal of molecular sciences 14.6 (2013): 12806-12826.

McCue et al. "Metabolic compensation of steroidal glycoalkaloid biosynthesis in transgenic potato tubers: using reverse genetics to confirm the in vivo enzyme function of a steroidal alkaloid galactosyltransferase." Plant Science 168.1 (2005): 267-273.

McKibbin et al. "Production of high-starch, low-glucose potatoes through over expression of the metabolic regulator SnRK1." Plant biotechnology journal 4.4 (2006): 409-418.

Orzaez e al. "A visual reporter system for virus-induced gene silencing in tomato fruit based on anthocyanin accumulation". Plant physiology. Jul. 1, 2009;150(3):1122-34.

Robinson et al. "Integrative genomics viewer" Nature biotechnology. Jan. 1, 2011;29(1):24-6.

Rocha-Sosa et al. "Both developmental and metabolic signals activate the promoter of a class I patatin gene". The EMBO journal. Jan. 1989;8(1):23.

Roddick, James G. "The acetylcholinesterase-inhibitory activity of steroidal glycoalkaloids and their aglycones." Phytochemistry 28.10 (1989): 2631-2634.

Shannon et al. "Cytoscape: a software environment for integrated models of biomolecular interaction networks." Genome research 13.11 (2003): 2498-2504.

Supplementary European Search Report for European Application No. 14808414.8 dated Oct. 10, 2016.

Trapnell et al. "Differential gene and transcript expression analysis of RNA-seq experiments with TopHat and Cufflinks." Nature protocols 7.3 (2012): 562-578.

Wu Ed., 1993 Meth. In Enzymol. vol. 217, San Diego: Academic Press.

Yang et al. "Isolation and functional analysis of a strong specific promoter in photosynthetic tissues." Science in China Series C: Life Sciences 46.6 (2003): 651-660.

\* cited by examiner

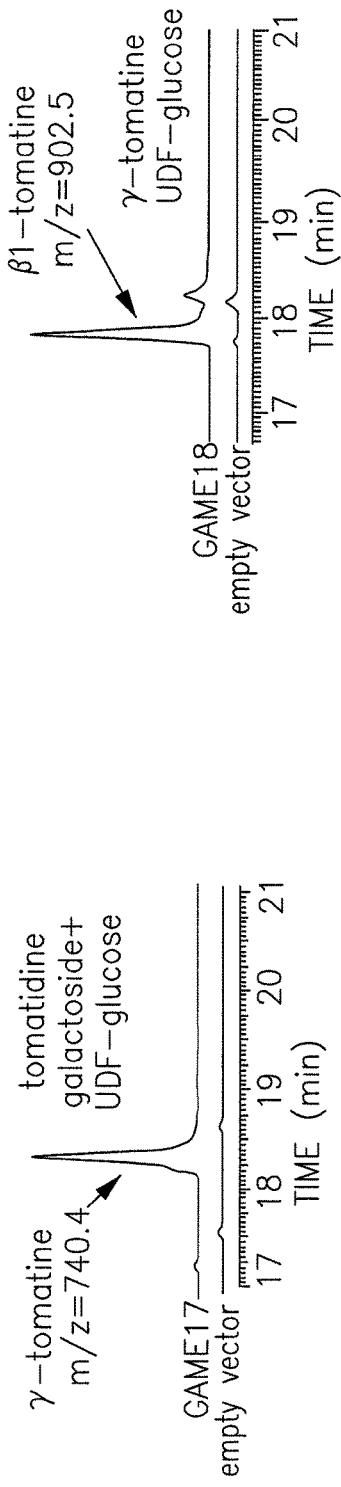
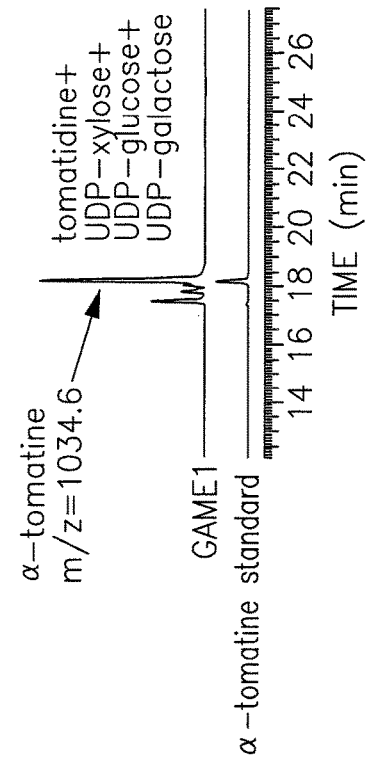
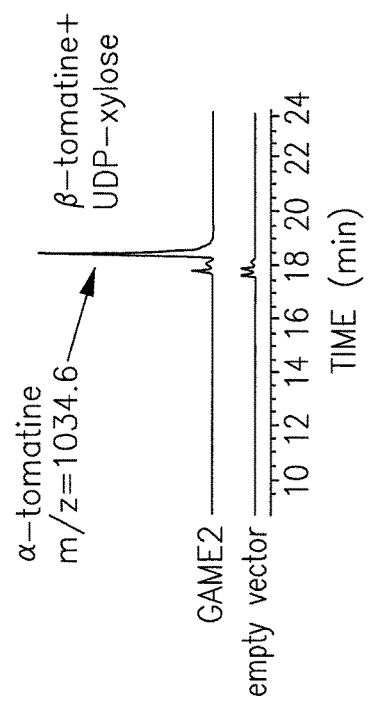

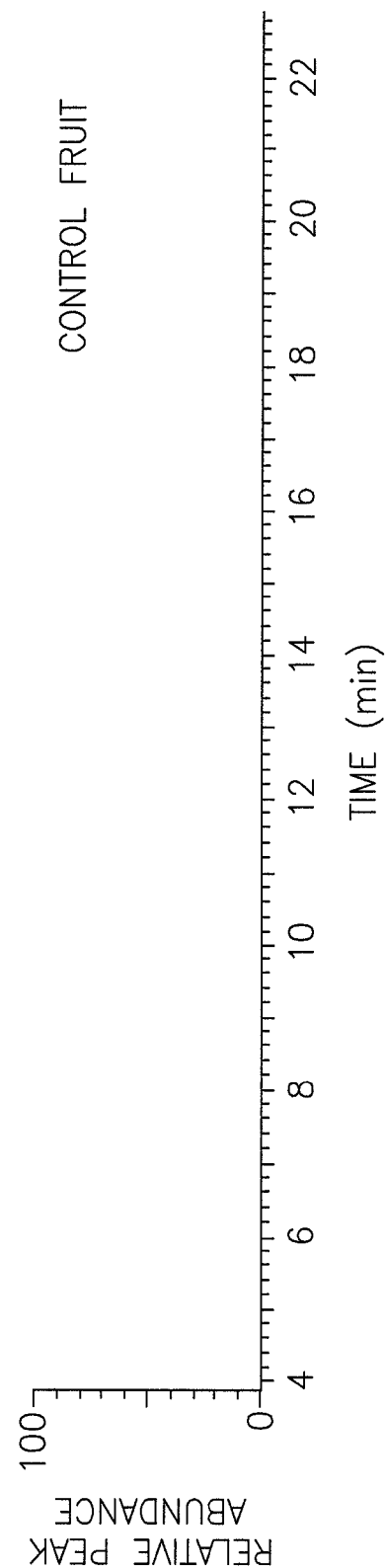

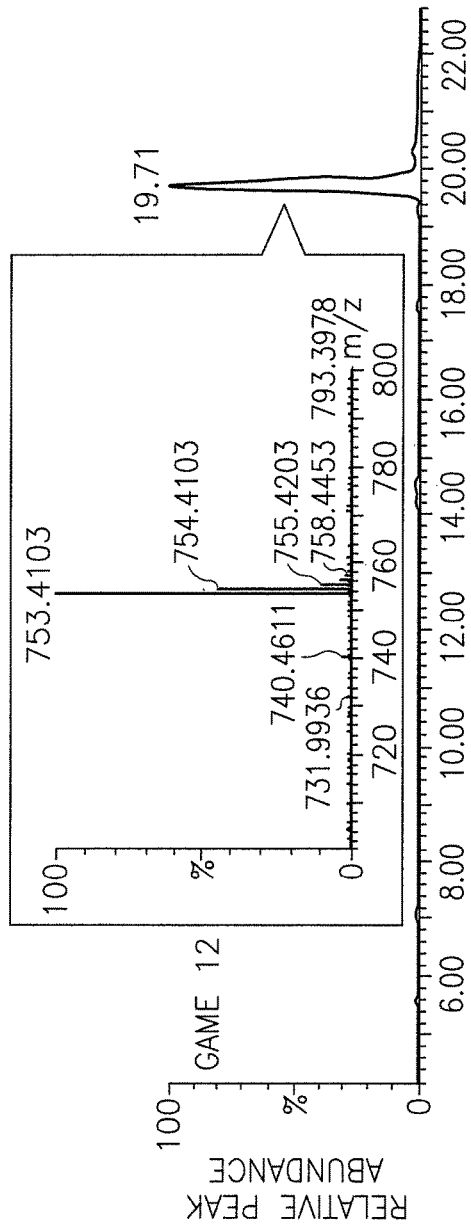
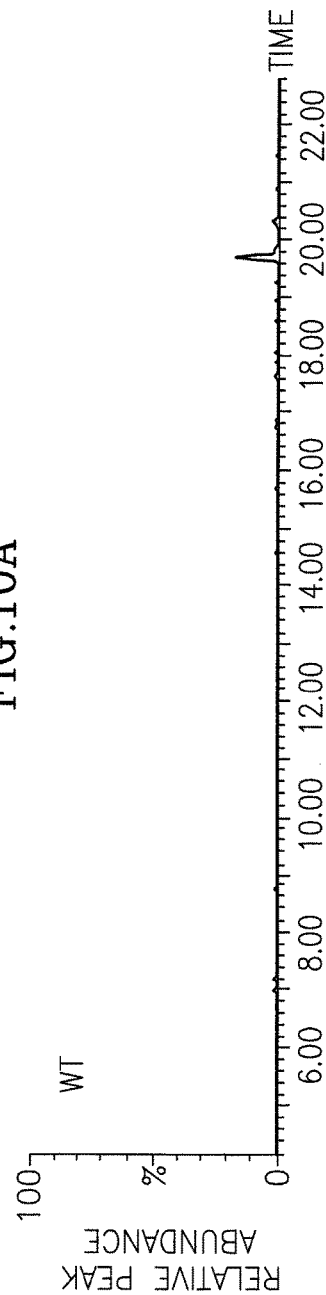
FIG.10A
FIG.10B

PLANT WITH ALTERED CONTENT OF STEROIDAL GLYCOALKALOIDS

CROSS-REFERENCE TO RELATED APPLICATIONS

This application is a National Phase Application of PCT International Application No. PCT/IL2014/050497, International Filing Date Jun. 2, 2014, claiming priority of U.S. Provisional Patent Application No. 61/831,164, filed Jun. 5, 2013 which are hereby incorporated by reference.

FIELD OF THE INVENTION

The present invention relates to key genes in the biosynthesis of steroidal alkaloids and to genetically modified plants with altered content of steroidal alkaloids, particularly to Solanaceous crop plants with reduced content of antinutritional steroidal glycoalkaloids

BACKGROUND OF THE INVENTION

The plant kingdom produces hundreds of thousands of different small compounds that are often genus or family specific. These molecules, referred to as secondary metabolites, are not vital to cells that produce them, but contribute to the overall fitness of the organisms. Alkaloids are one example of secondary metabolites. They are low molecular weight nitrogen-containing organic compounds, typically with a heterocyclic structure. Alkaloid biosynthesis in plants is tightly controlled during development and in response to stress and pathogens.

The broad group of triterpenoid-alkaloid compounds is widespread in plants and derived from the cytosolic Mevalonic acid isoprenoid biosynthetic pathway. Steroidal saponins and Steroidal alkaloids are two large classes of triterpenoids produced by plants. Steroidal alkaloids (SAs), also known as "*Solanum* alkaloids" are common constituents of numerous plants belonging to the Solanaceae family, particularly of the genus *Solanum*. Steroidal alkaloids are also produced by a large number of species in the Liliaceae family.

Estimated in the order of 1350 species, *Solanum* is one of the largest genera of flowering plants, representing about a half of the species in the Solanaceae. Diverse structural composition and biological activity, as well as occurrence in food plants including tomato (*Solanum lycopersicum*), potato (*Solanum tuberosum*) and eggplant (*Solanum melongena*), made SAs the subject of extensive investigations (Eich E. 2008. Solanaceae and Convolvulaceae—secondary metabolites: biosynthesis, chemotaxonomy, biological and economic significance: a handbook. Berlin: Springer).

Consisting of a C-27 cholestane skeleton and a heterocyclic nitrogen component, SAs were suggested to be synthesized in the cytosol from cholesterol. Conversion of cholesterol to the alkamine SA should require several hydroxylation, oxidation and transamination reactions (Eich 2008, supra), and in most cases further glycosylation to form steroidal glycoalkaloids (SGAs) (Arnqvist L. et al. 2003. Plant Physiol 131:1792-1799). The oligosaccharide moiety components of SGAs directly conjugate to the hydroxyl group at C-3β of the alkamine steroidal skeleton (aglycone). The oligosaccharide moiety includes D-glucose, D-galactose, L-rhamnose, D-xylose, and L-arabinose, the first two monosaccharides being the predominant units.

SGA biosynthesis depends on genes encoding UDP-glycosyltransferases (UGTs) that decorate the aglycone with various sugar moieties (McCue K F et al., 2005. Plant Sci. 168:267-273; Itkin M et al., 2011. Plant Cell 23:4507-4525). The tomato GLYCOALKALOID METABOLISM 1 (GAME1) glycosyltransferase, a homolog of the potato SGT1 (McCue et al., 2005, supra), catalyzes galactosylation of the alkamine tomatidine (Itkin et al., 2011, supra).

Steroidal alkaloids play a role in protecting plants against a broad range of pathogens, and are thus referred to as phytoanticipins (antimicrobial compounds). Many SGAs are harmful to a variety of organisms including mammals and humans. When present in edible plant parts, these harmful SGAs are referred to as antinutritional substances. The SGAs α-solanine and α-chaconine are the principle toxic substances in potato. These SGAs cause gastrointestinal and neurological disorders and, at high concentrations, may be lethal to humans. Mechanisms of toxicity include disruption of membranes and inhibition of acetylcholine esterase activity (Roddick J G. 1989. Phytochemistry 28:2631-2634). For this reason, total SGA levels exceeding 200 mg per kilogram fresh weight of edible tuber are deemed unsafe for human consumption.

There is an ongoing attempt to elucidate the biosynthesis pathway of steroidal alkaloids and to control their production. U.S. Pat. No. 5,959,180 discloses DNA sequences from potato which encode the enzyme solanidine UDP-glucose glucosyltransferase (SGT). Further disclosed are means and methods for inhibiting the production of SGT and thereby reduce glycoalkaloid levels in Solanaceous plants, for example potato.

Similarly, U.S. Pat. Nos. 7,375,259 and 7,439,419 disclose nucleic acid sequences from potato that encode the enzymes UDP-glucose:solanidine glucosyltransferase (SGT2) and β-solanine/β-chaconine rhamnosyltransferase (SGT3), respectively. Recombinant DNA molecules containing the sequences, and use thereof, in particular, use of the sequences and antisense constructs to inhibit the production of SGT2/SGT3 and thereby reduce levels of the predominant steroidal glycoalkaloids α.-chaconine and α-solanine in Solanaceous plants such as potato are also described.

The inventors of the present invention have recently identified three glycosyltransferases that are putatively involved in the metabolism of tomato steroidal alkaloids (GLYCOALKALOID METABOLISM 1-3 (GAME1-3). More specifically, alterations in GAME1 expression modified the SA profile in tomato plants in both reproductive and vegetative parts. It is suggested that these genes are involved in the metabolism of tomatidine (the α-tomatine precursor) partially by generating the lycotetraose moiety (Itkin et al., 2011, supra).

International Patent Application Publication No. WO 00/66716 discloses a method for producing transgenic organisms or cells comprising DNA sequences which code for sterol glycosyl-transferases. The transgenic organisms include bacteria, fungi, plants and animals, which exhibit an increased production of steroid glycoside, steroid alkaloid and/or sterol glycoside compared to that of wild-type organisms or cells. The synthesized compounds are useful in the pharmaceutical and foodstuff industries as well as for protecting plants.

U.S. Patent Application Publication No. 2012/0159676 discloses a gene encoding a glycoalkaloid biosynthase enzyme derived from a plant belonging to the family Solanaceae for example potato (*Solanum tuberosum*). A method for producing/detecting a novel organism using a gene encoding the protein is also disclosed.

U.S. Patent Application Publication No. 2013/0167271 and International Application Publication No. WO 2012/095843 relate to a key gene in the biosynthesis of steroidal saponins and steroidal alkaloids and to means and methods for altering the gene expression and the production of steroidal saponins and steroidal alkaloids.

A paper of the inventors of the present invention, published after the priority date of the present invention, describes an array of 10 genes that partake in SGA biosynthesis. 5-7 of the genes were found to exist as a cluster on chromosome 7 while additional two reside adjacent in a duplicated genomic region on chromosome twelve. Following systematic functional analysis a novel SGA biosynthetic pathway starting from cholesterol up to the tetrasaccharide moiety linked to the tomato SGA aglycone has been proposed (Itkin M. et al., 2013 Science 341(6142):175-179).

The demand for higher food quantities and food with improved quality continues to increase Improved nutritional qualities as well as removal of antinutritional traits are both of high demand. In the course of crop domestication, levels of anti-nutrients were reduced by breeding, However, Solanaceous crop plant still contain significant amount of antinutritional substances, particularly steroidal glycoalkaloids.

Thus, there is a demand for, and would be highly advantageous to have means and method for controlling the production of steroidal alkaloids in Solanaceous plant, for obtaining high quality non-toxic food products as well as for the production of steroidal alkaloids with beneficial, particularly therapeutic, effects.

SUMMARY OF THE INVENTION

The present invention relates to key genes and enzymes in the biosyntheses pathway converting cholesterol to steroidal glycoalkaloids (SGA), useful for modulating the expression of steroidal alkaloids and in plants. Particularly, the present invention relates to transgenic Solanaceous plants with reduced content of antinutritional alkaloids.

The present invention is based in part on the unexpected discovery that the biosynthesis of SGAs in Solanaceous plant involves an array of genes, wherein 5-7 of the genes (depending on the plant species) are clustered on chromosome 7 and additional two genes are placed adjacent in a duplicated genomic region on chromosome 12. Several regulatory genes, including transcription factors were found to be co-expressed with the clustered genes. Modulating the expression of particular genes within the array enabled strict control of the production of steroidal alkaloids and glycosylated derivatives thereof. Unexpectedly, modulating the expression of a single gene or transcription factor resulted in significant elevation/reduction in the content of solanine and/or chaconine in tomato plants and of tomatine in tomato plants. Particularly, the present invention now shows that modulating a single transcription factors, designated herein GAME9-transcription factor, resulted in strict control on the production of steroidal glycoalkaloids in potato tuber peels. Inhibiting the expression of a gene encoding 2-oxoglutarate-dependent dioxygenase (GAME11) resulted in a significant reduction in α-tomatine level and accumulation of several cholestanol-type saponins in tomato plants.

According to one aspect, the present invention provides a genetically modified plant comprising at least one cell having altered expression of at least one gene selected from the group consisting of a gene encoding GAME9-transcription factor, a gene encoding 2-oxoglutarate-dependent dioxygenase (GAME11), a gene encoding basic helix-loop-helix (BHLH)-transcription factor or a combination thereof, wherein the genetically modified plant has an altered content of at least one steroidal alkaloid or a glycosylated derivative thereof compared to a corresponding unmodified plant.

According to certain embodiments, the genetically modified plant has an altered expression of the gene encoding GAME9-transcription factor compared to the corresponding unmodified plant. According to exemplary embodiments, the GAME9-transcription factor comprises an amino acid sequence at least 80% homologous to SEQ ID NO: 1. According to some embodiments, the GAME9-transcription factor comprises the amino acid sequence set forth in SEQ ID NO: 1. According to additional embodiments, the GAME9-transcription factor comprises the amino acid sequence set forth in SEQ ID NO:2.

According to yet additional embodiments, the gene encoding the GAME9-transcription factor, designated herein GAME9, comprises the nucleic acid sequence set forth in any one of SEQ ID NO:3, SEQ ID NO:4, SEQ ID NO:5 and SEQ ID NO:6.

According to other embodiments, the genetically modified plant has an altered expression of the gene encoding 2-oxoglutarate-dependent dioxygenase (GAME11). According to exemplary embodiments, the 2-oxoglutarate-dependent dioxygenase comprises an amino acid sequence at least 80% homologous to SEQ ID NO:7. According to some embodiments, the 2-oxoglutarate-dependent dioxygenase comprises the amino acid sequence set forth in SEQ ID NO:7. According to additional embodiments, the 2-oxoglutarate-dependent dioxygenase comprises the amino acid sequence set forth in SEQ ID NO:8.

According to yet additional embodiments, the gene encoding the 2-oxoglutarate-dependent dioxygenase, designated herein GAME11, comprises the nucleic acid sequence set forth in any one of SEQ ID NO:9, SEQ ID NO:10, SEQ ID NO:11 and SEQ ID NO:12.

According to further embodiments, the genetically modified plant has an altered expression of the gene encoding BHLH transcription factor compared to the corresponding unmodified plant. According to exemplary embodiments, the BHLH-transcription factor comprises an amino acid sequence at least 80% homologous to SEQ ID NO:13. According to some embodiments, the BHLH-transcription factor comprises the amino acid sequence set forth in SEQ ID NO:13.

According to yet additional embodiments, the gene encoding the BHLH transcription factor, designated herein BHLH comprises the nucleic acid sequence set forth in any one of SEQ ID NO:14, SEQ ID NO:15, SEQ ID NO:16 and SEQ ID NO:17.

According to yet additional embodiments, the genetically modified plant comprises at least one cell having altered expression of a gene encoding GAME9-transcription factor, a gene encoding 2-oxoglutarate-dependent dioxygenase and a gene encoding (BHLH)-transcription factor compared to the corresponding unmodified plant.

According to certain embodiments, the plant is a Solanaceous plant. According to certain exemplary embodiments, the Solanaceous plant is selected from the group consisting of potato, tomato and eggplant.

According to certain embodiments, the expression of the at least one gene or any combination thereof in the genetically modified plant is inhibited compared to its expression in the corresponding unmodified plant, thereby the genetically modified plant comprises reduced content of at least one steroidal alkaloid or a glycosylated derivative thereof compared to said corresponding unmodified plant. According to certain exemplary embodiments, the genetically modified plant comprises non-toxic amount of antinutritional steroidal alkaloid or a glycosylated derivative thereof.

It is to be understood that inhibiting the expression of the at least one gene or combination thereof may be achieved by various means, all of which are explicitly encompassed within the scope of present invention. According to certain embodiments, inhibiting the expression of GAME9, GAME11 or BHLH can be affected at the genomic and/or the transcript level using a variety of molecules that interfere with transcription and/or translation including, but not limited to, antisense, siRNA, Ribozyme, or DNAzyme molecules. Inserting a mutation to the at least one gene, including deletions, insertions, site specific mutations, zinc-finger nucleases and the like can be also used, as long as the mutation results in down-regulation of the gene expression. According to other embodiments, expression is inhibited at the protein level using antagonists, enzymes that cleave the polypeptide and the like.

According to certain exemplary embodiments, the genetically modified plant is a transgenic plant comprising at least one cell comprising at least one silencing molecule targeted to a gene selected from the group consisting of GAME9, GAME11, BHLH or a combination thereof. Each possibility represents a separate embodiment of the present invention. According to some embodiments, the at least one silencing molecule is selected from the group consisting of RNA interference molecule and antisense molecule. According to these embodiments, the transgenic plant comprises reduced content of at least one steroidal alkaloid or glycosylated derivative thereof compared to non-transgenic plant. According to certain embodiments, the at least one steroidal alkaloid is steroidal glycoalkaloid. According to certain exemplary embodiments, the steroidal glycoalkaloid is selected from the group consisting of α-solanine, α-chaconine, solmargine, solasonine, tomatine, tomatidine and derivatives thereof.

According to some embodiments, the transgenic plant comprises a plurality of cells comprising the silencing molecule targeted to at least one gene selected from the group consisting of GAME9, GAME11 and BHLH. According to additional embodiments, the majority of the plant cells comprise the silencing molecule.

According to certain embodiments, the transgenic plant comprising the at least one silencing molecule is a Solanaceous crop plant having a reduced content of at least one steroidal glycoalkaloid selected from the group consisting of solanine, solmargine, solasonine and chaconine. According to certain embodiments, the Solanaceous crop plant is potato. According to other embodiments, the Solanaceous crop plant is eggplant.

According to other embodiments, the transgenic plant comprising the at least one silencing molecule is a tomato plant having a reduced content of tomatine, tomatidine or derivatives thereof.

The silencing molecule target to at least one of GAME9, GAME11 and BHLH can be designed as is known to a person skilled in the art. According to certain embodiments, the silencing molecule comprises a polynucleotide having a nucleic acid sequence substantially complementary to a region of the GAME9 gene or a complementary sequence thereof, having the nucleic acids sequence set forth in any one of SEQ ID NO:4, SEQ ID NO:6, SEQ ID NO:5 and SEQ ID NO:6. Each possibility represents a separate embodiment of the present invention.

According to certain exemplary embodiments, the silencing molecule is targeted to GAME9 fragment having the nucleic acids sequence set forth in SEQ ID NO:18 or a complementary sequence thereof.

According to certain additional embodiments, the silencing molecule comprises a polynucleotide having a nucleic acid sequence substantially complementary to a region of the GAME11 gene or a complementary sequence thereof, having the nucleic acids sequence set forth in any one of SEQ ID NO:9, SEQ ID NO:10, SEQ ID NO:11 and SEQ ID NO:12. Each possibility represents a separate embodiment of the present invention.

According to certain exemplary embodiments, the silencing molecule is targeted to GAME11 fragment having the nucleic acids sequence set forth in SEQ ID NO:19 or a complementary sequence thereof.

According to certain further embodiments, the silencing molecule comprises a polynucleotide having a nucleic acid sequence substantially complementary to a region of the BHLH gene or a complementary sequence thereof, having the nucleic acids sequence set forth in any one of SEQ ID NO:14, SEQ ID NO:15, SEQ ID NO:16 and SEQ ID NO:17.

According to certain embodiments, the silencing molecule is an antisense RNA.

According to certain exemplary embodiments, the silencing molecule is an RNA interference (RNAi) molecule. According to some embodiments, the silencing molecule is a double-stranded (ds)RNA molecule. According to certain embodiments, the first and the second polynucleotides are separated by a spacer. According to exemplary embodiments, the spacer sequence is an intron. According to yet further embodiments, the expression of the first and the second polynucleotides is derived from one promoter. According to other embodiments, expression of the first and the second polynucleotides are derived from two promoters; the promoters can be identical or different. Each possibility represents a separate embodiment of the present invention.

According certain exemplary embodiments, the dsRNA is targeted to GAME9, said dsRNA molecule comprises a first polynucleotide having the nucleic acid sequence set forth in SEQ ID NO:18 and a second polynucleotide having a nucleic acid sequence complementary to SEQ ID NO:18.

According to certain exemplary embodiments, the present invention provides a transgenic eggplant or potato plant comprising at least one cell comprising at least one RNAi molecule targeted to at least one gene selected from the group consisting of a GAME9 gene having the nucleic acid sequence set forth in any one of SEQ ID NO:4 and SEQ ID NO:6, a GAME11 gene having the nucleic acid sequence set forth in any one of SEQ ID NO:10 and SEQ ID NO:12, BHLH gene having the nucleic acid sequence set forth in any one of SEQ ID NO:15 and SEQ ID NO:17 or a combination thereof, wherein the transgenic plant has a reduced content of at least one steroidal glycoalkaloid selected from the group consisting of α-solanine, solmargine, solasonine, and α-chaconine compared to a corresponding non-transgenic plant. Each possibility represents a separate embodiment of the present invention. According to certain embodiments, the transgenic eggplant or potato plant further comprises elevated amount of at least one of steroidal saponin.

According to additional exemplary embodiments, the present invention provides a transgenic tomato plant comprising at least one cell comprising at least one RNAi molecule targeted to at least one gene selected from the group consisting of a GAME9 gene having the nucleic acid sequence set forth in any one of SEQ ID NO:4 and SEQ ID NO:6, a GAME11 gene having the nucleic acid sequence set forth in any one of SEQ ID NO:10 and SEQ ID NO:12, BHLH gene having the nucleic acid sequence set forth in any one of SEQ ID NO:15 and SEQ ID NO:17 or a combination thereof, wherein the transgenic plant has a reduced content of tomatine, tomatidine or derivatives thereof compared to a corresponding non-transgenic plant. Each possibility represents a separate embodiment of the present invention.

According to certain embodiments, the transgenic tomato plant further comprises elevated amounts of steroidal saponins.

According to certain exemplary embodiments, the present invention provides a transgenic tomato plant comprising at least one cell comprising at least one RNAi molecule targeted to a GAME11 gene having the nucleic acid sequence set forth in any one of SEQ ID NO:10 and SEQ ID NO:12, wherein the transgenic plant has a an elevated content of at least one steroidal saponin compared to a corresponding non-transgenic plant. According to certain embodiments, the steroidal saponin is cholestanol-type saponins Each possibility represents a separate embodiment of the present invention.

According to yet additional embodiments the present invention provides a genetically modified plant having enhanced expression of at least one gene selected from the group consisting of a gene encoding GAME9-transcription factor, a gene encoding 2-oxoglutarate-dependent dioxygenase, a gene encoding basic helix-loop-helix transcription factor (BHLH) or a combination thereof, wherein the genetically modified plant has an increased amount of at least one steroidal alkaloid or a glycosylated derivative thereof compared to a corresponding unmodified plant.

Overexpression of the at least one gene can be obtained by any method as is known to a person skilled in the art. According to certain embodiments, the present invention provides a transgenic plant comprising at least one cell comprising at least one transcribable polynucleotide encoding at least one protein selected from the group consisting of GAME9-transcription factor, 2-oxoglutarate-dependent dioxygenase and BHLH-transcription factor, wherein the transgenic plant comprises elevated content of at least one steroidal alkaloid or a glycosylated derivative thereof compared to a corresponding non-transgenic plant.

According to certain exemplary embodiments, the transgenic plant comprises a transcribable polynucleotide encoding GAME9-transcription factor. According to some embodiments, the transcribable polynucleotide comprises the nucleic acid sequence set forth in any one of SEQ ID NO:3, SEQ ID NO:4, SEQ ID NO:5 and SEQ ID NO:6. Each possibility represents a separate embodiment of the present invention.

According to certain additional exemplary embodiments, the transgenic plant comprises a transcribable polynucleotide encoding 2-oxoglutarate-dependent dioxygenase. According to some embodiments, the polynucleotide comprises the nucleic acid sequence set forth in any one of SEQ ID NO:9, SEQ ID NO:10, SEQ ID NO:11 and SEQ ID NO:12. Each possibility represents a separate embodiment of the present invention.

According to certain further exemplary embodiments, the transgenic plant comprises a transcribable polynucleotide encoding BHLH-transcription factor. According to some embodiments, the polynucleotide comprises the nucleic acid sequence set forth in any one of SEQ ID NO:14, SEQ ID NO:15, SEQ ID NO:16 and SEQ ID NO:17.

According to certain embodiments, the transgenic plant comprises a plurality of cells comprising at least one transcribable polynucleotide encoding at least one protein selected from the group consisting of GAME9-transcription factor, 2-oxoglutarate-dependent dioxygenase and BHLH-transcription factor.

According to yet additional embodiments, the majority of the transgenic cells comprise at least one transcribable polynucleotide encoding at least one protein selected from the group consisting of GAME9-transcription factor, 2-oxoglutarate-dependent dioxygenase and BHLH-transcription factor.

According to certain embodiments, the transgenic plant is a Solanaceous plant, said plant comprises an increased amount of a steroidal glycoalkaloid selected from the group consisting of α-solanine, α-chaconine, solmargine, solasonine, tomatine, tomatidine and derivatives thereof.

According to certain exemplary embodiments, the transgenic Solanaceous plant is selected from the group consisting of potato and eggplant, said plant comprises elevated amount of at least one glycoalkaloid selected from the group consisting of α-solanine, α-chaconine, solmargine, solasonine, and derivatives thereof.

According to further certain exemplary embodiments, the transgenic plant is a tomato plant having an increased amount of tomatine, tomatidine or derivatives thereof.

According to some embodiments, the polynucleotides of the present invention are incorporated in a DNA construct enabling their expression in the plant cell. DNA constructs suitable for use in plants are known to a person skilled in the art. According to one embodiment, the DNA construct comprises at least one expression regulating element selected from the group consisting of a promoter, an enhancer, an origin of replication, a transcription termination sequence, a polyadenylation signal and the like.

The DNA constructs of the present invention are designed according to the results to be achieved. In crop plants, reduction of toxic steroidal glycoalkaloids is desired in the edible parts of the plant, including, for example, fruit and tubers. On the other hand, enriching the content of toxic steroidal glycoalkaloids in non-edible roots and leaves contributes to the resistance of the plant against a broad range of pathogens. Plants overexpressing the steroidal glycoalkaloids can be used for producing them for the pharmaceutical industry.

According to certain embodiments, the DNA construct comprises a promoter. The promoter can be constitutive, induced or tissue specific as is known in the art. Optionally, the DNA construct further comprises a selectable marker, enabling the convenient selection of the transformed cell/tissue. Additionally or alternatively, a reporter gene can be incorporated into the construct, so as to enable selection of transformed cells or tissue expressing the reporter gene.

Suspensions of genetically modified cells and tissue cultures derived from the genetically modified cells are also encompassed within the scope of the present invention. The cell suspension and tissue cultures can be used for the production of desired steroidal glycoalkaloids and, which are then extracted from the cells or the growth medium. Alternatively, the genetically modified cells and/or tissue culture are used for regenerating a transgenic plant having modified expression of at least one of GAME9, GAME11, BHLH or a combination thereof, therefore having modified content of steroidal glycoalkaloids.

The present invention further encompasses seeds of the genetically modified plant, wherein plants grown from said seeds have altered expression of at least one of GAME9, GAME11, BHLH or a combination thereof compared to plants grown from corresponding unmodified seeds, thereby having an altered content of at least one steroidal glycoalkaloid.

According to a further aspect, the present invention provides a method of reducing the content of at least one steroidal alkaloid or a glycosylated derivative thereof in a plant, comprising transforming at least one plant cell with at least one silencing molecule targeted to a nucleic acids sequence encoding at least one protein selected from the group consisting of GAME9-transcription factor, 2-oxoglutarate-dependent dioxygenase and BHLH-transcription factor, thereby producing a plant with reduced content of at least one steroidal alkaloid or a glycosylated derivative thereof compared to a corresponding non-transformed plant. Each possibility represents a separate embodiment of the present invention.

Other objects, features and advantages of the present invention will become clear from the following description and drawings.

BRIEF DESCRIPTION OF THE FIGURES

FIG. 2 summarizes the coexpression analysis of steroidal alkaloid-associated genes in Solanaceous plants. Shared homologs of coexpressed genes for 'baits' from tomato (SlGAME1 and SlGAME4) and potato (StSGT1 and StGAME4). Continuous (r-value>0.8) and dashed (r-value>0.63) lines connect coexpressed genes. *, located in the tomato or potato chromosome 7 cluster. St, *Solanum tuberosum*; Sl, *S. lycopersicum*. Background of gene names corresponds to bait they were found to be coexpressed with (legend above). SP, serine proteinase; PI, proteinase inhibitor; UPL, ubiquitin protein ligase; ELP, extensin-like protein; PK, protein kinase; SR, sterol reductase; RL, receptor-like.

DETAILED DESCRIPTION OF THE INVENTION

Figure 1:
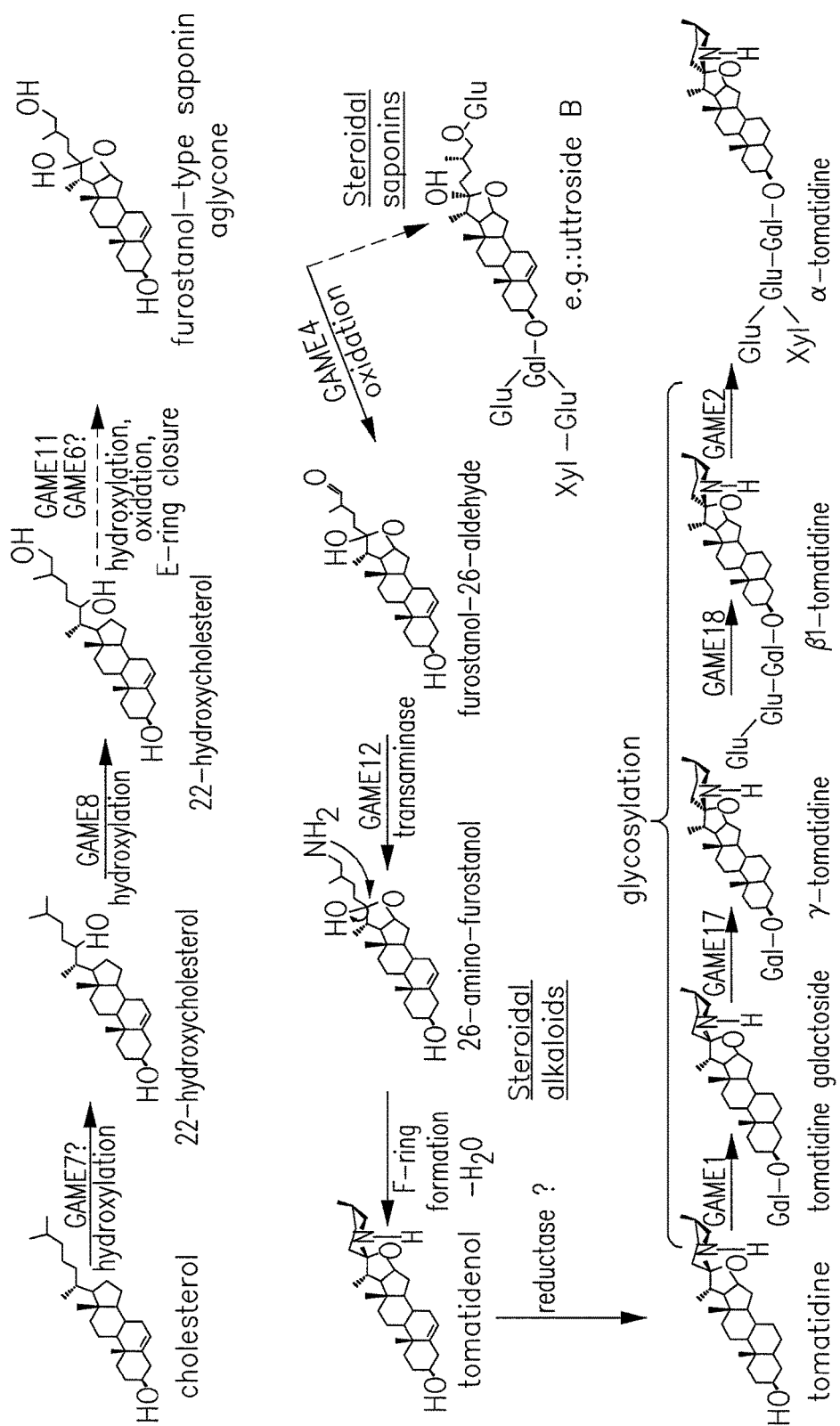
FIG. 1 shows the proposed biosynthetic pathway of steroidal glycoalkaloids in the triterpenoid biosynthetic pathway in Solanaceous plant from cholesterol toward α-tomatine. Dashed and solid arrows represent multiple or single enzymatic reactions in the pathway, respectively.

The present invention discloses an array of co-expressed genes that participate in the biosynthesis pathway of steroidal alkaloids. The present invention further discloses key genes in this pathway, altering the expression of which result in concomitant alteration in the steroidal alkaloid profile. Changing the production level of steroidal alkaloid can result in an improved plants comprising elevated content of steroidal alkaloids having increased resistance to pathogens, or plants having a reduced content of these secondary compounds in the plant edible parts and thus producing improved crops. Alternatively or additionally, controlling the expression of genes revealed in the present invention can be used for the production of desired steroidal alkaloids for further use, for example in the pharmaceutical industry. In particular, the present invention discloses means and methods for producing crop plants of the genus *Solanum* that are devoid of toxic amounts of deleterious steroidal alkaloids typically present in edible parts of these plants. The plants of the present invention are thus of significant nutritional and commercial value.

Definitions

As used herein, the term "Solanaceous" refers to a plant of the genus *Solanum*.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" optionally also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

The term "RNA interference" or "RNAi" refers to the silencing or decreasing of gene expression mediated by small double stranded RNAs. It is the process of sequence-specific, post-transcriptional gene silencing in animals and plants, initiated by inhibitory RNA (iRNA) that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

Typically, the term RNAi molecule refers to single- or double-stranded RNA molecules comprising both a sense and antisense sequence. For example the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

The terms "complementary" or "complement thereof" are used herein to refer to the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

The term "construct" as used herein refers to an artificially assembled or isolated nucleic acid molecule which includes the polynucleotide of interest. In general a construct may include the polynucleotide or polynucleotides of interest, a marker gene which in some cases can also be a gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The terms "promoter element," "promoter," or "promoter sequence" as used herein, refer to a DNA sequence that is located at the 5' end (i.e. precedes) the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

As used herein, the term an "enhancer" refers to a DNA sequence which can stimulate promoter activity, and may be an innate element of the promoter or a heterologous element inserted to enhance the level or tissue-specificity of a promoter.

The term "expression", as used herein, refers to the production of a functional end-product e.g., an mRNA or a protein.

The term "genetically modified plant" refers to a plant comprising at least one cell genetically modified by man. The genetic modification includes modification of an endogenous gene(s), for example by introducing mutation(s) deletions, insertions, transposable element(s) and the like into an endogenous polynucleotide or gene of interest. Additionally or alternatively, the genetic modification includes transforming the plant cell with heterologous polynucleotide. A "genetically modified plant" and a "corresponding unmodified plant" as used herein refer to a plant comprising at least one genetically modified cell and to a plant of the same type lacking said modification, respectively.

The term "transgenic" when used in reference to a plant according to the teachings of the present invention (i.e., a "transgenic plant" refers to a plant that contains at least one heterologous transcribable polynucleotide in one or more of its cells. The term "transgenic material" refers broadly to a plant or a part thereof, including cells or tissues that contain at least one heterologous polynucleotide in at least one of cell. A "transgenic plant" and a "corresponding non transgenic plant" as used herein refer to a plant comprising at least one cell comprising a heterologous transcribable polynucleotide and to a plant of the same type lacking said heterologous transcribable polynucleotide, respectively.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. In contrast, the term "stable transformation" or "stably transformed" refers to the introduction and integration of one or more exogenous polynucleotides into the genome of a cell. The term "stable transformant" refers to a cell which has stably integrated one or more exogenous polynucleotides into the genomic or organellar DNA. It is to be understood that an organism or its cell transformed with the nucleic acids, constructs and/or vectors of the present invention can be transiently as well as stably transformed.

Based on the co-expressed gene array disclosed in the present invention, a pathway from cholesterol to α-tomatine is proposed (FIG. 1). It has been previously described that cholesterol is hydroxylated at C22 by GAME? (US 2012/0159676) followed by GAME8 hydroxylation at the C26 position. The 22,26-dihydroxycholesterol is than hydroxylated at C16 and oxidized at C22 followed by closure of the E-ring by GAME11 and GAME6 to form the furostanol-type aglycone. This order of reactions is supported by the finding of the present invention showing the accumulation of cholestanol-type saponins, lacking hydroxylation at C16 and the hemi-acetal E-ring when silencing GAME11 (FIG. 8A-D). The furostanol-intermediate is oxidized by GAME4 to its 26-aldehyde which is the substrate for transamination catalyzed by GAME12. Nucleophilic attack of the amino-nitrogen at C22 leads to the formation of tomatidenol which is dehydrogenated to tomatidine. Tomatidine is subsequently converted by GAME1 to T-Gal (Itkin et al., 2011 supra). T-Gal in its turn is glucosylated by GAME17 into γ-tomatine, which is further glucosylated by GAME18 to β1-tomatine that is finally converted to α-tomatine by GAME2 (FIG. 1).

The present invention now shows that by modifying expression of an enzyme and/or transcription factors involved in the biosynthetic pathway, the level of steroidal alkaloids, steroidal glycoalkaloids and optionally steroidal saponin can be altered.

Figure 5A:
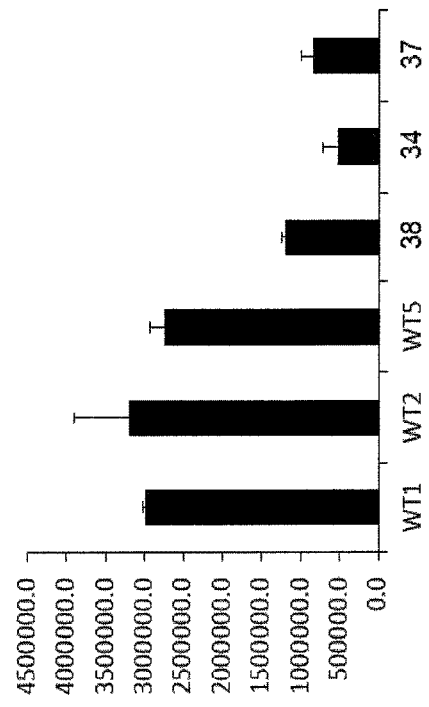
FIG. 5 shows solanine/chaconine levels in peels of tuber of potato plant lines with altered expression of GAME9 compared to wild type plants. Solanine (5A) and chaconine (5B) level in tubers of GAME9 silenced plant; Solanine (5C) and chaconine (5D) levels in tubers of GAME9 overexpressing plants.
Figure 5B:
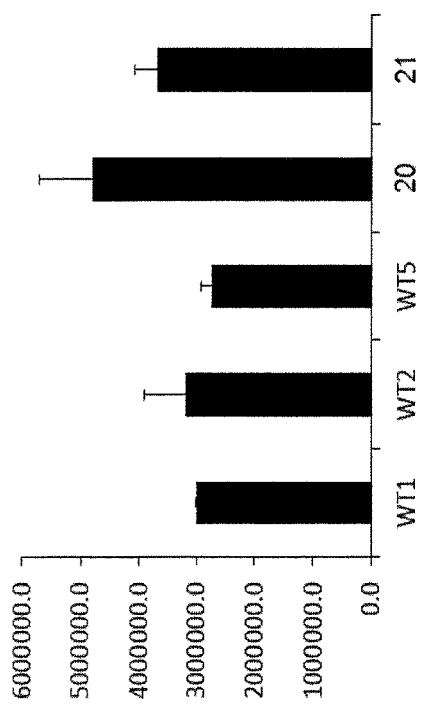
Figure 5C:
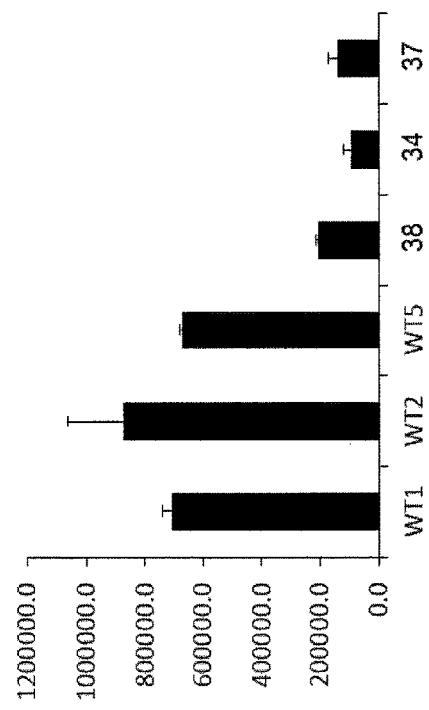
Figure 5D:
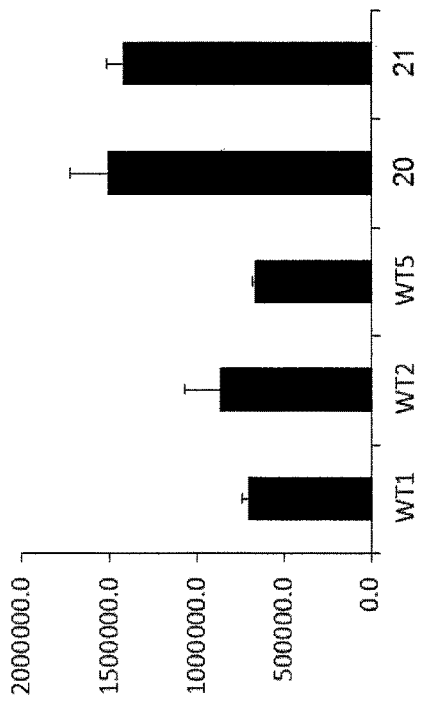
Figure 6:
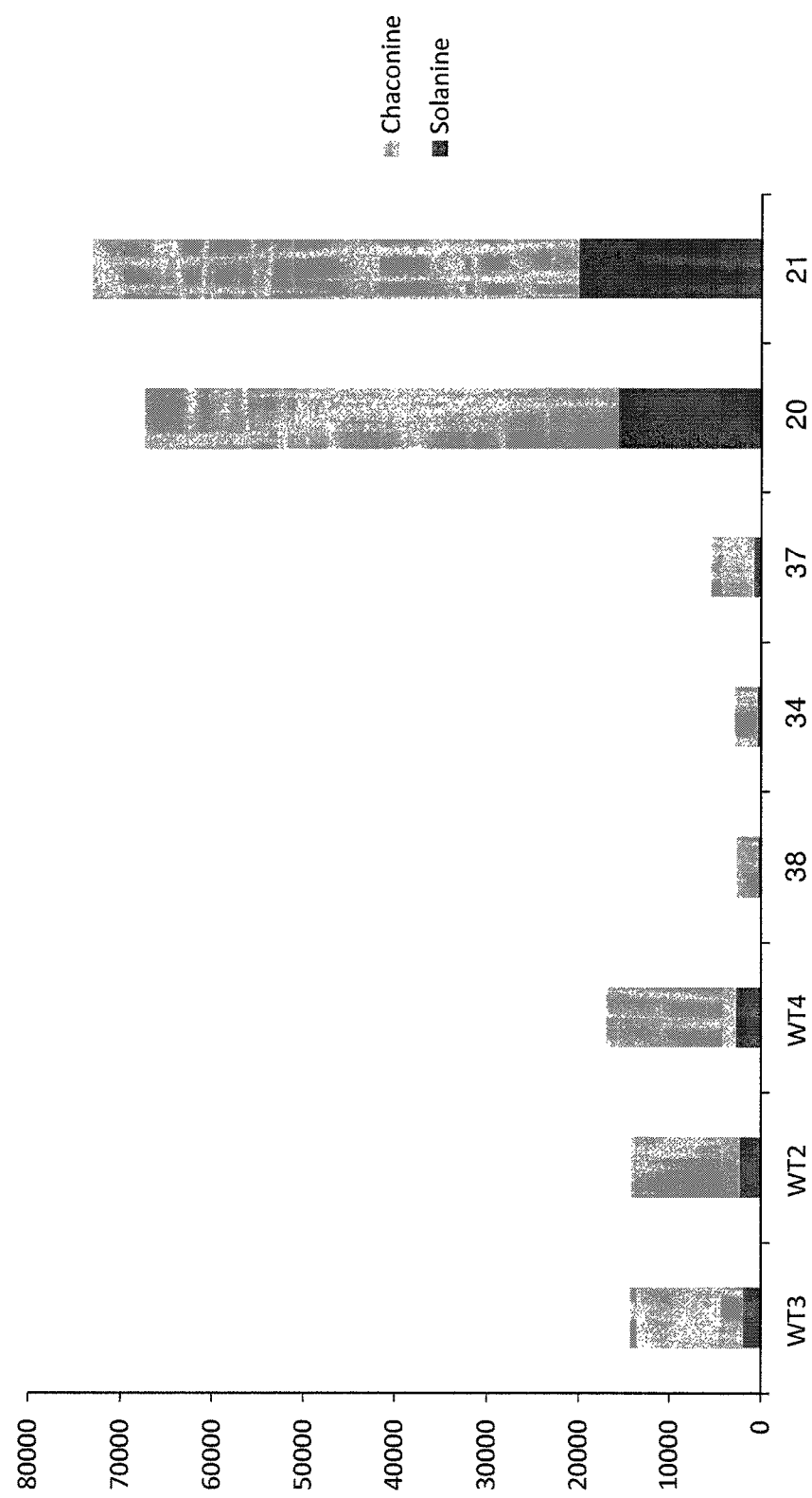
FIG. 6 shows solanine/chaconine levels in leaves of potato plant lines with either silenced (RNAi) or overexpressed (OX) GAME9 compared to wild type plants.
Figure 7:
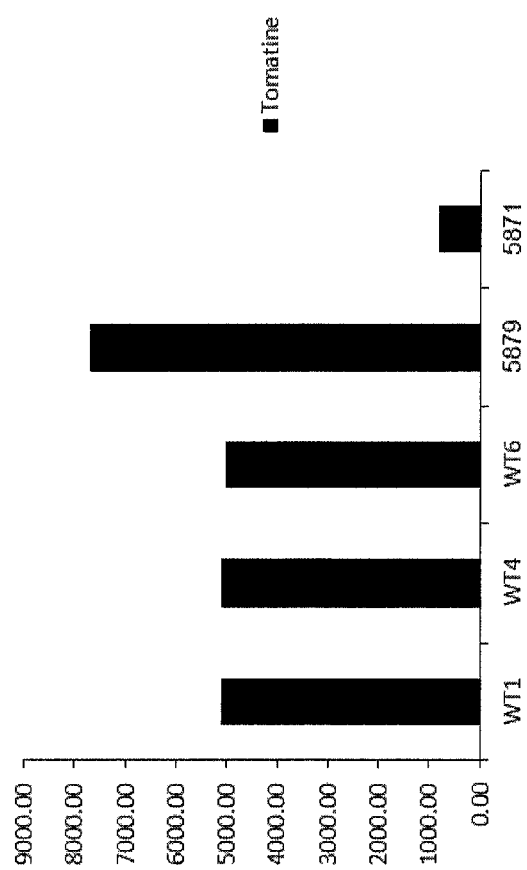
FIG. 7 shows tomatine levels in leaves of tomato plant lines with either silenced (RNAi, line 5871) or overexpressed (OX, line 5879) GAME9 compared to wild type plants.

The present invention now shows that unexpectedly, silencing of a single gene co-expressed with the clustered enzyme-encoding gene in potato plant, resulted in significant reduction in the amount of the steroidal glycoalkaloids α-chaconine and α-solanine, while overexpression of this gene resulted in significant increase in the content of these substances (FIGS. 5 and 6). This gene was found to include coding sequence comprising an AP2 domain, and therefore postulated to be a transcription factor, designated herein GAME9-transcription factor, encoded by GAME9.

According to one aspect, the present invention provides a genetically modified plant comprising at least one cell having altered expression of at least one gene selected from the group consisting of a gene encoding GAME9-transcription factor, a gene encoding 2-oxoglutarate-dependent dioxygenase, a gene encoding basic helix-loop-helix (BHLH)-transcription factor or a combination thereof, wherein the genetically modified plant has an altered content of at least one steroidal alkaloid or a glycosylated derivative thereof compared to a corresponding unmodified plant.

While being exemplified in a genetically modified plant, the teachings of the present invention may further enable manipulating the synthesis of steroidal alkaloids or glycosylated derivatives thereof in any organism naturally capable of steroidal alkaloid synthesis. As exemplified herein for 2-oxoglutarate-dependent dioxygenase (GAME11), manipulating the expression of the genes of the present invention can further lead to the manipulation of steroidal saponin synthesis.

Thus, according to additional aspect, the present invention provides a genetically modified organism comprising at least one cell having altered expression of at least one gene selected from the group consisting of a gene encoding GAME9-transcription factor, a gene encoding 2-oxoglutarate-dependent dioxygenase, a gene encoding basic helix-loop-helix (BHLH)-transcription factor or a combination thereof compared to an unmodified organism, wherein the genetically modified organism has an altered content of at least one compound selected from steroidal saponin, steroidal alkaloid and glycosylated derivatives thereof compared to a corresponding unmodified organism.

Unexpectedly, the present invention now shows that SGA levels can be severely reduced in potato tubers by modifying expression of an enzyme and/or transcription factors involved in the steroidal alkaloids biosynthetic pathway.

According to certain embodiments, the expression of the at least one gene selected from the group consisting of a gene encoding GAME9-transcription factor, a gene encoding 2-oxoglutarate-dependent dioxygenase, a gene encoding BHLH-transcription factor or the combination thereof in the genetically modified plant is inhibited compared to its expression in the corresponding unmodified plant, thereby the genetically modified plant comprises reduced content of at least one steroidal alkaloid or a glycosylated derivative thereof compared to a corresponding unmodified plant.

According to certain embodiments, the genetically modified plant comprises non-toxic amount of steroidal alkaloid or a glycosylated derivative thereof. As used herein, the term "non-toxic amount" refers to less than 200 mg of antinutritional steroidal; alkaloids or glycoalkaloids per kilogram fresh weight of an edible plant part. According to certain exemplary embodiments, the genetically modified plant comprises non-detectable amount of antinutritional steroidal alkaloid or a glycosylated derivative thereof.

Down-regulation or inhibition of the gene expression can be effected on the genomic and/or the transcript level using a variety of molecules that interfere with transcription and/or translation (e.g., antisense, siRNA, Ribozyme, or DNAzyme), or on the protein level using, e.g., antagonists, enzymes that cleave the polypeptide, and the like.

According to certain exemplary embodiments, the genetically modified plant is a transgenic plant comprising at least one cell comprising at least one silencing molecule targeted to a gene selected from the group consisting of GAME9, GAME11 and BHLH. Each possibility represents a separate embodiment of the present invention.

According to some embodiments, the organism comprising the silencing molecule has an elevated content of at least one steroidal saponin or a derivative thereof compared to a corresponding non-transgenic plant.

The silencing molecule target to at least one of GAME9, GAME11 and BHLH can be designed as is known to a person skilled in the art. According to certain embodiments, the silencing molecule comprises a polynucleotide having a nucleic acid sequence substantially complementary to a region of the GAME9 gene, the gene having the nucleic acids sequence set forth in any one of SEQ ID NO:4 and SEQ ID NO:6.

According to certain additional embodiments, the silencing molecule comprises a polynucleotide having a nucleic acid sequence substantially complementary to a region of the GAME11 gene, the gene having the nucleic acids sequence set forth in any one of SEQ ID NO:10 and SEQ ID NO:12.

According to certain further embodiments, the silencing molecule comprises a polynucleotide having a nucleic acid sequence substantially complementary to a region of the BHLH gene, the gene having the nucleic acids sequence set forth in any one of SEQ ID NO:15 and SEQ ID NO:17.

Antisense Molecules

Antisense technology is the process in which an antisense RNA or DNA molecule interacts with a target sense DNA or RNA strand. A sense strand is a 5' to 3' mRNA molecule or DNA molecule. The complementary strand, or mirror strand, to the sense is called an antisense. When an antisense strand interacts with a sense mRNA strand, the double helix is recognized as foreign to the cell and will be degraded, resulting in reduced or absent protein production. Although DNA is already a double stranded molecule, antisense technology can be applied to it, building a triplex formation.

RNA antisense strands can be either catalytic or non-catalytic. The catalytic antisense strands, also called ribozymes, cleave the RNA molecule at specific sequences. A non-catalytic RNA antisense strand blocks further RNA processing.

Antisense modulation of cells and/or tissues levels of the GAME9, GAME1 and BHLH gene or any combination thereof may be effected by transforming the organism cells or tissues with at least one antisense compound, including antisense DNA, antisense RNA, a ribozyme, DNAzyme, a locked nucleic acid (LNA) and an aptamer. In some embodiments the molecules are chemically modified. In other embodiments the antisense molecule is antisense DNA or an antisense DNA analog.

RNA Interference (RNAi) Molecules

RNAi refers to the introduction of homologous double stranded RNA (dsRNA) to target a specific gene product, resulting in post transcriptional silencing of that gene. This phenomena was first reported in *Caenorhabditis elegans* by Guo and Kemphues (1995, Cell, 81(4):611-620) and subsequently Fire et al. (1998, Nature 391:806-811) discovered that it is the presence of dsRNA, formed from the annealing of sense and antisense strands present in the in vitro RNA preps, that is responsible for producing the interfering activity.

The present invention contemplates the use of RNA interference (RNAi) to down regulate the expression of GAME9, GAME11, BHLH or combination thereof to attenuate the level of steroidal alkaloids/glycoalkaloids in plants. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available as exemplified herein below.

The dsRNA can be transcribed from the vectors as two separate strands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. Alternatively, a single promoter can derive the transcription of single-stranded hairpin polynucleotide having self-complementary sense and antisense regions that anneal to produce the dsRNA.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases. There is no upper limit on the length of the dsRNA that can be used. For example, the dsRNA can range from about 21 base pairs (bp) of the gene to the full length of the gene or more.

According to certain currently typical embodiments, the silencing molecule is RNAi targeted to the GAME9 gene, comprising the nucleic acid sequence set forth in SEQ ID NO:18 or a complementary sequence thereof. According to additional typical embodiments, the silencing molecule is RNAi targeted to the GAME11 gene, comprising the nucleic acid sequence set forth in SEQ ID NO:19 or a complementary sequence thereof.

DNAzyme Molecules

Another agent capable of down-regulating the expression of GAME9, GAME11 or BHLH is a DNAzyme molecule, which is capable of specifically cleaving an mRNA transcript or a DNA sequence of the GAME9, GAME11 or BHLH. DNAzymes are single-stranded polynucleotides that are capable of cleaving both single- and double-stranded target sequences. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (for review of DNAzymes, see: Khachigian, L. M. (2002) Curr Opin Mol Ther 4, 119-121).

Examples of construction and amplification of synthetic, engineered DNAzymes recognizing single- and double-stranded target cleavage sites are disclosed in U.S. Pat. No. 6,326,174.

Enzymatic Oligonucleotide

The terms "enzymatic nucleic acid molecule" or "enzymatic oligonucleotide" refers to a nucleic acid molecule which has complementarity in a substrate binding region to a specified gene target, and also has an enzymatic activity which is active to specifically cleave target RNA of GAME9, GAME11 or BHLH, thereby silencing each of the genes. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme, RNAenzyme. The specific enzymatic nucleic acid molecules described in the instant application are not limiting and an enzymatic nucleic acid molecule of this invention requires a specific substrate binding site which is complementary to one or more of the target nucleic acid regions, and that it have nucleotide sequences within or surrounding that substrate binding site which impart a nucleic acid cleaving and/or ligation activity to the molecule. U.S. Pat. No. 4,987,071 discloses examples of such molecules.

Mutagenesis

Inhibiting the expression of endogenous GAME9, GAME11 or BHLH genes can be also achieved by the introduction of one or more point mutations into a nucleic acid molecule encoding the corresponding proteins. Mutations can be introduced using, for example, site-directed mutagenesis (see, e.g. Wu Ed., 1993 Meth. In Enzymol. Vol. 217, San Diego: Academic Press; Higuchi, "Recombinant PCR" in Innis et al. Eds., 1990 PCR Protocols, San Diego: Academic Press, Inc). Such mutagenesis can be used to introduce a specific, desired amino acid insertion, deletion or substitution. Several technologies for targeted mutagenesis are based on the targeted induction of double-strand breaks (DSBs) in the genome followed by error-prone DNA repair. Mostly commonly used for genome editing by this methods are custom designed nucleases, including zinc figure nucleases and Xanthomonas-derived transcription activator-like effector nuclease (TALEN) enzymes.

An alternative method for genome engineering has been developed recently, based on the bacterial CRISPR (clustered regularly interspaced short palindromic repeats)/Cas (CRISPR-associated) type II prokaryotic adaptive immune system. This RNA-based technology is very specific and allows targeted cleavage of genomic DNA guided by a customizable small noncoding RNA, resulting in gene modifications by both non-homologous end joining (NHEJ) and homology-directed repair (HDR) mechanisms (Belhaj K. et al., 2013. Plant Methods 2013, 9:39).

Chemical mutagenesis using an agent such as Ethyl Methyl Sulfonate (EMS) can be employed to obtain a population of point mutations and screen for mutants of the GAME9, GAME11 or BHLH genes that may become silent or down-regulated. In plants, methods relaying on introgression of genes from natural populations can be used. Cultured and wild types species are crossed repetitively such that a plant comprising a given segment of the wild genome is isolated. Certain plant species, for example Maize (corn) or snapdragon have natural transposons. These transposons are either autonomous, i.e. the transposase is located within the transposon sequence or non-autonomous, without a transposase. A skilled person can cause transposons to "jump" and create mutations. Alternatively, a nucleic acid sequence can be synthesized having random nucleotides at one or more predetermined positions to generate random amino acid substituting.

Overexpression

According to yet additional embodiments the present invention provides a genetically modified plant having enhanced expression of at least one gene selected from the group consisting of a gene encoding GAME9-transcription factor, a gene encoding 2-oxoglutarate-dependent dioxygenase, a gene encoding basic helix-loop-helix transcription factor (BHLH) or a combination thereof, wherein the genetically modified plant has an increased amount of at least one steroidal alkaloid or a glycosylated derivative thereof compared to a corresponding unmodified plant. In plants, steroidal alkaloids play a role in protecting the plant from various pathogens. Steroidal alkaloids are referred to as phytoanticipins, i.e. low molecular weight anti-microbial compounds that are present in the plant before challenge by microorganisms or produced after infection solely from preexisting constituents. Over-expression of GAME9, GAME11, BHLH or any combination thereof in non-edible parts of the plant can thus enhance the plant resistance to steroidal-alkaloid-sensitive pathogens.

Transgenic Plants

Cloning of a polynucleotide encoding a protein of the present invention selected from the group consisting of GAME9-transcription factor, 2-oxoglutarate-dependent dioxygenase and BHLH-transcription factor or a molecule that silences a gene encoding same can be performed by any method as is known to a person skilled in the art. Various DNA constructs may be used to express the desired gene or silencing molecule targeted to the gene in a desired organism.

According to certain embodiments, the gene or a silencing molecule targeted thereto form part of an expression vector comprising all necessary elements for expression of the gene or its silencing molecule. According to certain embodiments, the expression is controlled by a constitutive promoter. According to certain embodiments, the constitutive promoter is specific to a plant tissue. According to these embodiments, the tissue specific promoter is selected from the group consisting of root, tuber, leaves and fruit specific promoter. Root specific promoters are described, e.g. in Martinez, E. et al. 2003. Curr. Biol. 13:1435-1441. Fruit specific promoters are described among others in Estornell L. H et al. 2009. Plant Biotechnol. J. 7:298-309 and Fernandez A. I. Et al. 2009 Plant Physiol. 151:1729-1740. Tuber specific promoters are described, e.g. in Rocha-Sosa M, et al., 1989. EMBO J. 8:23-29; McKibbin R. S. et al., 2006. Plant Biotechnol J. 4(4):409-18. Leaf specific promoters are described, e.g. in Yutao Yang, Guodong Yang, Shijuan Liu, Xingqi Guo and Chengchao Zheng. Science in China Series C: Life Sciences. 46: 651-660.

According to certain embodiments, the expression vector further comprises regulatory elements at the 3' non-coding sequence. As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I L et al. (1989. Plant Cell 1:671-680).

Those skilled in the art will appreciate that the various components of the nucleic acid sequences and the transformation vectors described in the present invention are operatively linked, so as to result in expression of said nucleic acid or nucleic acid fragment. Techniques for operatively linking the components of the constructs and vectors of the present invention are well known to those skilled in the art. Such techniques include the use of linkers, such as synthetic linkers, for example including one or more restriction enzyme sites.

Methods for transforming a plant according to the teachings of the present invention are known to those skilled in the art. As used herein the term "transformation" or "transforming" describes a process by which a foreign DNA, such as a DNA construct, including expression vector, enters and changes a recipient cell into a transformed, genetically altered or transgenic cell. Transformation may be stable, wherein the nucleic acid sequence is integrated into the organism genome and as such represents a stable and inherited trait, or transient, wherein the nucleic acid sequence is expressed by the cell transformed but is not integrated into the genome, and as such represents a transient trait. According to preferred embodiments the nucleic acid sequence of the present invention is stably transformed into the plant cell.

The genetically altered plants having altered content of the desired steroidal alkaloid(s) or steroidal saponin(s) according to the teachings of the present invention are typically first selected based on the expression of the gene or protein. Plants having enhanced or aberrant expression of the gene or protein, are then analyzed for the content of steroidal alkaloids and optionally of steroidal saponins.

Detection of mutated GAME9, GAME11 or BHLH gene and/or the presence of silencing molecule targeted to the gene and/or over-expression of the genes is performed employing standard methods of molecular genetics, known to a person of ordinary skill in the art.

For measuring the gene(s) or silencing molecule(s) expression, cDNA or mRNA should be obtained from an organ in which the nucleic acid is expressed. The sample may be further processed before the detecting step. For example, the polynucleotides in the cell or tissue sample may be separated from other components of the sample, may be amplified, etc. All samples obtained from an organism, including those subjected to any sort of further processing are considered to be obtained from the organism.

Detection of the gene(s) or the silencing molecule(s) typically requires amplification of the polynucleotides taken from the candidate altered organism Methods for DNA amplification are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid based sequence amplification (NASBA).

According to certain embodiments, the nucleic acid sequence comprising the GAME9, GAME11 or BHLH gene or its silencing molecule further comprises a nucleic acid sequence encoding a selectable marker. According to certain embodiments, the selectable marker confers resistance to antibiotic or to an herbicide; in these embodiments the transgenic plants are selected according to their resistance to the antibiotic or herbicide.

The content of steroidal alkaloids and/or steroidal saponins is measured as exemplified hereinbelow and as is known to a person skilled in the art.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Plant Material, Treatments and Generation of Transgenic Plants

Tomato (Solanum lycopersicum; cv. Micro Tom) and potato (Solanum tuberosum; cultivar Desiree) plants were collected as described previously (Itkin et al., 2001, supra). In potato, when the green parts started to dry, mature tubers (Stage 3) were collected, washed of soil, dried and kept at 4° C., at complete darkness.

The GAME9-silenced (RNAi) and overexpression (OX) constructs were created by introducing the corresponding GAME9 DNA fragments to pK7GWIWG2(II) and pJCV52 binary vectors, respectively. Transgenic lines for silencing and overexpression of GAME9 in tomato and potato were generated and tissue extracts were prepared and analyzed according to Itkin et al. (2011, supra).

Table 1 below describes the oligonucleotides used for generation of the constructs described herein. The GAME4-silencing (RNAi; GAME4i), GAME4 overexpressing (GAME4oe) and GAMER-silencing constructs were generated as described previously (Itkin et al., 2001, supra; WO 2012/095843).

TABLE 1

Oligonucleotides used for construct production

| Name | Sequence 5' to 3'/ Description | SEQ ID NO. |
|---|---|---|
| S107g0434 20 EcoRI Fw | AAAAAgaattcCGGATCTTCTCTCGAACTGGTCAA To prepare GAME11 virus-induced gene silencing (VIGS) construct | 20 |
| S107g0434 20 EcoRI Rv | AAAAAgaattcCACTTTCATTGCITCATCCATTAGATC T To prepare GAME11 VIGS construct | 21 |
| S107g0435 00 EcoRI Fw | AAAAAgaattcCTTAGCTTATGGCCACATCACACCTT To prepare GAME18 VIGS construct | 22 |
| S107g0435 00 EcoRI Rv | AAAAAgaattcACTCAAGATTTGGTGAAGCTGTGGTT To prepare GAME18 VIGS construct | 23 |
| G8- Forward (AscI) | AAAAAGGCGCGCCAATCATAGAGAAGAAAGAAGACG To construct RNAi of GAME8 | 24 |
| G8- Reverse (NotI) | AAAAAGCGGCCGCACTCCTGCAGGAATTGTCATTTCTC To construct RNAi of GAME8 | 25 |
| GAME9 RNAi NotI Fw | aaaaaGCGGCCGCATGAGTATTGTAATTGATGATGATG AAATC To construct RNAi of GAME9 | 26 |

TABLE 1-continued

Oligonucleotides used for construct production

| Name | Sequence 5' to 3'/ Description | SEQ ID NO. |
|---|---|---|
| GAME9 RNAi AscI Rv | aaaaGGCGCGCCCACACGCCACAGATGGTTCTT<br>To construct RNAi of GAME9 | 27 |
| GAME9-Tom GW Fw | GGGGACAAGTTTGTACAAAAAAGCAGGCTATGAGTATT GTAATTGATGATGATGAAATC<br>To pick up the gene from cDNA for overexpression (good for tomato) | 28 |
| GAME9-Tom GW Rv | GGGGACCACTTTGTACAAGAAAGCTGGGTTCATACTAC CTTCTGTCCTAAGCCT<br>To pick up the gene from cDNA for overexpression (good for tomato) | 29 |
| GAME9-Pot GW Fw | GGGGACAAGTTTGTACAAAAAAGCAGGCTATGAATATT GCAATTGATGATGATGA<br>To pick up the gene from cDNA for overexpression (good for potato) | 30 |
| GAME9-Pot GW Rv | GGGGACCACTTTGTACAAGAAAGCTGGGTTCATTTGTA TCAACATTTGTAAATTCACAC<br>To pick up the gene from cDNA for overexpression (good for potato) | 31 |

Co-Expression Analysis

The tomato GAME1 (Solyc07g043490) and its potato ortholog SGT1 (PGSC003DMG400011749) were used as 'baits' in the co-expression analysis, resulting in lists (sorted in descending order by r-value≥0.8) of co-expressed genes (for each 'bait' separately). Two homologous genes were subsequently identified (Solyc12g006460 and PGSC0003DMG400024274 in tomato and potato, respectively), which were highly correlated with the "bait" genes (r-value>0.9 in both species). Those genes were identified as GLYCOALKALOID METABOLISM 4 (GAME4, WO 2012/095843). The GAME4 genes were further added as 'baits' to the previous (GAME1) co-expression analysis. The co-expression lists for GAME1 (SGT1) and GAME4 in both species were used to construct co-expression correlation network. The analysis was performed as follows: tomato RNAseq transcriptome data from different tissues and organs (flesh, peel, seeds, roots, leaves, buds, flowers, pollen) and developmental stages (25 experiments in total) (Itkin et al., 2011, ibid) and potato RNAseq transcriptome data from different tissues and organs (40 experiments in total) (US 2012/0159676), were used. First, an R script was used to perform co-expression analysis (for each species) and the list of co-expressed genes was constructed as a FASTA file, using a Perl script. Finally, BLAST all tools (Camacho C. et al., 2009. BMC Bioinform 10:421) were used to find shared homologs between the two species. The tblastx criteria for homolog similarity were set to p-value>0.05, minimum 25 nucleotides, and at least 60 percent similarity as an overall identity for each gene. The co-expression network was visualized with the Cytoscape program (Shannon P. et al., 2003. Genome Res. 13:2498-2504).

Phylogenetic Analysis

The protein sequences were aligned using the Muscle algorithm and the phylogenetic tree was analyzed and visualized by the SeaView v4.3.5 program using the maximum likelihood method by PhyML 3.0 (Expósito-Rodriguez M et al., 2008. BMC Plant Biol. 8:131) with the following settings: model—LG; The approximate likelihood ratio test (aLRT) Shimodaira-Hasegawa-like (SH-like) procedure was used as a statistical test to calculate branch support (branch support—aLRT (SH-like)); invariable sites—optimized; across site rate variation—optimized; tree searching operations—best for NNI & SPR; starting tree—BioNJ, optimize tree topology. The numbers on the branches indicate the fraction of bootstrap iterations supporting each node. The accession numbers of the proteins used for the preparation of this tree and the organism names are listed in Table 2 hereinbelow; the tree is presented in FIG. 12.

TABLE 2

Accession numbers of the sequences used for the construction of the phylogenetic tree

Figure 12:
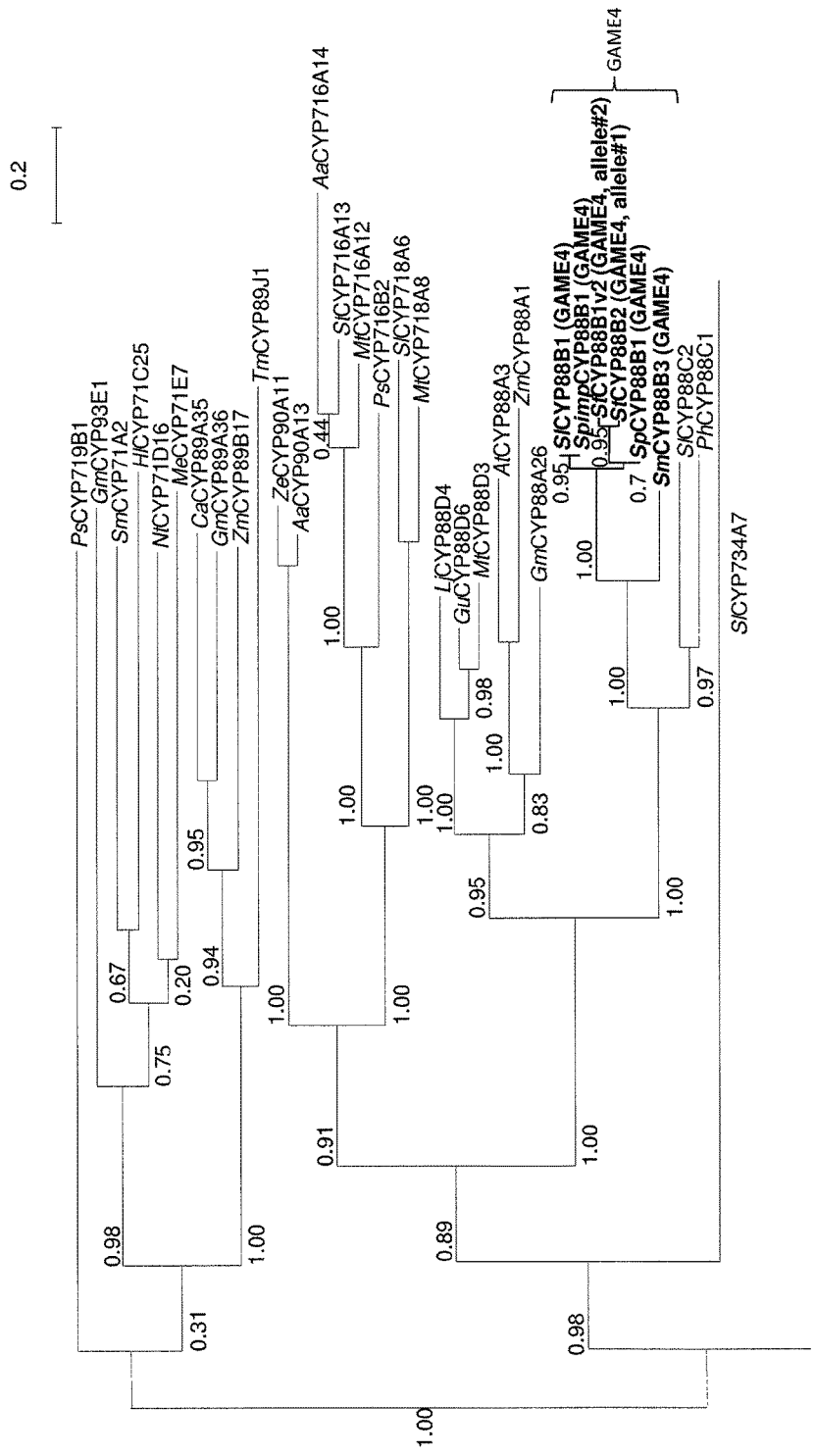
FIG. 12 shows the phylogenetic tree of GAME genes in the plant CYP450 protein family. The numbers on the branches indicate the fraction of bootstrap iterations supporting each node.
Figure 12:
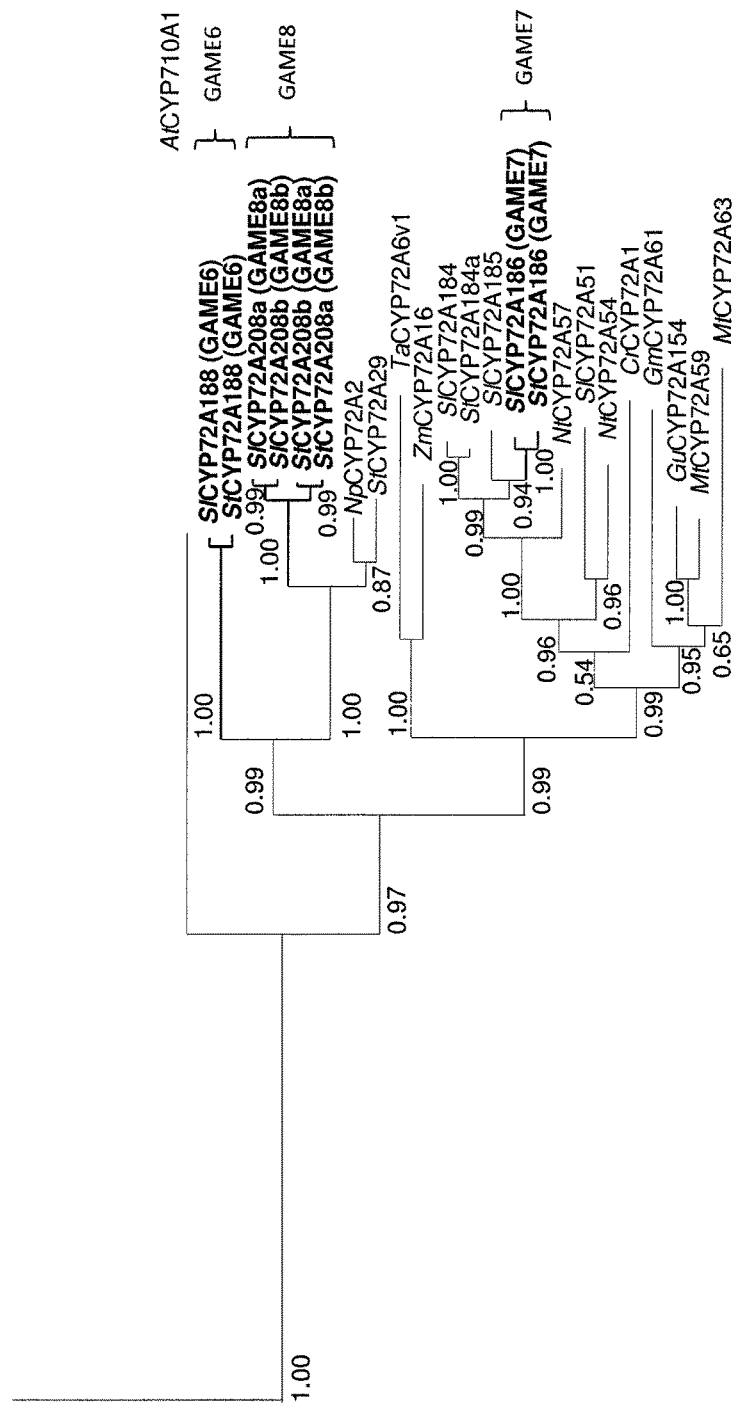

| Name as appears in FIG. 12 | Latin and common name | Accession number |
|---|---|---|
| GuCYP88D6 | Glycyrrhiza uralensis | BAG68929.1 |
| LjCYP88D4 | Lotus japonicus | BAG68927.1 |
| MtCYP88D3 | Medicago truncatula | BAG68926.1 |
| CmCYP88A2 | Cucurbita maxima | AF212991 |
| AtCYP88A3 | Arabidopsis thaliana | AAB71462.1 |
| PsCYP88A7 | Pisum sativum | AA023064.1 |
| ZmCYP88A1 | Zea mays | NP_001105586.1 |
| GmCYP88A26 | Glycine max | XP_003516638.1 |
| CaCYP89A35 | Capsicum annuum | DQ114394 |
| GmCYP89A36 | Glycine max | DQ340245 |
| ZmCYP89B17 | Zea mays | CO465851.1 |
| TmCYP89J1 | Triticum monococcum | AY914081 |
| SlCYP88B1 (GAME4) | Solanum lycopersicum | Solyc12g006460.1.1 |
| SpimpCYP88B1 (GAME4) | Solanum pimpinellifolium | contig 6356779 |
| SpCYP88B1 (GAME4) | Solanum pinelii | AW618484.1, BG135958.1 |
| StCYP88B2 (GAME4) | Solanum tuberosum group Phureja | PGSC0003DMP400041994 |
| StCYP88B1v2 (GAME4) | Solanum tuberosum group Tuberosum | PGSC0003DMP400041994 |
| SlCYP88C2 | Solanum lycopersicum | Solyc10g007860.2.1 |
| SmCYP88B3 (GAME4) | Solanum melongena | FS071104, FS071103 |
| OsCYP90A3 | Oryza sativa | AC123526.1 |
| SlCYP90A5 | Solanum lycopersicum | Solyc06g051750.2.1 |
| ScCYP90A8 | Citrus sinensis | DQ001728.1 |
| ZeCYP90A11 | Zinnia elegans | BAE16977.1 |
| PhCYP88C1 | Petunia hybrida | AAZ39647.1 |
| AaCYP90A13 | Artemisia annua | ABC94481.1 |
| AtCYP710A1 | Arabidopsis thaliana | AAC26690.1 |
| SmCYP71A2 | Solanum melongena | X71654.1 |

TABLE 2-continued

Accession numbers of the sequences used for the construction of the phylogenetic tree

| Name as appears in FIG. 12 | Latin and common name | Accession number |
|---|---|---|
| GmCYP93E1 | Glycine max | AB231332 |
| HlCYP71C25 | Hordeum lechleri | AY462228 |
| NtCYP71D16 | Nicotiana tabacum | AF166332 |
| MeCYP71E7 | Manihot esculenta | AY217351 |
| TaCYP71F1 | Triticum aestivum | AB036772 |
| AoCYP71J1 | Asparagus officinalis | AB052131 |
| MaCYP71N1 v2 | Musa acuminata | AY062167 |
| TaCYP72A6v1 | Triticum aestivum | AF123604 |
| ZmCYP72A16 | Zea mays | AF465265 |
| LeCYP72A51 | Solanum lycopersicum | Solyc10g051020.1.1 |
| GmCYP72A61 | Glycine max | DQ340241 |
| MtCYP716A12 | Medicago truncatula | ABC59076.1 |
| StCYP716A13 | Solanum tuberosum | PGSC0003DMP400013378 |
| AaCYP716A14 | Artemisia annua | DQ363134 |
| PsCYP716B2 | Picea sitchensis | AY779543 |
| SlCYP718A6 | Solanum lycopersicum | Solyc07g055970.1.1 |
| MtCYP718A8 | Medicago truncatula | XP_003617455.1 |
| PsCYP719B1 | Papaver somniferum | EF451150 |
| StCYP72A186 (GAME7) | Solanum tuberosum | PGSC0003DMG402012386 |
| SlCYP72A186 (GAME7) | Solanum lycopersicum | Solyc07g062520 |
| SlCYP72A188 (GAME6) | Solanum lycopersicum | Solyc07g043460 |
| StCYP72A188 (GAME6) | Solanum tuberosum | PGSC0003DMG400011750 |
| GuCYP72A154 | Glycyrrhiza uralensis | BAL45206.1 |
| MtCYP72A59 | Medicago truncatula | ABC59078.1 |
| NtCYP72A57 | Nicotiana tabacum | ABC69414.1 |
| NtCYP72A54 | Nicotiana tabacum | ABC69417.1 |
| CrCYP72A1 | Catharanthus roseus | gi461812 |
| MtCYP72A63 | Medicago truncatula | gi371940452 |
| NpCYP72A2 | Nicotiana plumbaginifolia | AAB05376.3 |
| SlCYP734A7 | Solanum lycopersicum | Solyc03g120060.1.1 |
| StCYP72A29 | Solanum tuberosum | BAB86912.1 |
| StSYP72a56 | Solanum tuberosum | PGSC0003DMG400017325 |
| StCYP72A208 (GAME8a) | Solanum tuberosum | PGSC0003DMG400026594 |
| StCYP72A208 (GAME8b) | Solanum tuberosum | PGSC0003DMG400026586 |
| SlCYP72A208 (GAME8a) | Solanum lycopersicum | TC243022 |
| SlCYP72A208 (GAME8b) | Solanum lycopersicum | SGN-U578058 |

Metabolite Analysis

Preparation of plant tissue extracts and profiling of semi-polar compounds (including steroidal alkaloids and steroidal saponins) by UPLC-qTOF-MS and phytosterol content of the tomato leaves were carried out as described previously (Itkin et al., 2011, supra).

Quantitative Real-Time PCR Assays

RNA was isolated and Quantitative Real-Time PCR was performed as described previously (Itkin et al., 2011, supra). In addition, the TIP41 gene (23) was used as an endogenous control for the potato samples. Oligonucleotides are listed in Table 1 hereinabove.

Production of Recombinant Enzyme

GAME2, GAME17 and GAME18 were amplified from cDNA and subcloned into pACYCDUET-1 using BamH I and Pst I (GAME2, GAME18) or BamHI and XhoI (GAME17) restriction sites, and the insert was verified by sequencing. The resulting plasmids, pAC-GAME2/17/18 were transformed to E. coli BL21 DE3. For expression of the GAME enzymes, fresh overnight cultures were diluted 1:100 in 25 ml 2xYT medium with 30 µg/ml chloramphenicol and incubated at 37° C. and 250 rpm until an $A_{600\ nm}$ of 0.4 was reached. Subsequently, IPTG was added to a concentration of 0.5 mM, and the incubation was continued overnight at 18° C. and 250 rpm. The next day, cells were harvested by centrifugation, and the pellet resuspended in 2 ml of 50 mM Tris HCl pH=7.0, 15% glycerol, 0.1 mM EDTA and 5 mM β-mercaptoethanol. After breaking the cells by sonication, insoluble material was removed by centrifugation, and the soluble fractions were used for characterization of the enzymes. Proteins were stored at −20° C. until further analysis.

Preparation of Substrates

For hydrolysis, 35 mg of α-tomatine was solved in 3 ml of 1N HCl, and was incubated for 15 min at 100° C. Subsequently, the solution was put on ice, and $NH_3$ was added until the pH of the solution was 9.0. The solution was extracted with 4 ml water-saturated butanol. The butanol phase was evaporated to dryness under vacuum, the residual pellet solved in 1 ml methanol and stored at −20° C. until further use. The degradation products of α-tomatine were separated on a Luna 5 µm C18(2) 100 Å, LC Column 150×21.2 mm (Phenomenex, USA), using an isocratic elution with 25% acetonitrile in water and 0.1% formic acid. Compounds were detected using a 3100 Mass Detector (Waters), and collected. Fractions were freeze-dried, and purity of compounds was verified by LC-MS. For identification of products, liquid chromatography, coupled to quadrupole time-of-flight mass spectrometry (LC-QTOF-MS) was performed using a Waters Alliance 2795 HPLC connected to a Waters 2996 PDA detector and subsequently a QTOF Ultima V4.00.00 mass spectrometer (Waters, MS technologies, UK) operated in positive ionization mode. The column used was an analytical Luna 3 µm C18 (2) 100 Å; 150×2.0 mm (Phenomenex, USA) attached to a C18 pre-column (2.0×4 mm; AJO-4286; Phenomenex, USA). Degassed eluent A [ultra-pure water:formic acid (1000:1, v/v)] and eluent B [acetonitrile:formic acid (1000:1, v/v)] were used with flow rate of 0.19 ml/min. The gradient started at 5% B and increased linearly to 75% B in 45 min, after which the column was washed and equilibrated for 15 min before the next injection. The injection volume was 5 μl. This procedure yielded several milligrams of pure γ-tomatine (tomatidine-galactoside-glucoside, T-Gal-Glu) and β1-tomatine (tomatidine-galactoside-diglucoside. T-Gal-Glu-Glu). Tomatidine galactoside (T-Gal) could not be purified in this way due to strong contamination with T-Gal-Glu. Therefore 5 mg tomatidine was incubated with GAME1 and UDP-galactose in 1 ml reaction mix, as described previously (Itkin et al., 2011, supra). T-Gal was purified from UDP-galactose by solid phase extraction. Waters OASIS HLB 3 cc columns (Waters Corp., Milford, Mass.) was conditioned with 6 mL 100% methanol followed by rinsing with 4 mL ultra-pure water. The reaction, supplemented with 10% methanol, was loaded and the cartridge was subsequently washed with 4 mL ultra-pure water. Compounds were eluted with 1 mL 75% methanol in ultra-pure water (v:v), and 0.4 mL 100% methanol. The solvent was removed from the combined eluate using a speed vacuum concentrator until a totally dry-pellet was obtained.

Enzyme Assays

The substrates T-Gal, β1- and γ-tomatine were dissolved to 1 mM in 50% DMSO. Enzyme assays were carried out in 50 mM Tris HCl pH=7.0 containing 5 mM β-mercaptoethanol using 5 μg/ml enzyme, 8 mM UDP-xylose and 0.02 mM substrate in a final reaction volume of 100 μl. After 2 h. of incubation under agitation at 37° C., reactions were stopped by addition of 300 μl methanol and 0.1% formic acid, and followed by brief vortexing and sonication for 15 min Subsequently, the extracts were centrifuged for 5 min at 13,000 rpm and filtered through 0.45 μm filters (Minisart SRP4, Biotech GmbH, Germany), and analyzed by LC-MS (see above). The amount of product was measured by the peak surface area in the LC-MS chromatogram, and compared to a control incubation in which an enzyme preparation of an E. coli harboring an empty pACYCDUET-1. Masses used for detection were α-tomatine ($C_{50}H_{83}NO_{21}$; m/z=1034.55 ([M+H]+)), β1-tomatine T-Gal-Glu-Glu ($C_{45}H_{75}NO_{17}$; m/z=902.51 ([M+H])), β2-tomatine ($C_{44}H_{73}NO_{16}$; m/z=872.50 ([M+H]+)), γ-tomatine T-Gal-Glu ($C_{39}H_{65}NO_{12}$; m/z=740.46 ([M+H])), and T-Gal ($C_{33}H_{55}NO_{7}$; m/z=578.41 ([M+H])).

Virus Induced Gene Silencing (VIGS) Experiments

Vectors containing fragments of GAME genes were constructed and VIGS experiments were conducted as described previously (Orzaea D et al., 2009. Plant Physiol. 150:1122-1134; Li R et al., 2006 J. Mass Spec. 41:1-22). Plants infected with Agrobacterium, containing empty vector and helper vector pTRV1, were used as control. Oligonucleotides used to prepare the pTRV2_DR_GW vectors are listed in Table 1 hereinabove.

Genome Sequence Analysis of the Wild Tomato Species

Partial genomic data obtained by re-sequencing (Dr. Arnaud G. Bovy, unpublished data) of three tomato wild species genomes (i.e. Solanum pennellii, S. pimpinellifolium and S. chmielewskii) were analyzed for the presence or absence of sequences (contigs) that align to the SGAs biosynthesis gene clusters on tomato chromosomes 7 and 12. The TopHat toolkit (Trapnell C. 2012. Nat. Protoc. 7:562-578) was used for mapping reads of the wild species to the tomato genome (ITAG 2.4), as a reference genome. The mapped reads were visualized with the IGV genome browser (Robinson J T et al., 2011. Nat. Biotechnol. 29:24-26). In order to assemble and align the sequence of the contigs from the three wild species to the gene clusters on to the existing cultivated tomato sequences of chromosomes 7 and 12, a combination of the CLC workbench, CAP3 BWA and SAMtools software packages and an in-house Perl script were used.

Example 1: Genes Associated with SGA Biosynthesis

To discover genes associated with SGA biosynthesis, a co-expression analysis using transcriptome data from tomato and potato plants was performed. Coexpression with GAME1/SGT1 (chromosome 7) and GAME4 (chromosome 12) as "baits" in either potato or tomato are presented in a form of a heatmap in Table 3-6 herein below. Genes that are highly co-expressed with either GAME1/SGT1 (chromosome 7) or GAME4 (chromosome 12) are depicted with a large font and bold.

TABLE 3

Accession numbers, putative protein and co-expression r-values-tomato, chromosome 7

| Gene name | Putative protein | r-value of correlation with tomato GAME1 expression |
|---|---|---|
| Solyc07g043310 | Aminotransferase | −0.26 |
| Solyc07g043320 | Unknown Protein | 0.12 |
| Solyc07g043330 | GRAS family transcription factor | 0.72 |
| Solyc07g043340 | Unknown Protein | |
| Solyc07g043350 | Unknown Protein | |
| Solyc07g043360 | 60S ribosomal protein L27 | 0.10 |
| Solyc07g043370 | Transposase | |
| Solyc07g043380 | Unknown Protein | |
| Solyc07g043390 | Cellulose synthase family protein | 0.92 |
| Solyc07g043400 | Unknown Protein | |
| Solyc07g043410 | UDP-xylose xylosyltransferase (GAME2) | |
| Solyc07g043420 | 2-oxoglutarate-dependent dioxygenase | 0.79 |
| Solyc07g043430 | Gag-Pol polyprotein | |
| Solyc07g043440 | Glucosyltransferase-like protein | |
| Solyc07g043450 | Zeatin O-glucosyltransferase | |
| Solyc07g043460 | Cytochrome P450 (GAME 6) | 0.91 |
| Solyc07g043470 | Unknown Protein | |
| Solyc07g043480 | UDP-glucose glucosyltransferase | 0.88 |
| Solyc07g043490 | UDP-glucosyltransferase family 1 protein (GAME1) | 1.00 |
| Solyc07g043500 | UDP-glucosyltransferase | 0.95 |
| Solyc07g043510 | Cysteine-type peptidase | −0.24 |
| Solyc07g043520 | transposase | |
| Solyc07g043530 | Unknown Protein | |
| Solyc07g043540 | Unknown Protein | |
| Solyc07g043550 | UDP-arabinose 4-epimerase | 0.70 |
| Solyc07g043560 | Heat shock protein 4 | 0.24 |
| Solyc07g043570 | Aldo/keto reductase family protein | −0.09 |
| Solyc07g043580 | BHLH transcription factor | 0.43 |
| Solyc07g043590 | Amine oxidase family protein | 0.03 |
| Solyc07g043600 | Pentatricopeptide repeat-containing protein | 0.43 |
| Solyc07g043610 | Auxin response factor 6 | |
| Solyc07g043620 | Auxin response factor 6-1 | 0.65 |
| Solyc07g043630 | Acyl-CoA synthetase/AMP-acid ligase II | |
| Solyc07g043640 | Acyl-CoA synthetase/AMP-acid ligase II | |
| Solyc07g043650 | AMP-dependent synthetase and ligase | |
| Solyc07g043660 | Acyl-CoA synthetase/AMP-acid ligase II | −0.16 |
| Solyc07g043670 | Hydroxycinnamoyl CoA quinate transferase 2 | |

TABLE 3-continued

Accession numbers, putative protein and co-expression r-values-tomato, chromosome 7

| Gene name | Putative protein | r-value of correlation with tomato GAME1 expression |
|---|---|---|
| Solyc07g043680 | Enoyl-CoA-hydratase | |
| Solyc07g043690 | Enoyl-CoA-hydratase | |
| Solyc07g043700 | Acyltransferase | |

TABLE 4

Accession numbers, putative protein and co-expression r-values-potato, chromosome 7

| Gene name | Putative protein | r-value of correlation with potato SGT1 expression |
|---|---|---|
| PGSC0003DMG400011754 | Gamma aminobutyrate transaminase | −0.31 |
| PGSC0003DMG400011753 | Uro-adherence factor A | −0.40 |
| PGSC0003DMG400011742 | DELLA protein RGA | 0.15 |
| PGSC0003DMG400011741 | 60S ribosomal protein L27 | 0.43 |
| PGSC0003DMG400039612 | Conserved gene of unknown function | |
| PGSC0003DMG400011752 | Cellulose synthase | 0.90 |
| PGSC0003DMG400011740 | beta-solanine rhamnosyltransferase (SGT3) | 0.90 |
| PGSC0003DMG400011751 | 2-oxoglutarate-dependent dioxygenase | 0.87 |
| PGSC0003DMG400011750 | Cytochrome P-450 (GAME 6) | 0.92 |
| PGSC0003DMG400044993 | Unknown Protein | |
| PGSC0003DMG400011749 | solanidine galactosyltransferase (SGT1) | 1.00 |
| PGSC0003DMG402015928 | OTU-like cysteine protease family protein | −0.24 |
| PGSC0003DMG401015928 | Conserved protein of unknown function | −0.25 |
| PGSC0003DMG400015927 | UDP-arabinose 4-epimerase 1 | −0.21 |
| PGSC0003DMG400015920 | Heat shock 70 kDa protein | −0.17 |
| PGSC0003DMG402015926 | Aldo/keto reductase | −0.05 |
| PGSC0003DMG401015926 | Isoform 2 of Transcription factor PIF5 | −0.33 |
| PGSC0003DMG400015925 | Amine oxidase | 0.11 |
| PGSC0003DMG400015924 | Pentatricopeptide repeat-containing protein | 0.32 |
| PGSC0003DMG400015919 | ARF8 | 0.07 |
| PGSC0003DMG400036440 | AMP dependent ligase | |
| PGSC0003DMG400015923 | Acyl:coA ligase acetate-coA synthetase | |
| PGSC0003DMG400015922 | Acyl:coA ligase acetate-coA synthetase | |
| PGSC0003DMG400044288 | Acyltransferase | |
| PGSC0003DMG400015918 | Acyltransferase | 0.03 |

TABLE 5

Accession numbers, putative protein and co-expression r-values-tomato, chromosome 12

| Gene name | Putative protein | r-value of correlation with tomato GAME4 expression |
|---|---|---|
| Solyc12g006530 | Cycloartenol synthase | 0.08 |
| Solyc12g006520 | Cycloartenol synthase | 0.05 |
| Solyc12g006510 | Cycloartenol Synthase | −0.12 |
| Solyc12g006500 | Phosphate translocator protein | 0.15 |
| Solyc12g006490 | Beta-1-3-galactosyl-o-glycosyl-glycoprotein | 0.03 |
| Solyc12g006480 | Nup205 protein | 0.35 |
| Solyc12g006470 | gamma-aminobutyrate Aminotransferase-like protein | 0.94 |
| Solyc12g006460 | Cytochrome P450 (GAME 4) | 1.00 |
| Solyc12g006450 | gamma-aminobutyrate Aminotransferase-like protein | −0.13 |
| Solyc12g006440 | Unknown Protein | 0.25 |
| Solyc12g006430 | UDP-glucuronosyltransferase 1-1 82A1 | |
| Solyc12g006420 | Topoisomerase II-associated protein PAT1 | 0.08 |
| Solyc12g006410 | UDP-arabinse 4-epimerase | |
| Solyc12g006400 | Unknown Protein | |
| Solyc12g006390 | 2-oxoglutarate-dependent dioxygenase | |
| Solyc12g006380 | 2-oxoglutarate-dependent dioxygenase | 0.15 |
| Solyc12g006370 | Amine oxidase family protein | −0.16 |
| Solyc12g006360 | Multidrug resistance protein mdtK | |
| Solyc12g006350 | Auxin response factor 6 | 0.35 |
| Solyc12g006340 | Auxin response factor 6 | 0.47 |

TABLE 5-continued

Accession numbers, putative protein and co-expression r-values-tomato, chromosome 12

| Gene name | Putative protein | r-value of correlation with tomato GAME4 expression |
|---|---|---|
| Solyc12g006330 | Acyltransferase-like protein | |
| Solyc12g006320 | ATP-dependent RNA helicase | 0.14 |
| Solyc12g006310 | Endoplasmic reticulum-Golgi | 0.25 |
| Solyc12g006300 | WD-repeat protein-like | −0.03 |
| Solyc12g006290 | Reticulon family protein | 0.19 |
| Solyc12g006280 | Myb-like DNA-binding protein | |

TABLE 6

Accession numbers, putative protein and co-expression r-values-potato, chromosome 12

| Gene name | Putative protein | r-value of correlation with potato GAME4 expression |
|---|---|---|
| PGSC0003DMG400020034 | Beta-amyrin synthase | −0.13 |
| PGSC0003DMG400024276 | Beta-Amyrin Synthase | −0.09 |
| PGSC0003DMG400024277 | Gene of unknown function | 0.10 |
| PGSC0003DMG400024278 | Phenylacetaldehyde synthase | 0.10 |
| PGSC0003DMG400024279 | Conserved gene of unknown function | −0.16 |
| PGSC0003DMG400024280 | Triose phosphate/phosphate translocator, non-green plastid, chloroplast | −0.06 |
| PGSC0003DMG400024271 | Acetylglucosaminyltransferase | −0.06 |
| PGSC0003DMG400024273 | Resistance protein PSH-RGH6 | 0.37 |
| PGSC0003DMG400024281 | Gamma aminobutyrate transaminase isoform2 | 0.94 |
| PGSC0003DMG400024274 | Cytochrome P450 monooxygenase GAME4 | 1.00 |
| PGSC0003DMG400024275 | Gamma aminobutyrate transaminase isoform3 | 0.37 |
| PGSC0003DMG400024282 | Fortune-1 | 0.36 |
| PGSC0003DMG400028806 | UDP-glycosyltransferase 82A1-like Topoisomerase II-associated | −0.18 |
| PGSC0003DMG401028807 | protein PATI | |
| PGSC0003DMG402028807 | UDP-arabinse 4-epimerase | |
| PGSC0003DMG400028824 | Gene of unknown function | |
| PGSC0003DMG400028808 | 2-oxoglutarate-dependent dioxygenase | −0.07 |
| PGSC0003DMG400028809 | 2-oxoglutarate-dependent dioxygenase | 0.61 |
| PGSC0003DMG400028810 | Amine oxidase | −0.04 |
| PGSC0003DMG400028825 | MATE transporter | |
| PGSC0003DMG400028826 | Auxin response factor 6 | |
| PGSC0003DMG400043090 | Integrase core domain containing protein 27 | |
| PGSC0003DMG400037700 | WRKYtranscription factor | |
| PGSC0003DMG400028811 | Acyltransferase | |
| PGSC0003DMG400028812 | DEAD-box ATP-dependent RNA helicase 53 | 0.56 |
| PGSC0003DMG400028814 | WD-repeat protein | −0.10 |
| PGSC0003DMG401028829 | Polygalacturonase | |
| PGSC0003DMG400028815 | Reticulon family protein | 0.08 |
| PGSC0003DMG400028830 | Myb-like DNA-binding domain, SHAQKYF class family protein | |

Figure 2:
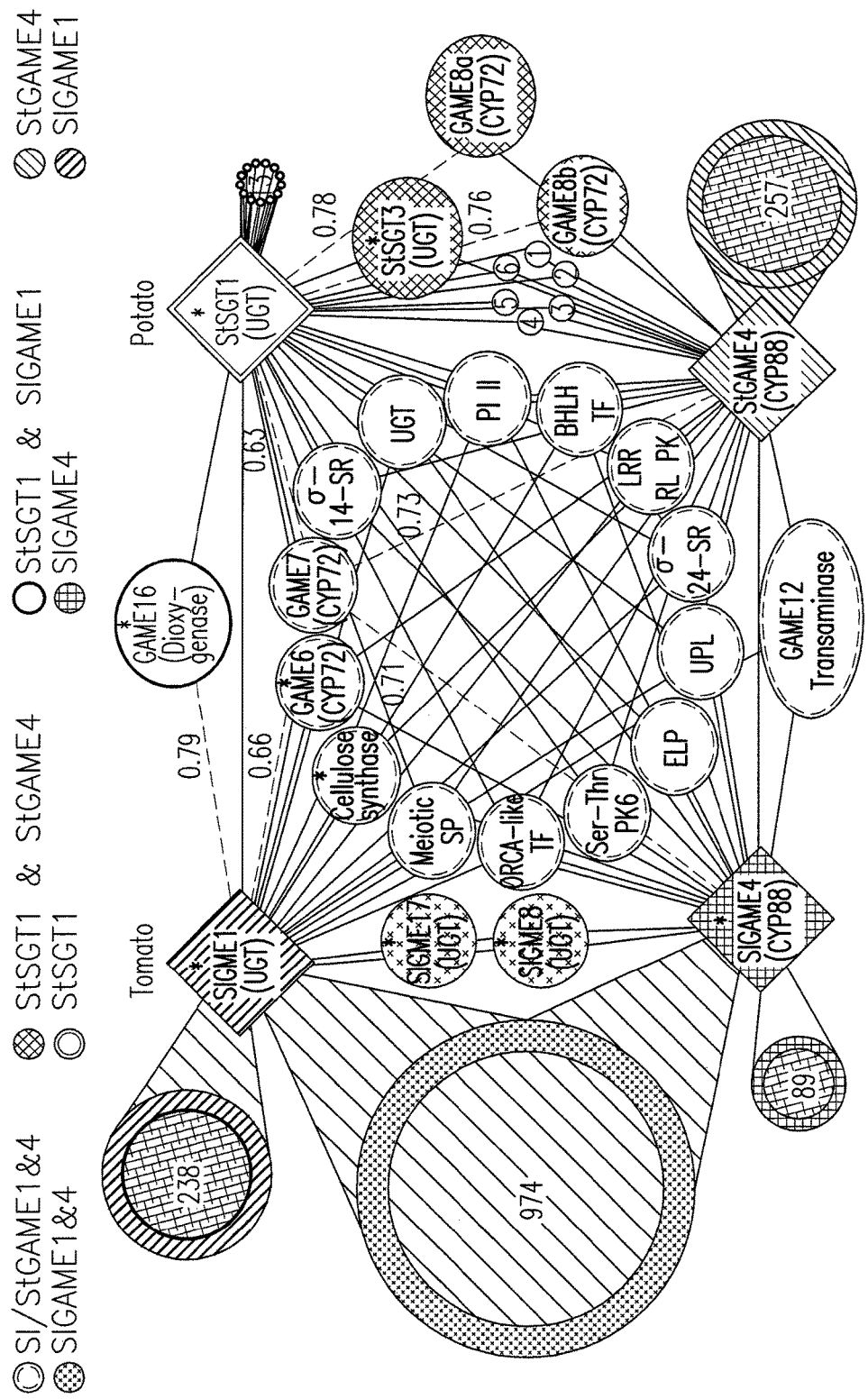
Figure 3:
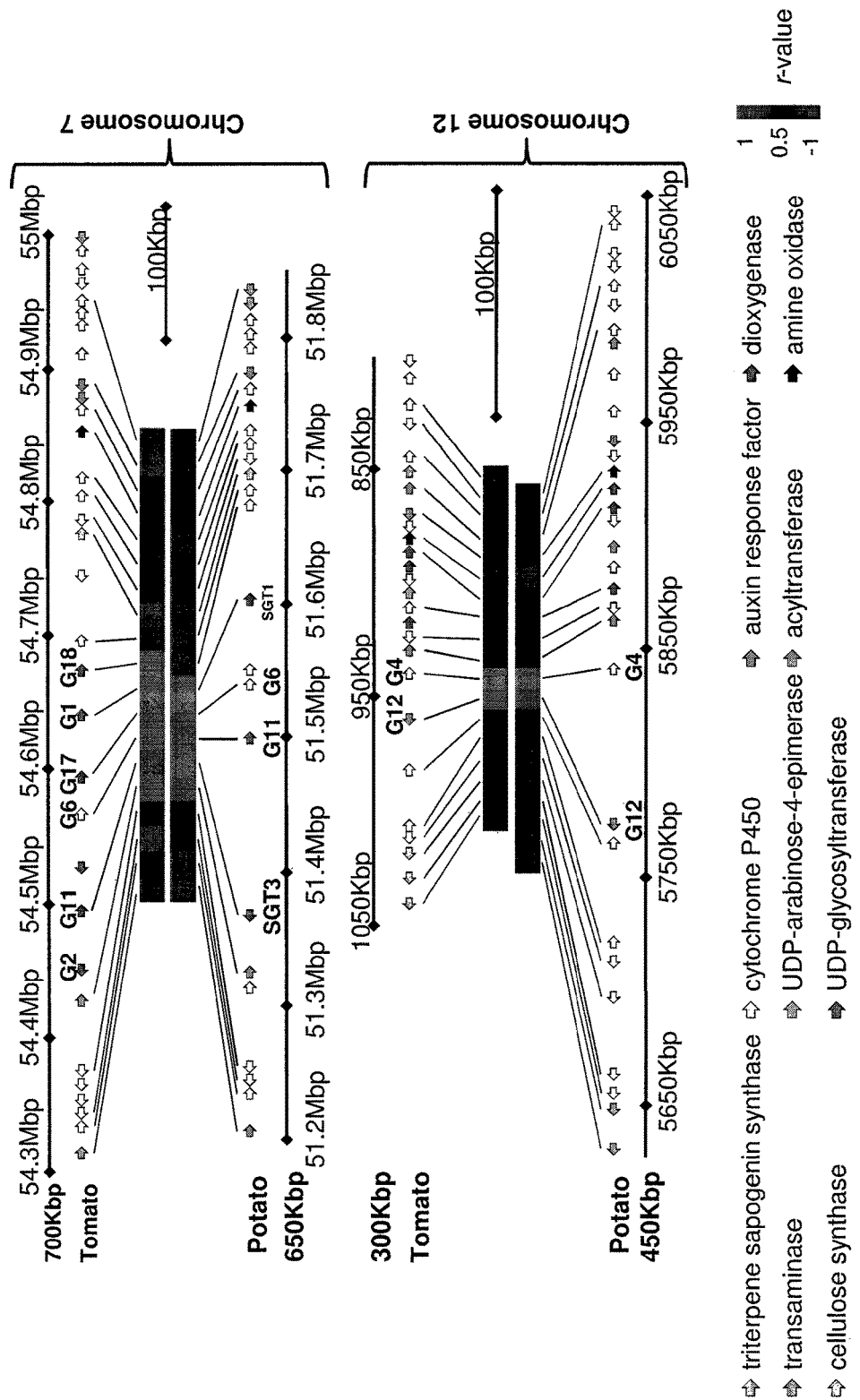
FIG. 3 presents schematic map of genes identified in the duplicated genomic regions in tomato and potato and their coexpression. Coexpression with GAME1/SGT1 (chromosome 7) and GAME4 (chromosome 12) as baits in either potato or tomato are presented in a form of a heatmap (Tables 3-6). Specific gene families are indicated by dark arrows while members of other gene families are in white arrows.

Sixteen genes from each species were co-expressed with GAME1/SGT1 (Table 7, FIG. 2). One of these genes, previously designated GLYCOALKALOID METABOLISM 4 (GAME4), encodes a member of the 88D subfamily of cytochrome P450 proteins (FIG. 3). GAME4 and GAME1/SGT1 display a very similar expression profile in tomato and potato ((WO 2010/095843). The GAME1/SGT1 and GAME4 genes in tomato and potato are positioned in chromosomes 7 and 12 such that they are physically next to several of their co-expressed genes (FIG. 2).

Figure 4A:
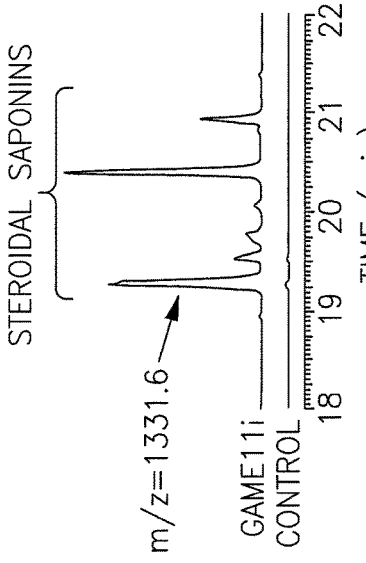
FIG. 4 shows functional analysis of tomato GAME genes. (4A) GAME8-silenced transgenic (RNAi) leaves accumulated 22-(R)-hydroxycholesterol compared to wild type. (4B) An array of cholestanol-type steroidal saponins (STSs) accumulates in GAME11 VIGS-silenced leaves. (4C) An STS (m/z=753.4) accumulates in GAME12 VIGS-leaves. (4D) Tomatidine, the steroidal alkaloid aglycone, accumulates in GAME1-silenced transgenic leaves. (4E to 4H) Enzyme activity assays of the 4 recombinant tomato GAME glycosyltransferases.
Figure 4B:
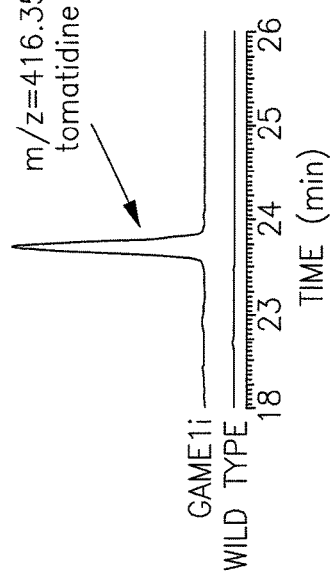
Figure 4C:
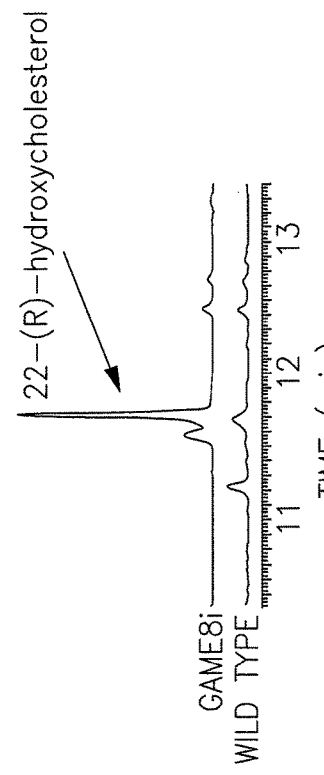

A cluster of GAME1/SGT1 co-expressed genes spans a ~200Kbp genomic region on chromosome seven. Together with GAME1, the tomato cluster is composed of 7 co-expressed genes. These include 3 UDP-glycosyltransferases [GAME2 (termed SGT3 in potato); GAME17 and GAME18], a cytochrome P450 of the 72A subfamily (GAME6), a 2-oxoglutarate-dependent dioxygenase (GAME11), and a cellulose synthase-like protein. It appears that in potato this cluster contains 5 co-expressed genes as it lacks homologs of the tomato genes encoding GAME17 and GAME18 UDP-glycosyltransferases. Enzyme activity assays were performed with the four recombinant clustered tomato UDP-glycosyltransferases. GAME17 and GAME18 exhibited UDP-glucosyltransferase activity when incubated with tomatidine galactoside (T-Gal) and γ-tomatine (T-Gal-Glu) as a substrate, respectively, whereas GAME2 was shown to have an UDP-xylosyltransferase activity when incubated with β1-tomatine (T-Gal-Glu-Glu) as a substrate (FIG. 4, E to G). GAME1 was previously shown to act as a tomatidine UDP-galactosyltransferase in tomato (Itkin et al., 2011, supra). When incubating the 4 recombinant UGT enzymes in a single test tube, with tomatidine, and all glycoside donors (UDP-galactose, -glucose and -xylose), the accumulation of the final SGA product α-tomatine was observed (FIG. 4H).

Two genes encoding putative transcription factors were identified among the genes co-expressed with GAME1/SGT1 and GAME4 (FIG. 4): one gene, designated GAME9, was identified by the tomato ID Solyc01g090340 and by the potato ID PGSC0003DMG400025989. It is described as ethylene-responsive element binding factor 13, and contains a putative AP2 domain. The other gene is the BHLH-transcription factor, identified by the tomato ID Solyc03g046570 and by the potato ID PGSC0003DMG400012262.

TABLE 7

Details of homologs co-expressed with known and putative steroidal alkaloid-associated genes in both potato and tomato presented in FIG. 2

| Name | Tomato ID Solyc | Potato reads | Tomato ID |
|---|---|---|---|
| Extensin-like protein | Solyc01g006400 | PGSC0003DMG400023230 | TCONS_00007692 |
| GAME 9 | Solyc01g090340 | PGSC0003DMG400025989 | TCONS_00011729 |
| Delta (24)-sterol reductase-like | Solyc02g069490 | PGSC0003DMG400021142 | TCONS_00044548 |
| BHLH transcription factor | Solyc03g04657 | PGSC0003DMG400012262 | TCONS_00055879 |
| LRR receptor-like protein kinase | Solyc05g009100 | PGSC0003DMG400014576 | TCONS_00101281 |
| Glycosyltransferase | Solyc05g053120 | PGSC0003DMG402027210 | TCONS_00100675 |
| Cellulose synthase-like | Solyc07g043390 | PGSC0003DMG400011752 | TCONS_00135034 |
| GAME6 (CYP72) | Solyc07g043460 | PGSC0003DMG400011750 | TCONS_00137734 |
| GAME1 (Galactosyltransferase) | Solyc07g043490 | PGSC0003DMG400011749 | TCONS_00133014 |
| GAME7 (CYP72) | Solyc07g062520 (GAME+ r-value 0.66; GAME4 r-value 0.71) | PGSC0003DMG402012386 (SGT1 r-value 0.63; GAME4 r-value 0.73) | TCONS_00132326 |
| Srt/Thr protein kinase 6 | Solyc08g066050 | PGSC0003DMG400025461 | TCONS_00151251 |
| Meiotic serine proteinase | Solyc08g077860 | PGSC0003DMG401012339 | TCONS_00149157 |
| Sterol reductase | Solyc09g009040 | PGSC0003DMG400002720 | TCONS_00162820 |
| Ubiquitin protein ligase | Solyc10g008410 | PGSC0003DMG400021683 | TCONS_00183263 |
| Proteinase inhibitor II | Solyc11g020960 | PGSC0003DMG402003479 | TCONS_00194999 |
| GAME4 (CYP88) | Solyc12g006460 | PGSC0003DMG400024274 | TCONS_00210154 |
| Gamma-aminobutyrate Aminotransferase-like protein (transaminase) (GAME12) | Solyc12g006470 | PGSC0003DMG400024281 | |
| Beta-solanine rhamnosyltransferase (SGT3) | #N/A | PGSC0003DMG400011740 | |
| 2-oxoglutarate-dependent dioxygenase (GAME11) | Solyc07g043420 | PGSC0003DMG400011751 | |
| GAME18 (Glycosyltransferase) | Solyc07g043500 | #N/A | |
| GAME17 (Glycosyltransferase) | Solyc07g043480 | #N/A | |

Tomator and potato sequences were obtained from Sol Genomics Network (solgenomics.net). r-value for co-expression ≥ 0.8. TCON number, a contig reference name given by the inventors in the assembly of RNAsec data. N/A, not available.

Example 2: Functional Analysis of GAME9-Transcription Factor

GAME9-silencing (RNAi) and overexpressing (OX) constructs were created by introducing the corresponding GAME9 DNA fragments to pK7GWIWG2(II) and pJCV52 binary vectors, respectively. Transgenic tomato and potato lines transformed with the respective GAME9 silencing and overexpressing constructs were generated as previously described (Itkin et al., 2011, supra). Tissue extracts were prepared and analyzed as described in Itkin et al. (2011, supra).

The metabolic profiling of steroidal alkaloids using UPLC-TQ-MS was performed on extracts obtained from leaves and/or tubers of transgenic and wild type tomato and/or potato plants. In extract obtained from potato tuber peels of potato lines in which the gene encoding GAME9 was silenced (GAME9-RNAi lines) a reduction in α-solanine and α-chaconine was observed (FIGS. 5A and 5B, respectively). Leaves from potato GAME9-overexpression lines contained higher levels of α-solanine (FIG. 5C) and α-chaconine (FIG. 5D) compared to the wild type. A similar accumulation pattern was observed in potato leaves, having reduced amounts of α-chaconine and α-solanine in RNAi lines and increased amounts of these steroidal alkaloids in lines overexpressing the GAME9-transcription factor (FIG. 6).

In tomato, leaves extract of a line overexpressing the GAME9-transcription factor (designated 5879) contained higher levels of α-tomatine compared to its amount in leaf extract obtained from wild type plants. On the contrary, down regulation of the expression of GAME9-transcription factor (line 5871) resulted in significant reduction of α-tomatine content.

Example 3: Functional Characterization of the GAME Genes

GAME11 Silenced Plants

Virus induced gene silencing (VIGS) is a commonly used technique allowing systemic silencing of genes in various organs of the plant (Dinesh-Kumar S P et al., 2003. Methods Mol Biol 236:287-294).

Analysis of tomato leaves with VIGS-silenced GAME11, a putative dioxygenase in the cluster, revealed a significant reduction in α-tomatine levels and accumulation of several cholestanol-type steroidal saponins.

Figure 8B:
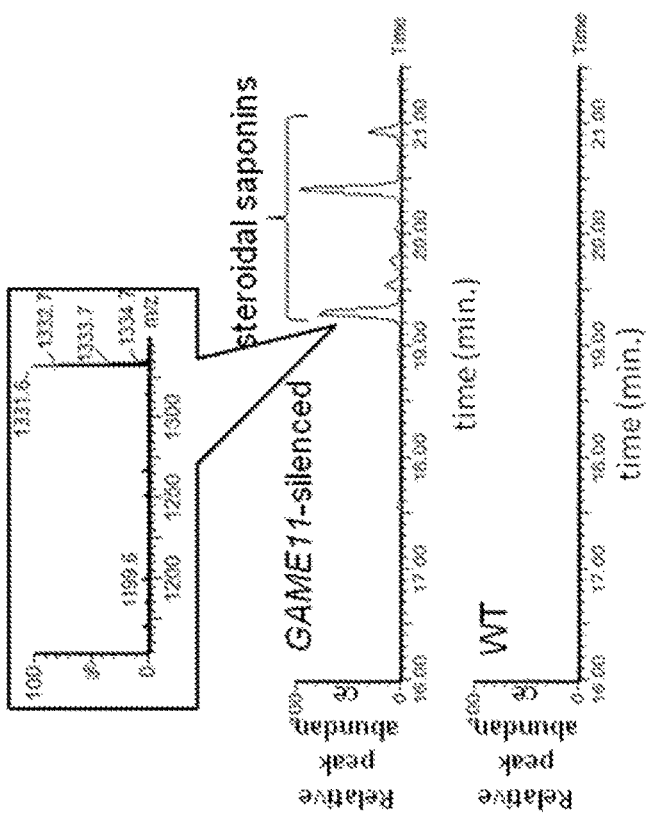
FIG. 8 shows the effect of silencing of GAME11 dioxygenase in tomato. (8A) α-tomatine levels in leaves (m/z=1034.5) (8B) cholestanol-type steroidal saponins (STS) in leaves (m/z=1331.6, 1333.6, 1199.6, 1201.6 (major saponins)). (8C) MS/MS spectrum of m/z=1331.6 (at 19.28 min) (8D) The fragmentation patterns of the saponin eluted at 19.28 min and accumulating in GAME11-silenced leaves. Corresponding mass signals are marked with an asterisk on the MS/MS chromatogram in FIG. 8C.
Figure 8A:
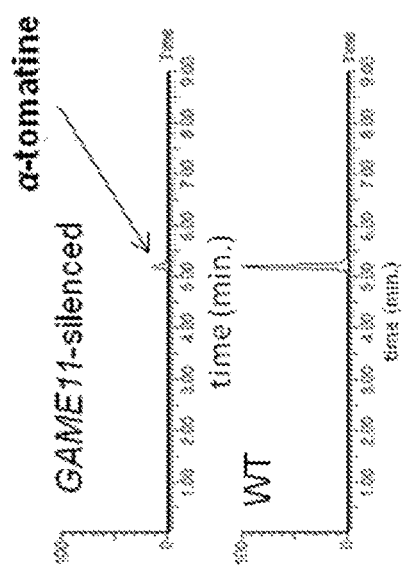
Figure 8C:
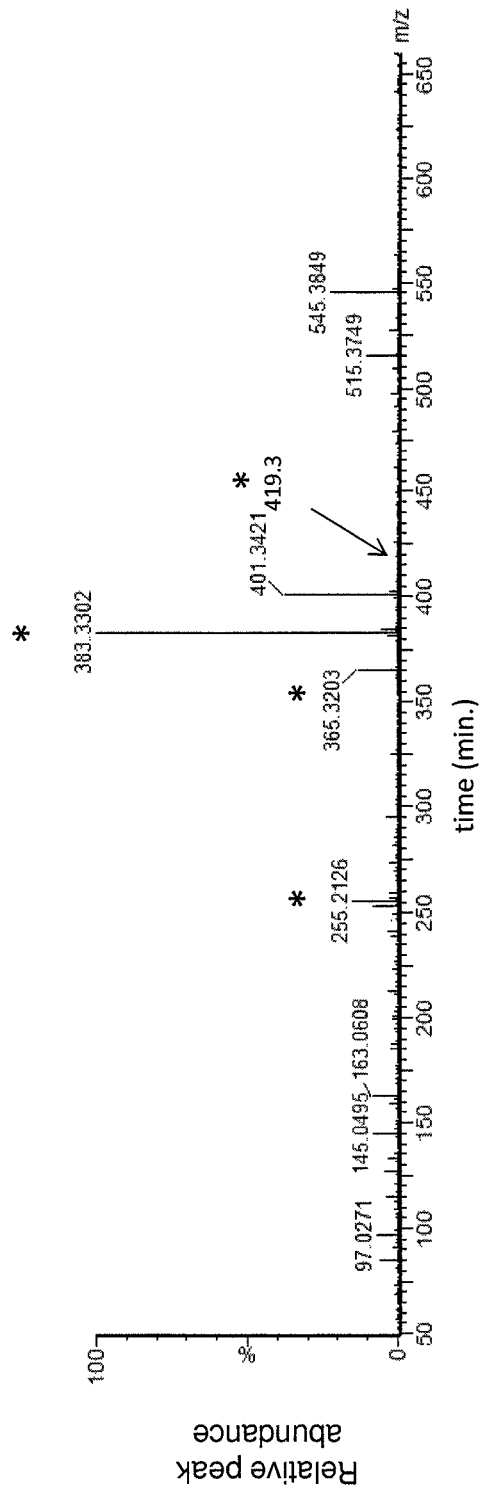
Figure 8D:
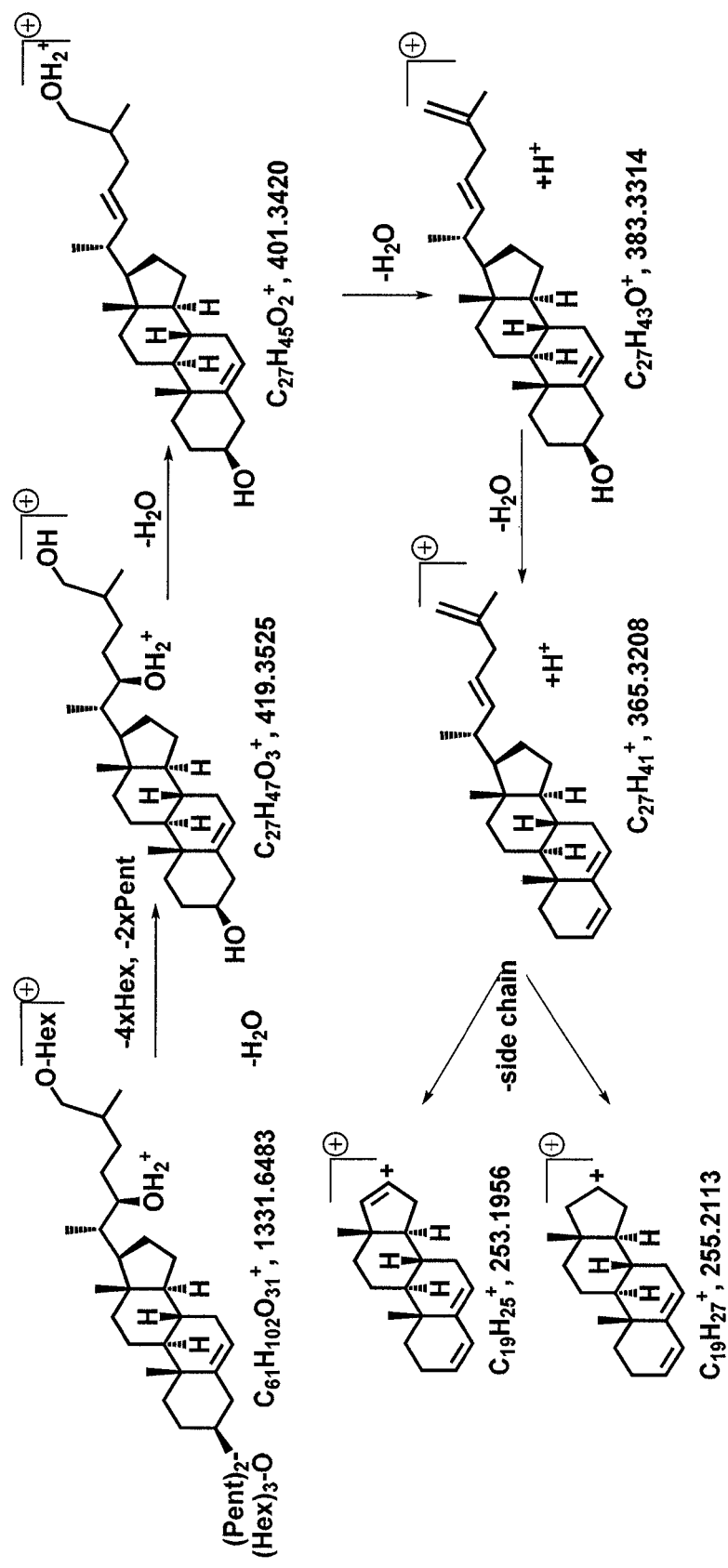

Silencing of GAME11 dioxygenase in tomato results in depletion of α-tomatine levels in leaves (m/z=1034.5) (FIG. 8A) while accumulating cholestanol-type steroidal saponins [i.e. STSs; m/z=1331.6, 1333.6, 1199.6, 1201.6 (major saponins)] (FIG. 8B). FIG. 8C shows MS/MS spectrum of m/z=1331.6 (at 19.28 min) FIG. 8D shows the fragmentation patterns of the saponin eluted at 19.28 min and accumulating in GAME11-silenced leaves. The corresponding mass signals are marked with an asterisk on the MS/MS chromatogram in FIG. 8C. The elemental composition and fragmentation patterns show that the compounds are cholestanol-type saponins, lacking one hydroxy-group and the E-ring (in comparison to furostanol-type saponins), which results in fragmentation, involving multiple losses of water molecules instead of tautomerisation and McLafferty rearrangement of the E-ring.

GAME18 Silenced Plants

The role of GAME18 in creating the tetrasaccharide moiety of α-tomatine was supported by Virus Induced Gene Silencing (VIGS) assays as GAME18-silenced fruit accumulated γ-tomatine which was not present in the control sample (FIG. 9).

Figures 9A, 9B:
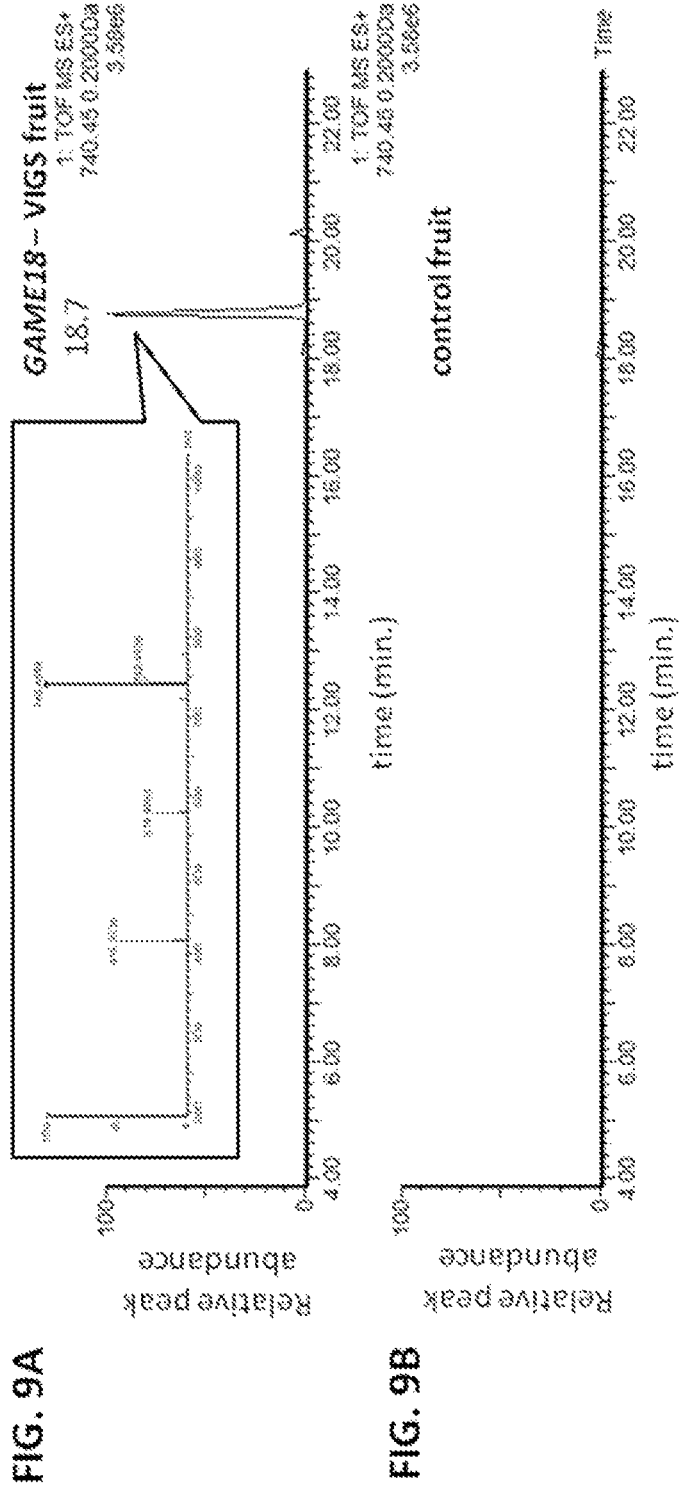
FIG. 9 shows metabolites extracted from GAME18-silenced mature green tomato fruit. Peaks of newly accumulating compounds corresponding to the γ-tomatine standard (m/z=740.5) (9A-C), and γ-tomatine pentoside (m/z=872.5) (9D-E) are shown.
Figure 9C:
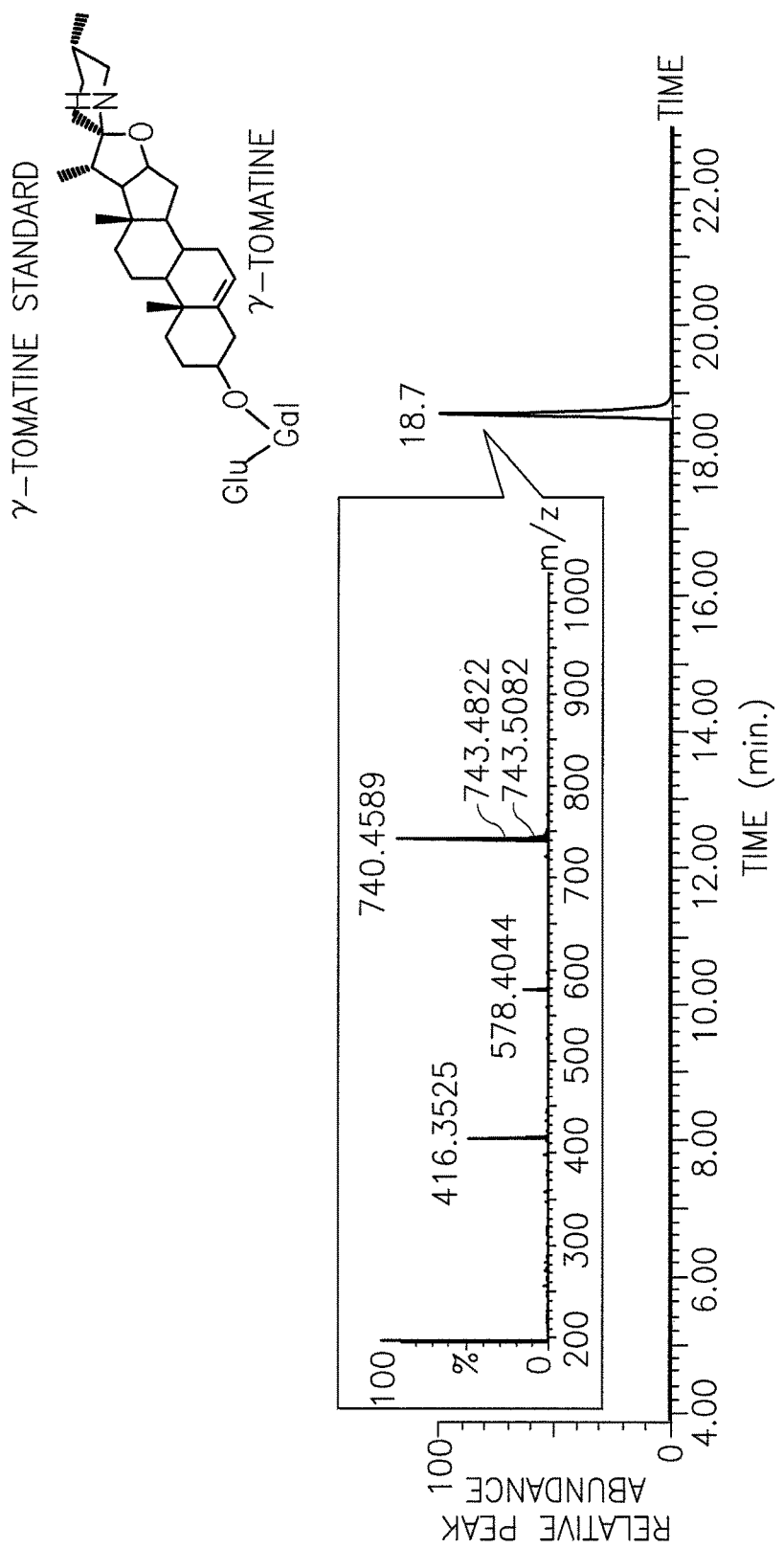
Figure 9D:
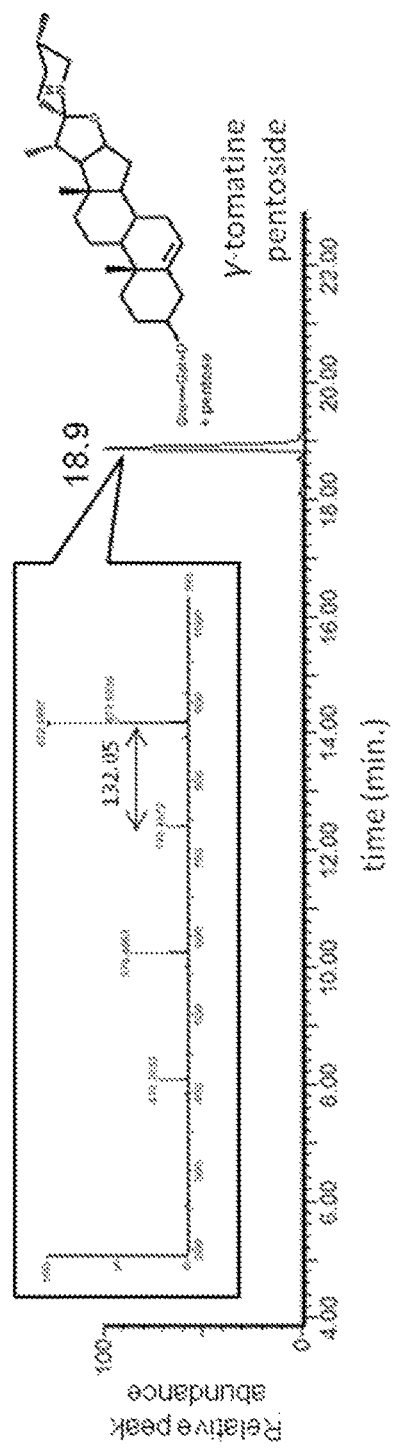

Among the metabolites extracted from GAME18-silenced mature green fruit, peaks of newly accumulating compounds were detected, corresponding to the γ-tomatine standard (m/z=740.5) (FIG. 9A-C), and γ-tomatine pentoside (m/z=872.5) (FIG. 9D-E).

GAME12 Silenced Plants

Figure 4D:
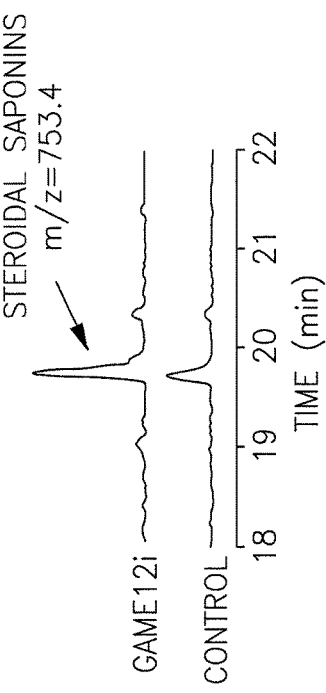
Figures 10C, 10D:
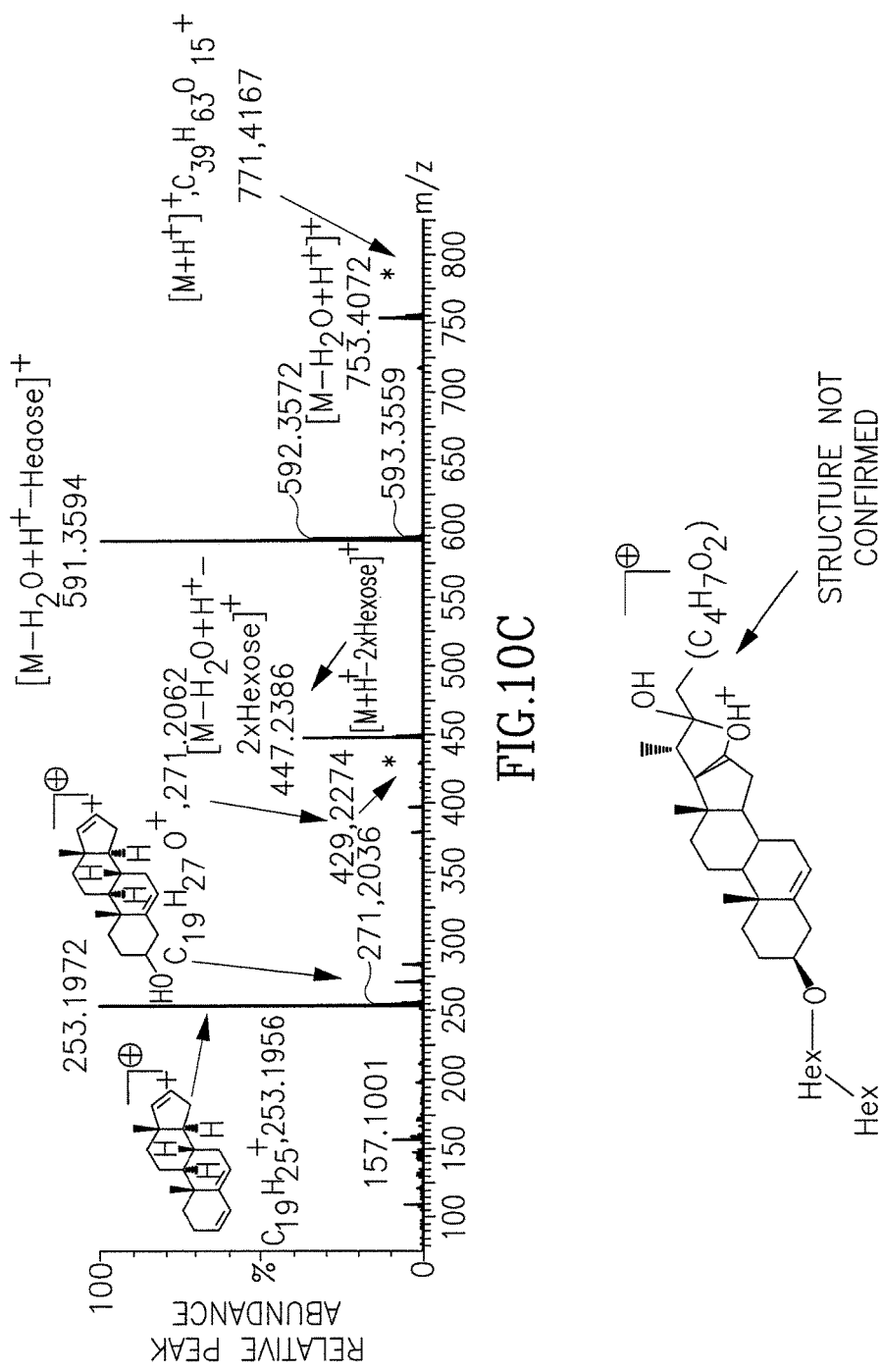
FIG. 10 shows the effect of silencing of GAME12 transaminase in tomato. (10A) accumulation of a furastanol-type STS. 10(B-C) GAME12-silenced leaves accumulate an STS (m/z=753.4), while it exists in only minor quantities in WT leaf. (10D) MS/MS spectrum of m/z=753.4 at 19.71 min with interpretation of the fragments.

Silencing of GAME12 transaminase in tomato resulted in accumulation of a furastanol-type steroidal saponin (FIG. 4D). FIG. 10A shows that GAME12-silenced leaves accumulate an STS (m/z=753.4), while it exists in only minor quantities in wild type leaf FIG. 10B. FIG. 10C shows MS/MS spectrum of m/z=753.4 at 19.71 min with interpretation of the fragments. Suggested structure of the STS at 19.71 min is depicted in FIG. 10D, concluded from the characteristic mass fragments observed in the MS/MS experiment.

Function of GAME7 and GAME8

Figure 11A:
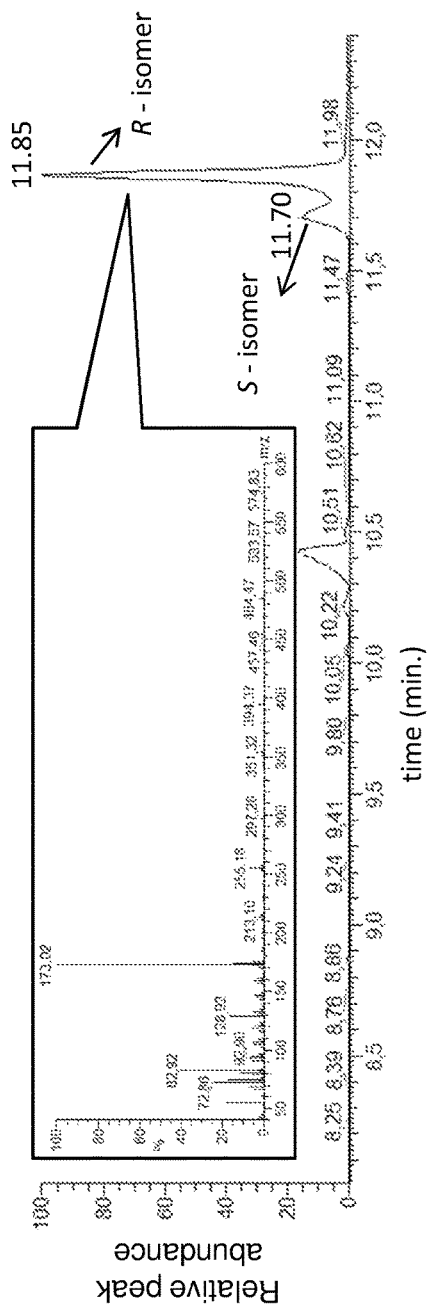
FIG. 11 shows the effect silencing of GAME8 in tomato plants. GAME8-silenced leaves accumulated 22-(S) and -(R)-cholesterol (11A). Chromatograms (mass range 172.5-173.5) acquired via EI-GC/MS, MS spectra and structures (tri-methyl-silyl derivatives) of the compounds are shown. Commercial standards of 22-(R)-(11B) and 22-(S)-cholesterol (11C) were used to verify the putative identification. (11D) GAME8-silenced line accumulates both isomers in comparison to WT (Q).
Figure 11B:
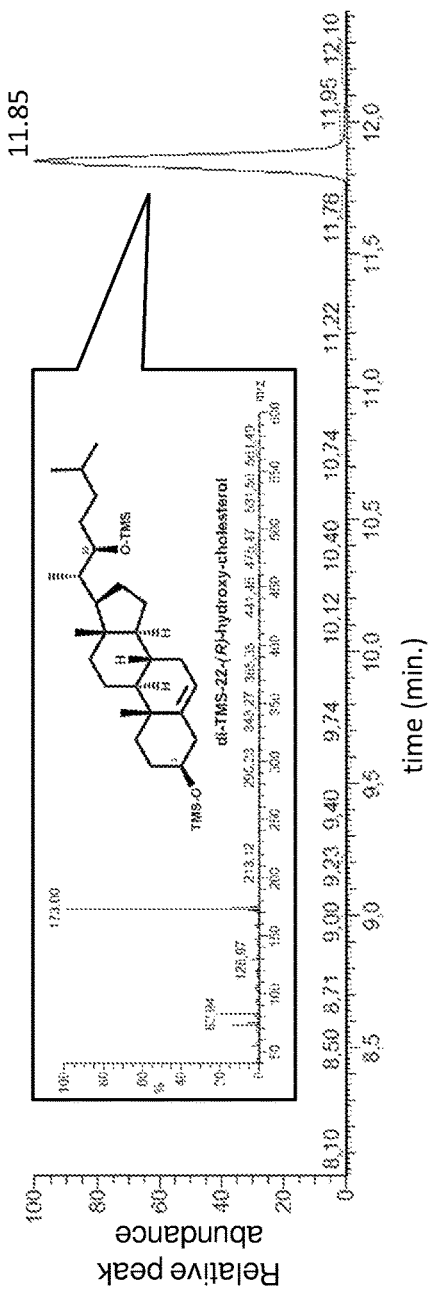
Figure 11C:
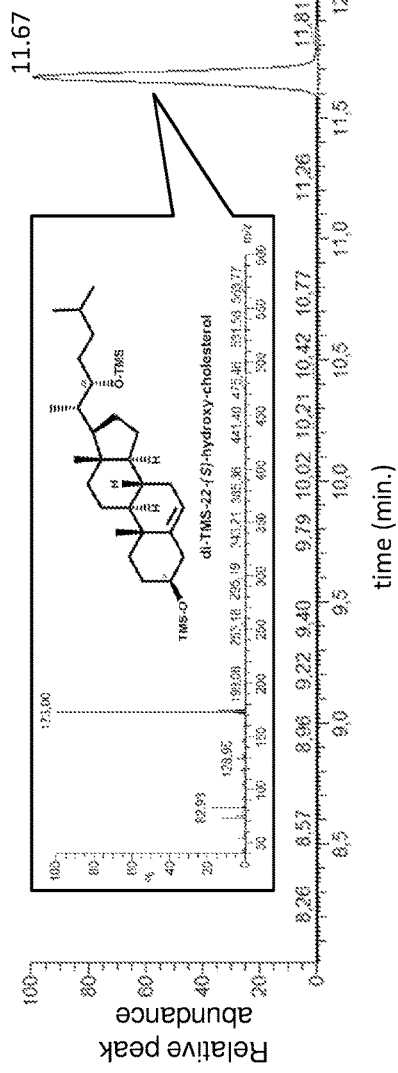
Figure 11D:
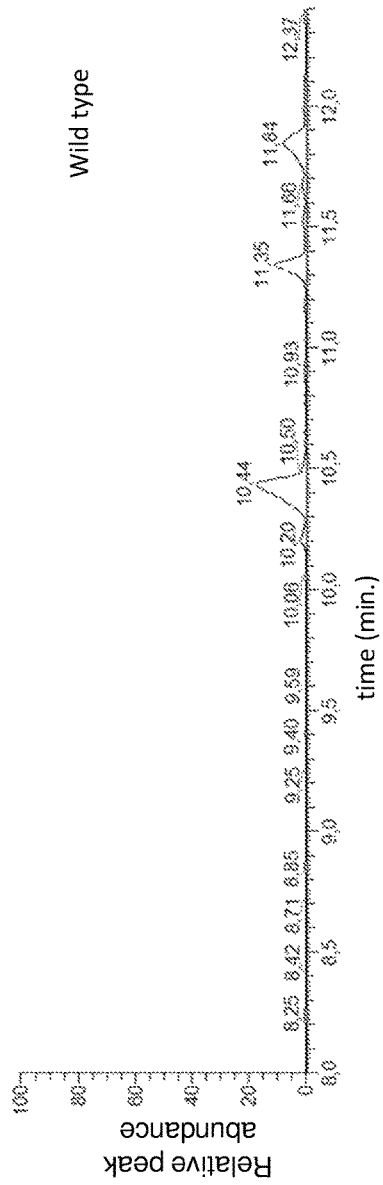

Genes that were tightly co-expressed and positioned elsewhere in the genome were also functionally examined Two genes, designated GAME7 and GAME8 belong to the CYP72 subfamily of cytochrome P450s. GAME7 was co-expressed in both species (potato and tomato) while StGAME8a and StGAME8b were strongly co-expressed with StSGT1 and StGAME4 in potato. At present, we could not demonstrate SGA-related activity for GAME7 although as for GAME6 it was suggested to be involved in SGA metabolism (US 20120159676). Yet, GAME8-silenced tomato leaves accumulated 22-(R)-hydroxycholesterol (FIG. 11A-D), a proposed intermediate in the SGA biosynthetic pathway (FIG. 1). GAME8-silenced line accumulates both isomers in comparison to wild type (FIG. 11D). The (R)-isomer is more abundant and hence most likely to be the substrate of GAME8.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A genetically modified plant comprising at least one cell having altered expression of at least one gene selected from the group consisting of a gene encoding GAME9-transcription factor and a gene encoding 2-oxoglutarate-dependent dioxygenase (GAME11), or a combination thereof, wherein the altered expression of the at least one gene or any combination thereof is elevated compared to its expression in the corresponding unmodified plant, wherein the amino acid sequence of the GAME9-transcription factor comprises the sequence set forth in SEQ ID NO:1 or the sequence at least 80% homologous to the sequence set forth in SEQ ID NO: 1, and wherein the amino acid sequence of the 2-oxoglutarate-dependent dioxygenase (GAME11) comprises the sequence set forth in any one of SEQ ID NO:7 and SEQ ID NO:8, wherein the genetically modified plant has an elevated content of at least one steroidal alkaloid or a glycosylated derivative thereof compared to a corresponding unmodified plant.

2. The genetically modified plant of claim 1, wherein the GAME9-transcription factor comprises the amino acid sequence set forth in any one of SEQ ID NO:1 and SEQ ID NO:2.

3. The genetically modified plant of claim 1, wherein the gene encoding the GAME9-transcription factor comprises the nucleic acid sequence set forth in any one of SEQ ID NO:4, and SEQ ID NO:6.

4. The genetically modified plant of claim 1, wherein the gene encoding the GAME11 dioxygenase comprises the nucleic acid sequence set forth in any one of SEQ ID NO:9, SEQ ID NO:10, SEQ ID NO:11 and SEQ ID NO:12.

5. The genetically modified plant of claim 1, wherein said plant comprises at least one cell having elevated expression of the gene encoding the GAME9-transcription factor, and the gene encoding the GAME11 dioxygenase compared to the corresponding unmodified plant.

6. The genetically modified plant of claim 1, wherein said plant is a Solanaceous crop plant.

7. A genetically modified plant comprising at least one cell having altered expression of at least one gene selected from the group consisting of a gene encoding GAME9-transcription factor and a gene encoding 2-oxogluterate-dependent dioxygenase (GAME11), or a combination thereof, wherein the said altered expression of the at least one gene or any combination thereof is inhibited expression compared to its expression in the corresponding unmodified plant, wherein the amino acid sequence of the GAME9-transcription factor comprises the sequence set forth in SEQ ID NO:1 or the sequence at least 80% homologous to the sequence set forth in SEQ ID NO: 1, and wherein the amino acid sequence of the 2-oxoglutarate-dependent dioxygenase (GAME11) comprises the sequence set forth in any one of SEQ ID NO:7 and SEQ ID NO:8, wherein said genetically modified plant comprises reduced content of at least one steroidal alkaloid or a glycosylated derivative thereof compared to said corresponding unmodified plant.

8. The genetically modified plant of claim 7, wherein said plant is a transgenic plant comprising at least one cell comprising at least one silencing molecule targeted to a gene selected from the group consisting of GAME9, or GAME11, or a combination thereof.

9. The genetically modified plant of claim 8, wherein the silencing molecule is selected from the group consisting of an RNA interference molecule and an antisense molecule, or wherein said silencing molecule is a component of a viral induced gene silencing system.

10. The genetically modified plant of claim 8, wherein the silencing molecule comprises a polynucleotide comprising nucleic acid sequence complementary to a region of the GAME9 gene or the complementary sequence thereof, wherein the nucleic acid sequence of the GAME9 gene is set forth in any one of SEQ ID NO:4 and SEQ ID NO:6.

11. The genetically modified plant of claim 10, wherein the silencing molecule is targeted to a GAME9 fragment comprising the nucleic acid sequence set forth in SEQ ID NO: 18 or the complementary sequence thereof.

12. The genetically modified plant of claim 8, wherein the silencing molecule comprises a polynucleotide having nucleic acid sequence complementary to a region of the GAME11 gene or the complementary sequence thereof, wherein the nucleic acid sequence of the GAME11 gene is set forth in any one of SEQ ID NO: 10 and SEQ ID NO:12.

13. The genetically modified plant of claim 12, wherein the silencing molecule is targeted to a GAME11 fragment comprising the nucleic acid sequence set forth in SEQ ID NO:19 or the complementary sequence thereof.

14. The genetically modified plant of claim 8, wherein said transgenic plant is a Solanaceous crop plant having reduced content of at least one steroidal glycoalkaloid selected from the group comprising α-solanine, α-chaconine, solmargine, solasonine, tomatine, tomatidine and derivatives thereof.

15. The genetically modified plant of claim 14, wherein said transgenic plant further comprises an elevated amount of at least one of steroidal saponin.

16. The genetically modified plant of claim 14, wherein said transgenic plant is a potato or an eggplant plant comprising a reduced content of at least α-solanine, α-chaconine, solmargine, and solasonine compared to a corresponding non-transgenic plant.

17. The genetically modified plant of claim 14, wherein said transgenic plant is a tomato plant comprising a reduced content of tomatine, tomatidine or derivatives thereof compared to a corresponding non-transgenic plant.

18. The genetically modified plant of claim 17, wherein said transgenic plant further comprises an elevated amount of at least one of cholestanol-type saponins.

19. The genetically modified plant of claim 1, wherein said genetically modified plant is a transgenic plant comprising at least one cell comprising at least one transcribable polynucleotide encoding at least one protein selected from the group consisting of the GAME9-transcription factor, or the 2-oxoglutarate-dependent dioxygenase (GAME11), or a combination thereof.

20. The genetically modified plant of claim 19, wherein said transgenic plant comprises a transcribable polynucleotide encoding the GAME9-transcription factor.

21. The genetically modified plant of claim 20, wherein the transcribable polynucleotide comprises the nucleic acid sequence set forth in any one of SEQ ID NO:4 and SEQ ID NO:6.

22. The genetically modified plant of claim 19, wherein said transgenic plant comprises a transcribable polynucleotide encoding the GAME11 dioxygenase.

23. The genetically modified plant of claim 22, wherein the transcribable polynucleotide comprises the nucleic acid sequence set forth in any one of SEQ ID NO:9, SEQ ID NO:10, SEQ ID NO:11 and SEQ ID NO:12.

24. The genetically modified plant of claim 1, wherein said plant is a Solanaceous crop plant having elevated content of at least one steroidal glycoalkaloid selected from the group comprising α-solanine, α-chaconine, solmargine, solasonine, tomatine, tomatidine and derivatives thereof.

25. A method of reducing the content of at least one steroidal alkaloid or a glycosylated derivative thereof in a plant, said method comprising transforming at least one plant cell with at least one silencing molecule targeted to a nucleic acid sequence encoding at least one protein selected from the group consisting of GAME9-transcription factor and 2-oxoglutarate-dependent dioxygenase (GAME11), or mutagenizing at least one gene or a combination of genes, said genes encoding at least one protein selected from the group consisting of GAME9-transcription factor and 2-oxyglutarate-dependent dioxygenase (GAME11), wherein said mutagenesis comprises introduction of one or more point mutations into said gene, or genome editing, or use of a bacterial CRISPR/CAS system, or a combination thereof, wherein the amino acid sequence of the GAME9-transcription factor comprises the sequence set forth in SEQ ID NO:1 or the sequence at least 80% homologous to the sequence set forth in SEQ ID NO: 1, and wherein the amino acid sequence of the 2-oxoglutarate-dependent dioxygenase (GAME11) comprises the sequence set forth in any one of SEQ ID NO:7 and SEQ ID NO:8, thereby producing a plant with reduced content of at least one steroidal alkaloid or a glycosylated derivative thereof compared to a corresponding non-transformed plant.

26. The genetically modified plant of claim 1, wherein the expression of the at least one gene or any combination thereof is altered, said altering comprising mutagenizing the at least one gene, wherein said mutagenesis comprises introduction of one or more point mutations, or genome editing, or use of a bacterial CRISPR/CAS system, or a combination thereof.

27. The genetically modified plant of claim 7, wherein said genetically modified plant is a transgenic plant comprising at least one cell comprising at least one transcribable polynucleotide encoding at least one protein selected from the group consisting of GAME9-transcription factor and 2-oxoglutarate-dependent dioxygenase (GAME11), or a combination thereof.

28. The genetically modified plant of claim 27, wherein said transgenic plant comprises a transcribable polynucleotide encoding the GAME9-transcription factor.

29. The genetically modified plant of claim 28, wherein the transcribable polynucleotide comprises the nucleic acid sequence set forth in any one of SEQ ID NO:4 and SEQ ID NO:6.

30. The genetically modified plant of claim 27, wherein said transgenic plant comprises a transcribable polynucleotide encoding the GAME11 dioxygenase.

31. The genetically modified plant of claim 30, wherein the transcribable polynucleotide comprises the nucleic acid sequence set forth in any one of SEQ ID NO:9, SEQ ID NO:10, SEQ ID NO:11, and SEQ ID NO:12.

32. The genetically modified plant of claim 7, wherein the expression of the at least one gene or any combination thereof is altered, said altering comprising mutagenizing the at least one gene, wherein said mutagenesis comprises introduction of one or more point mutations, or genome editing, or use of a bacterial CRISPR/CAS system, or a combination thereof.

* * * * *

SEQUENCE LISTING

```
<160> NUMBER OF SEQ ID NOS: 31

<210> SEQ ID NO 1
<211> LENGTH: 222
<212> TYPE: PRT
<213> ORGANISM: Solanum tuberosum

<400> SEQUENCE: 1

Met Asn Ile Ala Ile Asp Asp Asp Glu Ile Phe Ser Leu Pro Ser Leu
1               5                   10                  15

Asp Glu Leu Glu Ser Ile Thr His Leu Leu Tyr Asp Asp Asp Ser Asp
            20                  25                  30

Phe Phe Glu Thr Leu Ser Pro Met Ser Leu Asp Ser Thr Thr Leu Leu
        35                  40                  45

Pro Asn Asn Pro Thr Pro Asn Ser Leu Glu Ser Pro Val Arg Pro Glu
    50                  55                  60

Gly Thr Lys Glu Thr Phe Val Ala Arg Glu His Glu Glu Ser Ala Pro
65                  70                  75                  80

Gln Asp Trp Arg Arg Phe Ile Gly Val Arg Arg Arg Gln Trp Gly Thr
                85                  90                  95

Phe Ser Ala Glu Ile Arg Asp Pro Asn Arg Arg Gly Ala Arg Leu Trp
            100                 105                 110

Leu Gly Thr Tyr Glu Ser Pro Gln Asp Ala Ala Leu Ala Tyr Asp Gln
        115                 120                 125

Ala Ala Tyr Lys Ile Arg Gly Thr Lys Ala Arg Leu Asn Phe Pro Asp
    130                 135                 140

Leu Ile Gly Ser Asp Val Pro Met Pro Pro Arg Val Thr Ala Arg Arg
145                 150                 155                 160

Arg Thr Arg Ser Arg Ser Arg Ser Pro Glu Pro Ser Thr Thr Ser Ser
                165                 170                 175

Ser Ser Ser Ser Ser Ser Ser Ser Ser Ser Ser Ser Met Glu Asn
            180                 185                 190

Gly Thr Lys Lys Arg Lys Ile Asp Leu Ile Asn Ser Ile Ala Lys Ala
        195                 200                 205
```

```
Lys Leu Leu Cys Gly Val Asn Leu Gln Met Leu Ile Gln Met
    210                 215                 220
```

<210> SEQ ID NO 2
<211> LENGTH: 219
<212> TYPE: PRT
<213> ORGANISM: Solanum lycopersicum

<400> SEQUENCE: 2

```
Met Ser Ile Val Ile Asp Asp Glu Ile Phe Ser Leu Pro Ser Leu
1               5                   10                  15

Asp Glu Leu Glu Ser Ile Thr His Leu Leu Tyr Asp Asp Ser Asp
            20                  25                  30

Phe Phe Glu Thr Leu Ser Pro Met Ser Leu Asp Val Thr Thr Leu Leu
            35                  40                  45

Pro Asn Ile Pro Thr Ser Asn Ser Ile Glu Ser Pro Val Thr Pro Glu
        50                  55                  60

Glu Thr Lys Glu Pro Ser Val Ala Cys Gly Asp Ala Pro Gln Asp Trp
65                  70                  75                  80

Arg Arg Phe Ile Gly Val Arg Arg Gln Trp Gly Thr Phe Ser Ala
                85                  90                  95

Glu Ile Arg Asp Pro Asn Arg Arg Gly Ala Arg Leu Trp Leu Gly Thr
            100                 105                 110

Tyr Glu Ser Pro Arg Asp Ala Ala Leu Ala Tyr Asp Gln Ala Ala Tyr
            115                 120                 125

Lys Ile Arg Gly Thr Lys Val Arg Leu Asn Phe Pro Asp Leu Ile Gly
        130                 135                 140

Ser Asp Val Pro Met Pro Pro Arg Val Thr Ala Arg Arg Thr Arg
145                 150                 155                 160

Ser Arg Ser Arg Ser Pro Glu Pro Leu Thr Thr Ser Ser Ser Ser
                165                 170                 175

Ser Ser Ser Ser Ser Ser Ser Ser Ser Glu Asn Gly Thr Lys
            180                 185                 190

Lys Arg Lys Ile Asp Leu Ile Asn Ser Ile Ala Lys Ser Lys Leu Leu
        195                 200                 205

Cys Gly Met Asp Leu Gln Met Leu Ile Gln Met
    210                 215
```

<210> SEQ ID NO 3
<211> LENGTH: 754
<212> TYPE: DNA
<213> ORGANISM: Solanum tuberosum

<400> SEQUENCE: 3

```
gaaaatttca ttcatccaaa agaagaatga atattgcaat tgatgatgat gaaatcttct      60
ctttacctag cctcgatgaa cttgaatcta tcacacatct tctttatgat gatgattccg     120
atttttttga aactctttca ccaatgagtt tagatagcac aacattattg cctaataatc     180
ctactccaaa ttcacttgaa tcccccgtaa gaccggaggg aacaaaggaa acatttgtgg     240
cgcgcgaaca cgaagaaagc gcgccacaag attggaggcg gttcatagga gtgaggcgaa     300
ggcagtgggg cacgttttca gccgaaataa gagatccaaa taggagaggc gcgaggctgt     360
ggctaggaac ttatgagtcc ccgcaggatg cagcattggc ttatgaccaa gctgcttaca     420
agattcgggg taccaaagct cggctcaatt ttccggactt aattggctcg acgtgcctct     480
tgccaccaag agtaacggct aggcgtcgta ctcgctcacg ctcgcgctca cccgagccat     540
```

```
caacaacttc ttcgtcctca tcctcgtcct cgtcctcatc ctcgtcctcg tccatggaaa      600
atgggacgaa aaaaggaaa atagatttga taaactcaat agccaaagcc aaattactct       660
gtggtgtgaa tttacaaatg ttgatacaaa tgtgagaaaa gagcaaaggt ttattttttt      720
cttcgtttaa caattaagta ttacgtataa ttaa                                  754

<210> SEQ ID NO 4
<211> LENGTH: 754
<212> TYPE: DNA
<213> ORGANISM: Solanum tuberosum

<400> SEQUENCE: 4
gaaaatttca ttcatccaaa agaagaatga atattgcaat tgatgatgat gaaatcttct      60
ctttacctag cctcgatgaa cttgaatcta tcacacatct tctttatgat gatgattccg      120
atttttttga aactctttca ccaatgagtt tagatagcac aacattattg cctaataatc      180
ctactccaaa ttcacttgaa tcccccgtaa gaccggaggg aacaaaggaa acatttgtgg      240
cgcgcgaaca cgaagaaagc gcgccacaag attggaggcg gttcatagga gtgaggcgaa      300
ggcagtgggg cacgttttca gccgaaataa gagatccaaa taggagaggc gcgaggctgt      360
ggctaggaac ttatgagtcc ccgcaggatg cagcattggc ttatgaccaa gctgcttaca      420
agattcgggg taccaaagct cggctcaatt tccggactt aattggctcg gacgtgccta      480
tgccaccaag agtaacggct aggcgtcgta ctcgctcacg ctcgcgctca cccgagccat      540
caacaacttc ttcgtcctca tcctcgtcct cgtcctcatc ctcgtcctcg tccatggaaa      600
atgggacgaa aaaaggaaa atagatttga taaactcaat agccaaagcc aaattactct       660
gtggtgtgaa tttacaaatg ttgatacaaa tgtgagaaaa gagcaaaggt ttattttttt      720
cttcgtttaa caattaagta ttacgtataa ttaa                                  754

<210> SEQ ID NO 5
<211> LENGTH: 988
<212> TYPE: DNA
<213> ORGANISM: Solanum lycopersicum

<400> SEQUENCE: 5
taatattaca ttacattcat cacatattat tcatccaaaa caagaatgag tattgtaatt      60
gatgatgatg aaatcttctc tttacctagc cttgatgaac ttgaatccat cacacatctt      120
ctttatgacg acgattccga ttttttcgaa actctttccc caatgagttt agatgttaca      180
acattattgc ctaatattcc tacctccaat tcaattgaat cccccgtaac accggaggaa      240
acaaaagaac catctgtggc gtgtgaggac gcgccacaag attggaggcg gttcataggg      300
gtgaggcgga ggcagtgggg cacgttttca gccgaaataa gagatccaaa taggagagga      360
gcgaggctgt ggctcggaac ttatgagtcc ccgagggatg cagcattagc ttatgaccaa      420
gccgcttaca agattcgggg aaccaaagtt cggcttaatt ttcctgacct gattggctcg      480
gacgtaccta tgccacctag agtaacggct aggcgtcgta cacgctcacg ctcacgctca      540
cccgagccat taacaacttc gtcctcgtca tcctcatcat cctcgtcctc gtcctcgtcc      600
tcgtcggaaa atgaacgaa gaaaggaaa atagatttga taaactcaat agcaaaatcc       660
aaattacttt gtgggatgga tttacaaatg ttaatacaaa tgtgagaaaa gagcaaaggt      720
ttattttcct tcgtttgaca attaagtact acgtcgtata attaatagac tcatcaaggt      780
cattgtgtaa atgcacttct ttcacgacct tctcctttat gagattgtta tgaatttac       840
```

```
attatttcct ttatcaacta tatatttatc gttttcatac gcggtggagt tcatctgaat      900
ttctctttct aaggttatat atagagaagg atgttgaatt tttcgtcttc tttttttat      960 taaataaaaa atctatcttc tacatcag                                        988
```

<210> SEQ ID NO 6
<211> LENGTH: 988
<212> TYPE: DNA
<213> ORGANISM: Solanum lycopersicum

<400> SEQUENCE: 6

```
taatattaca ttacattcat cacatattat tcatccaaaa caagaatgag tattgtaatt       60
gatgatgatg aaatcttctc tttacctagc cttgatgaac ttgaatccat cacacatctt      120
ctttatgacg acgattccga ttttttcgaa actctttccc caatgagttt agatgttaca      180
acattattgc ctaatattcc tacctccaat tcaattgaat cccccgtaac accggaggaa      240
acaaaagaac catctgtggc gtgtgaggac gcgccacaag attggaggcg gttcataggg      300
gtgaggcgga ggcagtgggg cacgttttca gccgaaataa gagatccaaa taggagagga      360
gcgaggctgt ggctcggaac ttatgagtcc ccgagggatg cagcattagc ttatgaccaa      420
gccgcttaca agattcgggg aaccaaagtt cggcttaatt ttcctgacct gattggctcg      480
gacgtaccta tgccacctag agtaacggct aggcgtcgta cacgctcacg ctcacgctca      540
cccgagccat aacaacttc gtcctcgtca tcctcatcat cctcgtcctc gtcctcgtcc      600
tcgtcggaaa atggaacgaa gaaaaggaaa atagatttga taaactcaat agcaaaatcc      660
aaattacttt gtgggatgga tttacaaatg ttaatacaaa tgtgagaaaa gagcaaaggt      720
ttatttttct tcgtttgaca attaagtact acgtcgtata attaatagac tcatcaaggt      780
cattgtgtaa atgcacttct ttcacgacct tctcctttat gagattgtta tgaattttac      840
attatttcct ttatcaacta tatatttatc gttttcatac gcggtggagt tcatctgaat      900
ttctctttct aaggttatat atagagaagg atgttgaatt tttcgtcttc tttttttat      960 taaataaaaa atctatcttc tacatcag                                        988
```

<210> SEQ ID NO 7
<211> LENGTH: 341
<212> TYPE: PRT
<213> ORGANISM: Solanum tuberosum

<400> SEQUENCE: 7

```
Met Ala Asp Leu Leu Ser Asn Trp Ser Ser Thr Leu Glu Ala Val Pro
1               5                   10                  15

Pro Ser His Cys Ile Pro Val His Glu Arg Pro Ser Asp Pro Val Glu
            20                  25                  30

Ile Val Asp Asn Ile Pro Val Ile Asp Leu Gly Lys Ala Asn Gly Glu
        35                  40                  45

Glu Arg Ser Val Val Val Lys Glu Leu Leu Lys Ala Phe Glu Glu Tyr
    50                  55                  60

Gly Phe Phe Gln Ile Ile Asn His Gly Val Pro Val Asp Leu Met Asp
65                  70                  75                  80

Glu Ala Met Lys Val Tyr Lys Glu Phe Phe Ser Leu Pro Ala Ala Glu
                85                  90                  95

Lys Ala Glu Tyr Ala Lys Asp Ala Ala Asn Asp Thr Asn Arg Gly Ala
            100                 105                 110

Ala Thr Leu Tyr Ser Ser Ser Ala Lys His Tyr Asp Ser Glu Glu His
        115                 120                 125
```

```
Arg Tyr Trp Arg Asp Val Leu Glu His Ser Cys Asn Leu Asp Gly Lys
            130                 135                 140

Asp Lys Lys Thr Trp Pro Ser Asn Pro Pro Arg Tyr Arg Glu Val Ile
145                 150                 155                 160

Gly Ala Tyr Gly Asp Glu Leu Arg Arg Val Ser Lys Val Ile Leu Gly
                165                 170                 175

Leu Leu Ala Glu Gly Leu Gly Leu Ala Gly Phe Phe Asp Thr Glu
            180                 185                 190

Leu Gly Gln Arg Met Leu Val Asn His Tyr Pro Ala Cys Pro Asp Pro
            195                 200                 205

Ser Leu Thr Leu Gly Val Gly Gly His Cys Asp Pro Asn Leu Ile Thr
210                 215                 220

Ile Ile Gln Gln Glu Val Tyr Gly Leu Gln Ile Leu Lys Asp Asp Lys
225                 230                 235                 240

Trp Ile Gly Val Gln Pro Ile Arg Asn Ala Phe Val Val Asn Ser Gly
                245                 250                 255

Leu Pro Ile Thr Val Val Ser Asn Gly Lys Leu Thr Ser Val Ala His
                260                 265                 270

Arg Val Val Thr Asn Thr Thr His Ser Arg Thr Ser Ile Gly Thr Phe
            275                 280                 285

Ile Cys Pro His Asp Ile Val Glu Pro Ala Lys Ala Leu Val Gly Pro
290                 295                 300

Glu Asn Pro Pro Gln Phe Lys Ser Phe Asn Trp Gly Ile Asp Phe Met
305                 310                 315                 320

Pro His Tyr Leu Ser Lys Lys Ser Val Tyr His Ala Ser Leu Glu Pro
                325                 330                 335

Phe Lys Ile Asp Ala
            340

<210> SEQ ID NO 8
<211> LENGTH: 342
<212> TYPE: PRT
<213> ORGANISM: Solanum lycopersicum

<400> SEQUENCE: 8

Met Ala Asp Leu Leu Ser Asn Trp Ser Ser Thr Leu Glu Ala Val Pro
1               5                   10                  15

Lys Ser His Cys Ile Pro Glu His Glu Arg Pro Ser Asp Pro Val Glu
                20                  25                  30

Ile Gly Asp Ser Ile Pro Val Ile Asp Leu Gly Lys Ala Asn Gly Glu
            35                  40                  45

Glu Arg Ser Val Val Val Lys Asp Leu Leu Lys Ala Phe Glu Glu Tyr
50                  55                  60

Gly Phe Phe Gln Ile Ile Asn His Gly Val Pro Val Asp Leu Met Asp
65                  70                  75                  80

Glu Ala Met Lys Val Tyr Lys Glu Phe Phe Ser Leu Pro Ala Glu Glu
                85                  90                  95

Lys Glu Asn Tyr Ala Lys Asp Ala Ala Asn Thr Asn Arg Gly Ala
                100                 105                 110

Ala Thr Leu Tyr Ser Ser Ser Ala Lys His Tyr Asp Ser Glu Glu His
            115                 120                 125

Arg Tyr Trp Arg Asp Val Leu Glu His Ser Cys Asn Leu Asp Gly Glu
            130                 135                 140

Asp Lys Lys Thr Trp Pro Asp Asn Pro Pro Arg Tyr Arg Glu Val Ile
```

```
              145                 150                 155                 160
Gly Ala Tyr Gly Asp Glu Leu Arg Arg Val Ser Lys Val Ile Leu Gly
                165                 170                 175

Met Leu Ser Glu Gly Leu Gly Leu Glu Ala Gly Phe Phe Asp Lys Glu
                180                 185                 190

Leu Gly Gln Arg Met Leu Val Asn His Tyr Pro Ala Cys Pro Asn Pro
                195                 200                 205

Ser Leu Thr Leu Gly Val Gly Gly His Cys Asp Pro Asn Leu Ile Thr
        210                 215                 220

Ile Ile Gln Gln Glu Val Tyr Gly Leu Gln Ile Leu Lys Asp Asp Lys
225                 230                 235                 240

Trp Ile Gly Val Gln Pro Ile Arg Asn Ala Phe Val Val Asn Ser Gly
                245                 250                 255

Leu Pro Ile Thr Val Tyr Ser Asn Gly Lys Leu Thr Ser Val Ala His
                260                 265                 270

Arg Val Val Thr Asn Thr Thr Glu Ser Arg Thr Ser Ile Gly Thr Phe
                275                 280                 285

Ile Cys Pro His Glu Ile Val Glu Pro Ala Lys Ala Leu Val Gly Pro
        290                 295                 300

Glu Asn Pro Pro Gln Phe Lys Pro Phe His Trp Gly Ile Asp Phe Met
305                 310                 315                 320

Pro His Tyr Leu Ser Lys Lys Ser Val Tyr His Ala Ser Leu Glu Pro
                325                 330                 335

Phe Lys Thr Glu Ala Asn
                340

<210> SEQ ID NO 9
<211> LENGTH: 1619
<212> TYPE: DNA
<213> ORGANISM: Solanum tuberosum

<400> SEQUENCE: 9
ctttgttatg caattttctt ccctataaat ggccctccat agctcaaatg agatatcaga      60
caatttaaag aagtactatt aacatttaga agatttcttt cttttcccagg taaataaatc     120 attttccctc tttccttctt gctctttctt tgtttatttg ttcagatttt tacccttttt     180
gttttggtta gattcattga caatggcgga ccttctttca aactggtcaa gcacattaga     240
agcagttcct ccaagtcatt gcatcccagt gcatgaaaga ccatcggatc cagttgaaat     300
tgtggacaat attccagtca ttgatttggg aaaagctaat ggtgaagaac gaagtgttgt     360
tgttaaagaa cttttgaaag cttttgaaga atatgggttt tttcaggttt attatttata     420
caatagtaca actctgttct ttttttcttttt ttttcttat tgtatttaaa aatgatctga     480
aattgaaatg atgaaataga taatcaatca tggagtaccc gtagatctaa tggatgaagc     540
aatgaaagtg tacaaagaat ttttcagtct gccagcagca gagaaagcag aatatgcaaa     600
ggatgcagct aatgatacaa ataggggtgc agctacactg tacagtagca gcgctaagca     660
ttatgattca gaggagcatc gttactggag agatgtcttg aacatagct gcaatcttga      720 tgggaaagac aaaaaaactt ggcctagtaa ccctccaaga tataggtacc tacctaaact     780
atgcttagca aaattccctc ttgttatttt tcttacctag tatttgcttg tccttcaggg     840
aggttattgg tgcatatgga gatgaattga aagggtgag caaagttatc ttgggtctgt     900
tagctgaagg gctaggtttg gaggcagggt tctttgacac agaacttggg cagagaatgc     960
ttgtgaatca ctatccagca tgcccagatc caagtttaac cttgggagtt ggtggacatt    1020
```

-continued

```
gtgatcctaa tctcataacc attatccaac aagaagtgta tggtcttcaa atattgaagg      1080
atgacaaatg gattggtgtg cagcctatcc gcaatgcatt tgtggtcaat tctggtttac      1140
caattacggt aggtgtaaca ctttctctta attttcatgg tctacaagcg attctcttat      1200
tgctctgttt tttttgtata aatacaggta gttagcaatg aaaagctaac tagtgttgca      1260
catcgtgtgg tgacaaacac aactcattca cgaacctcca ttggtacttt tatttgccca      1320
cacgatattg ttgagcctgc aaaagcactt gttggtccgg agaatcctcc acagttcaaa      1380
tcctttaatt ggggaattga ttttatgcca cattacctca gcaagaaatc agtttaccac      1440
gcatcattgg agcccttcaa aatcgatgct taagcatttg tgtgccagaa ggatcaagtc      1500
tatgctgcta ctttttaattt ccactaaaat aagagcttta atttacaatg tctttctagt     1560
ttgtatccta cctttgttac ctatttcatg aataagaatc tttctttcct attctcttc      1619
```

<210> SEQ ID NO 10
<211> LENGTH: 1292
<212> TYPE: DNA
<213> ORGANISM: Solanum tuberosum

<400> SEQUENCE: 10

```
ctttgttatg caattttctt ccctataaat ggccctccat agctcaaatg agatatcaga       60
caatttaaag aagtactatt aacatttaga agatttcttt cttttcccaga ttcattgaca     120 atggcggacc ttcttccaaa ctggtcaagc acattagaag cagttcctcc aagtcattgc     180
atcccagtgc atgaaagacc atcggatcca gttgaaattg tggacaatat tccagtcatt     240
gatttgggaa aagctaatgg tgaagaacga agtgttgttg ttaaagaact tttgaaagct     300
tttgaagaat atgggttttt tcagataatc aatcatggag tacccgtaga tctaatggat     360
gaagcaatga aagtgtacaa agaattttc agtctgccag cagcagagaa agcagaatat     420
gcaaaggatg cagctaatga tacaaatagg ggtgcagcta cactgtacag tagcagcgct     480
aagcattatg attcagagga gcatcgttac tggagagatg tcttggaaca tagctgcaat     540
cttgatggga aagacaaaaa aacttggcct agtaaccctc caagatatag ggaggttatt     600
ggtgcatatg gagatgaatt gagaagggtg agcaaagtta tcttgggtct gttagctgaa     660
gggctaggtt tggaggcagg gttctttgac acagaacttg ggcagagaat gcttgtgaat     720
cactatccag catgcccaga tccaagttta accttgggag ttggtggaca ttgtgatcct     780
aatctcataa ccattatcca acaagaagtg tatggtcttc aaatattgaa ggatgacaaa     840
tggattggtg tgcagcctat ccgcaatgca tttgtggtca attctggttt accaattacg     900
gtagttagca atggaaagct aactagtgtt gcacatcgtg tggtgacaaa cacaactcat     960
tcacgaacct ccattggtac ttttatttgc ccacacgata ttgttgagcc tgcaaaagca     1020
cttgttggtc cggagaatcc tccacagttc aaatccttta attggggaat tgattttatg     1080
ccacattacc tcagcaagaa atcagtttac cacgcatcat tggagccctt caaaatcgat     1140
gcttaagcat ttgtgtgcca gaaggatcaa gtctatgctg ctacttttaa tttccactaa     1200
aataagagct ttaatttaca atgtctttct agtttgtatc ctacctttgt tacctatttc     1260
atgaataaga atctttcttt cctattctct tc                                    1292
```

<210> SEQ ID NO 11
<211> LENGTH: 1726
<212> TYPE: DNA
<213> ORGANISM: Solanum lycopersicum

<400> SEQUENCE: 11

```
aaaaaatatt tgttttaaa atgtgtaatt tttagtggca tgctctaaaa aaaaataaaa      60
ttatctgagc atcagttttg gttatgcaat ttccttccct ataaatggcc ctccatatct    120
caaatgagat atcaaacaat ttgcagaagt agtagtatta acatttagaa gataaactttg   180
tttcccaggt aaataaatca ataaatcctc cttttctttg tttgtttgtt tatttgttga    240
gatatttatg attttggtt ttggtttaga ttgattgtca atggcggatc ttctctcgaa     300
ctggtcaagc acattagaag cagttcctaa aagtcattgc atcccagagc atgaaagacc    360
atcagatcca gttgaaattg gcgacagtat tccagtcatt gatttgggaa agctaatgg     420
tgaagaacga agtgttgttg ttaaagatct gttgaaagct tttgaagaat atgggttttt    480
tcaggtacgc aactctgttt cttttttttt tgttcccgtt aatgtgaaat tgaaatgatg    540
atatatgaac aaacagataa tcaatcatgg agtacctgta gatctaatgg atgaagcaat    600
gaaagtgtac aaagaatttt tcagtcttcc agctgaagaa aaagaaaatt atgcaaaaga    660
tgcagctaat aataccaata ggggtgcagc tacactgtac agtagcagtg ctaagcatta    720
tgattcagag gagcatcgtt actggagaga tgtgttggaa catagctgca atcttgatgg    780
agaagacaaa aaaacttggc ccgataaccc tccaagatat aggtacctac ctatctaaac    840
tatgtatggt ttagcaatta atttccctct tttcttacac atgtattttg gttgtacttc    900
agggaggtta ttggtgccta tggtgatgaa ttgagaaggg tgagcaaagt tatcttgggt    960
atgttaagtg aagggctagg tttggaggca gggttctttg acaagaaact tgggcagaga   1020
atgcttgtga atcactatcc agcatgtcca aatccaagtt taactttggg agttggtgga   1080
cattgtgatc ctaatctcat aaccattatc aacaagaag tctatggtct tcaaatattg     1140
aaggatgaca aatggattgg tgtgcagcct attcgcaatg catttgtggt taattctggt   1200
ttaccaatta cggtatgtat gtgtgtaggt cttctctaac acccccttt tttcttctct    1260
tataatgttt gctatgcata caggtatata gcaatggaaa gctaactagt gttgcacatc   1320
gtgtggtgac aaacacaact gagtcacgaa cctccattgg tacttttatt tgcccacatg   1380
agattgttga acctgcaaaa gcacttgttg gtcctgagaa tcctccacag ttcaaaccct   1440
tccattgggg aatcgatttt atgccacatt acctcagcaa gaaatcagtg taccacgctt   1500
cattggagcc cttcaaaaca gaagctaatt aagcattaag gatatatcaa atctatgctg   1560
ctgctgctac tacttctttt aatttccact gaaataagag ctttaattca aaatgtcttt   1620
ctagtttgta ttctacttac ttcatgaata agaaacttcc aatcctattc tctactggtt   1680
tcgatctaca tgaatatttt attatttcca ttgcattttc aatcag                  1726
```

<210> SEQ ID NO 12
<211> LENGTH: 1422
<212> TYPE: DNA
<213> ORGANISM: Solanum lycopersicum

<400> SEQUENCE: 12

```
aaaaaatatt tgttttaaa atgtgtaatt tttagtggca tgctctaaaa aaaaataaaa      60
ttatctgagc atcagttttg gttatgcaat ttccttccct ataaatggcc ctccatatct    120
caaatgagat atcaaacaat ttgcagaagt agtagtatta acatttagaa gataaactttg   180
tttcccagat tgattgtcaa tggcggatct tctctcgaac tggtcaagca cattagaagc    240
agttcctaaa agtcattgca tcccagagca tgaaagacca tcagatccag ttgaaattgg   300
cgacagtatt ccagtcattg atttgggaaa agctaatggt gaagaacgaa gtgttgttgt    360
```

```
taaagatctg ttgaaagctt ttgaagaata tgggtttttt cagataatca atcatggagt    420
acctgtagat ctaatggatg aagcaatgaa agtgtacaaa gaattttca gtcttccagc     480
tgaagaaaaa gaaaattatg caaaagatgc agctaataat accaataggg gtgcagctac    540
actgtacagt agcagtgcta agcattatga ttcagaggag catcgttact ggagagatgt    600
gttggaacat agctgcaatc ttgatggaga agacaaaaaa acttggcccg ataaccctcc    660
aagatatagg gaggttattg gtgcctatgg tgatgaattg agaagggtga gcaaagttat    720
cttgggtatg ttaagtgaag ggctaggttt ggaggcaggg ttctttgaca agaacttgg     780
gcagagaatg cttgtgaatc actatccagc atgtccaaat ccaagtttaa ctttgggagt    840
tggtggacat tgtgatccta atctcataac cattatccaa caagaagtct atggtcttca    900
aatattgaag gatgacaaat ggattggtgt gcagcctatt cgcaatgcat ttgtggttaa    960
ttctggttta ccaattacgg tatatagcaa tggaaagcta actagtgttg cacatcgtgt    1020
ggtgacaaac acaactgagt cacgaacctc cattggtact tttatttgcc acatgagat    1080
tgttgaacct gcaaaagcac ttgttggtcc tgagaatcct ccacagttca aaccttcca    1140
ttgggggaatc gatttatgc cacattacct cagcaagaaa tcagtgtacc acgcttcatt    1200
ggagcccttc aaaacagaag ctaattaagc attaaggata tatcaaatct atgctgctgc    1260
tgctactact tcttttaatt tccactgaaa taagagcttt aattcaaaat gtctttctag    1320
tttgtattct acttacttca tgaataagaa acttccaatc ctattctcta ctggtttcga    1380
tctacatgaa tattttatta tttccattgc attttcaatc ag                      1422
```

<210> SEQ ID NO 13
<211> LENGTH: 224
<212> TYPE: PRT
<213> ORGANISM: Solanum lycopersicum

<400> SEQUENCE: 13

```
Met Pro Ser Leu Gly Val Phe Ser Ile Leu Ile Ser Arg Met Ala Cys
1               5                   10                  15

Tyr Ile Ile Val Asn Leu Ser Ser Leu Ile Ala Ile Ser Arg Ser Thr
            20                  25                  30

Pro Gly Pro Val Glu Gly Ser Val Glu His Ser Gln Ile Ile Arg Asn
        35                  40                  45

Gly Ser Thr His Glu Asp Asp Ile Val Ile Asn Pro Thr Leu Leu Ala
    50                  55                  60

Ser Val Gln Ser Phe Val Glu Pro Asn Leu Thr Ala Ala Ala Leu Tyr
65                  70                  75                  80

Arg Ala Thr His Asp Ser His Met Ala Ala Asp Glu Ala Ile Ala Phe
                85                  90                  95

Asn Met Pro Leu Gln Pro Asn Leu Phe Glu Asn Ala Ser Val Glu Pro
            100                 105                 110

Ser Pro Asp Ala Glu His Pro Ser Gln Thr Gln Ser Leu Cys Trp Pro
        115                 120                 125

Asp Lys Arg Asp Thr Ile Glu Ser Glu Val Leu Ser Tyr Gly Arg Asn
    130                 135                 140

Asp Gln Glu Glu Val Lys Phe Asp Gly Glu Ala Val Gly Arg Ser His
145                 150                 155                 160

Ala Tyr Ser Gln Arg Leu Leu Asn Ile Ile Asn Gln Thr Leu Ala Ser
                165                 170                 175

Val Gly Val Asp Pro Ser Leu Ala Asp Val Arg Val Gln Leu Asp Ile
```

|     |     |     | 180 |     |     |     | 185 |     |     |     | 190 |     |     |
| --- | --- | --- | --- | --- | --- | --- | --- | --- | --- | --- | --- | --- | --- |
| Ser | Lys | Lys | Thr | Ser | Ser | Gly | Ala | Thr | Thr | Thr | Arg | Leu | Ser | Ser | Gly |
|     |     |     | 195 |     |     |     |     | 200 |     |     |     |     | 205 |     |

| Glu | Asn | Tyr | Gly | Gly | Ala | Pro | Lys | Arg | Leu | Arg | Thr | Glu | Gly | Ser | Met |
| --- | --- | --- | --- | --- | --- | --- | --- | --- | --- | --- | --- | --- | --- | --- | --- |
|     |     |     | 210 |     |     |     | 215 |     |     |     | 220 |     |     |     |     |

<210> SEQ ID NO 14
<211> LENGTH: 2497
<212> TYPE: DNA
<213> ORGANISM: Solanum lycopersicum

<400> SEQUENCE: 14

```
atgccaagtt tagggggtgtt ttcaatactc atctctagaa tggcttgcta tatcattgtt      60
aatttaagtt ctcttattgc tatttctgct gttgagtaaa aagcatagta gttccttgca     120
tcatttgcac tttcatctgt ttgatgttat gctgtggatt cttttcctaa gtgttgactt     180
tttctctacc tcctatttta ggaaaaagag gcaatagtat tttaagtcca tctcttaagg     240
aatggctaat gttgaaatat aacaaagaac ttccttcttt ggcaacacat ggttggcttc     300
ttgtccttta gctatgtgat tttctgtact tcgattttat tccctcctcc acttcttatt     360
tggcagttta gttgtagcat taaaatagat tcattctaac cagatggctt acttatggaa     420
tcttcaactc tttaataata gtaatggaaa attatgaagt cagtgcacca tgagaaagaa     480
gacattgttt gacccaagag aagtaaactg agctatataa aattggattg agcgctttaa     540
ttactgcaga tattcccctc tgaaaagtac tggatcaaag aaaaaaatgt tctctgatgt     600
tacctatacc tgtatgcccc agttgctgta cagtaaaggt ataattcagt agtcatttcg     660
tatgcttgcc aaatacagaa aaatgcagac gttagctgta tttctagggg aaactcctcg     720
cctacagttc aaacaaaggt tttacatttg cttataattt cctccctcca agcaaagtg     780
accggatttt gggctctttt aggaggagag ttgggcacaa ctttaggatg aagcagtaa     840
tgcttttctg gaagtaaaac taatgctctt ctcttattat tgacagagaa gtactcctgg     900
gcccgtggaa ggctctgttg aacattctca ataatcaga acggctcta ctcatgagga     960
tgatattgtc attaacccaa cattgcttgc aagtgtccag agctttgtag aaccgaactt    1020
gactgctgct gctttatata gagcaacaca cgattctcat atggcagcgg atgaggcaat    1080
tgcctttaac atgccactgc aacctaattt atttgaaaat gcatctgttg aaccatctcc    1140
tgatgctgag caccctttctc agacacaatc attatgttgg ccagataaac gagatacaat    1200
tgagtcggag gttctgagct atggcagaaa tgatcaagaa gaagtgaaat tcgatggtga    1260
agcagttgga agatcacatg catatagtca aaggtaagat gatttatcag gagttcaata    1320
gctatgactt gatgtccttg taaggtggaa attcaaattt atttcttcta tgaccccatg    1380
acttgctaat ttctgtaatg atgccaaact tgtattacac ctacgaagta ggcatgtgat    1440
acagtatcac tttaagtccc ttggacccag tgggcctagt ggcagtcacg gtcttagaag    1500
aattatccta tggttgtcaa gtgcatgaaa tagatttaga ctagttaatg tttctcgtgg    1560
ttattagctg gttggctaga atgcaaagtg tagccttttt aagccccttc cagcatgagt    1620
tttttttgtaa aacctgctgt aacttgtggg tttgcatttt ttttgtgaat aaaattgcca    1680
gttcaacaaa gatttcagtg gcttgaagga agtcatttta tatgacccgg catggtttac    1740
ctgttgaagg ttaataacaa gcggaaccct ggatttcgag atttgagtct cactttagga    1800
ttttttcagac ttcccattaa cacaaagtca tgtataacac acatgttcgt atcattctta    1860
cttgtgcagt tgtcctctgt acctttaggc acattttaat ctgaactcgg ttgatctgaa    1920
```

| | |
|---|---:|
| attatattat gatgccagta aactactgat tttggattct atttatgtga catattgggt | 1980 |
| cttggtattg agcaggttgc ttaatatcat aaaccagact ctagcatctg tgggagtgga | 2040 |
| tccgtcactg gccgatgtta gagtacagct tgatatcagc aaaaaaacaa gcagtggagc | 2100 |
| cacaactaca agattaagca gtggagagaa ctatggtggt gctcctaaaa ggcttaggac | 2160 |
| agaaggtagt atgtgattat taatctagca tggctccact cctaattttt ctgcatcttg | 2220 |
| tcatcgtttt gatggggaga tagttgaagt ggttggtctc cgtggatgag gtggtgcaca | 2280 |
| aacagcttat ggttgtccag ttaggtttcc atttaaatat gagaagctgc attgtcattc | 2340 |
| ttaagggtat ttagttttga attgagataa gtcgactttg atagttctgt cagtgtgata | 2400 |
| tggttatgcc tatcgatttg ccatggatct gttttcgtag ttgatattta aacagggaaa | 2460 |
| tttgaagttg tttcaaatgt tagcatgaag aatttta | 2497 |

<210> SEQ ID NO 15
<211> LENGTH: 996
<212> TYPE: DNA
<213> ORGANISM: Solanum lycopersicum

<400> SEQUENCE: 15

| | |
|---|---:|
| atgccaagtt tagggtgtt ttcaatactc atctctagaa tggcttgcta tatcattgtt | 60 |
| aatttaagtt ctcttattgc tatttctaga agtactcctg ggcccgtgga aggctctgtt | 120 |
| gaacattctc aaataatcag aaacggctct actcatgagg atgatattgt cattaaccca | 180 |
| acattgcttg caagtgtcca gagctttgta gaaccgaact tgactgctgc tgctttatat | 240 |
| agagcaacac acgattctca tatggcagcg gatgaggcaa ttgccttaa catgccactg | 300 |
| caacctaatt tatttgaaaa tgcatctgtt gaaccatctc ctgatgctga gcacccttct | 360 |
| cagacacaat cattatgttg gccagataaa cgagatacaa ttgagtcgga ggttctgagc | 420 |
| tatggcagaa atgatcaaga agaagtgaaa ttcgatggtg aagcagttgg aagatcacat | 480 |
| gcatatagtc aaaggttgct taatatcata accagactc tagcatctgt gggagtggat | 540 |
| ccgtcactgg ccgatgttag agtacagctt gatatcagca aaaaacaag cagtggagcc | 600 |
| acaactacaa gattaagcag tggagagaac tatggtggtg ctcctaaaag gcttaggaca | 660 |
| gaaggtagta tgtgattatt aatctagcat ggctccactc taattttttc tgcatcttgt | 720 |
| catcgttttg atggggagat agttgaagtg gttggtctcc gtggatgagg tggtgcacaa | 780 |
| acagcttatg gttgtccagt taggtttcca tttaaatatg agaagctgca ttgtcattct | 840 |
| taagggtatt tagttttgaa ttgagataag tcgactttga tagttctgtc agtgtgatat | 900 |
| ggttatgcct atcgatttgc catggatctg ttttcgtagt tgatatttaa acagggaaat | 960 |
| ttgaagttgt ttcaaatgtt agcatgaaga atttta | 996 |

<210> SEQ ID NO 16
<211> LENGTH: 3899
<212> TYPE: DNA
<213> ORGANISM: Solanum tuberosum

<400> SEQUENCE: 16

| | |
|---|---:|
| tttttttaca aaaactttt tatccaacac caccgagtag cttgactcgc cccttaaaa | 60 |
| aattattta aaaataaaat attttttttt tcttatccca ctcctctccc ctaaaaaaaa | 120 |
| aataagttca aaagaattct ttttgggggt gagtgggtag tgaggtggga ggctaggggg | 180 |
| ggtactgggt agaggatggg gtgggtgata agaaaaaata aatcttcaaa aagaaaaaaa | 240 |

```
agttctttta tcttcttaaa ttgctaaatt cttaacattt aattatttaa atgttcttta      300
aaaaaatttc tattacatat atttatgtgt acacaccatt accattttca aaaaaaataa      360
atatttatgt atacacaacg tcaacagaaa attctacata tatgcccatg tggcataaga      420
agggtgtttt taaattcact taatcaagta aaggggtgtt tttaaggctg ttaatagttg      480
gaggattaaa gtaataattc atgccaagtt tagggggtgtt ttcaatactt atctctagaa     540
tggtctccct attccttgct atattgttgt taatttaagt tctcttattg ctattctgct      600
atgttgagta aaaagcacag tagttccttg catcatttgc acttctcatc tgtttgatgg      660
tatgctgtgg attcttttt  caagtggtgt tggacttgtt tgcttggatg ataatctttc      720
atgtttactc cttattgttg aactttttt  ctacctccct attaaggaaa aaaaggcaat      780
agtattttca gtccatctct taaggaatgg ctaatgttga agatataatg aagaacttcc      840
ttctttggca acacatggtt ggcttcttgt cctctagcta tgtgatattt tatacttcga      900
tttttattcc ctccttcact tcttgtttgg cagtttagtt atagcattaa aatagattca      960
ttataaccag atggcttact gaaggaatct tctactcttt aataatagtg ttaaattagg     1020
tcttaggcct aactcacacc ccaaaagcta gctcaaaggg aggaggattg ttcaagcctt     1080
gtaaggagtc cacccatctc aaagggagga ggcttgttca agccttataa ggagtccacc     1140
catctcatta accaccgatg tgggactttt gtcattcttt aacaaatagt attagaaaat     1200
tatgaagtca gtgcaccatg agaaagaaga cattgtttga cccaagagaa gtaaactgag     1260
ctatataaaa tcggattgag actttaattt actgcagata ttaccctctg aaaagtactg     1320
gattaaagaa aaaaatgttc tctgatgtta ccctatacct gtgtgcccca gttactgtac     1380
agtaaagtca taattcagta gttattttgg atgctttcca aatacagaaa atgcagacg      1440 ttagctgttt ttgtagggga aactcctcgc ctatggttca aacaaggct  ttacatttgt     1500 ttttaatttt ctccctccaa agcaaagtta ccggatttca ggctgtttta ggaggagagt     1560
tgggcacaac tttaggatgg aagcagtagt gtttttctga agtaaaaact aatgctcttc     1620
tcttattatt gacagagaag cactcctggg cccgtggaag gctctgttga acattctcaa     1680
ataatcagaa acggctctac tcatgaggat gatattgtca ttaacgcaac attgctttcg     1740
agtgcccaga gctttgtaga accgaacttg actgctgctg ctttatatag agcaacacac     1800
gattctcata tggcagcgga tgaagcaatt gcctttaaca tgccactgca acctaattta     1860
tttgaaaatg catctgttga accatctcct gatgctgagc acccttccca gccacaatca     1920
ttatgttggc caggtaaacg agatacaatt gagtcggagg ttctgagcta tggcagaaat     1980
gatcaggaag aagtgaaatg cgatggtgaa gcagttgcaa gatcacatgc gtatactcaa     2040
aggtaagatg atttatcacg agttcaatag ctatgacttg atgtcctggt aaggtggaaa     2100
ttcaaattta tttcttctac gcccccatga cttgctaatt tctgtaatga tgccaaactt     2160 gtattcacacc tacgaaatag gcatgtgata cagaatcact ttaagtacct tggacccagt    2220
gggcctagtg gcagtcaagg tcttagaaga attacctgta gtgttccaat ttcttattgt     2280
cctgtgattg ccaagtgcat gaaatagatt cagactaggt aatgtttctc gtggttatta     2340
gctggttggt tgaaatgcag attgtagcct ttctgagccc cttccagtat agttttttt      2400 gtaaaacctg ctgcaacttg tgggtttgca ttttttgtg aataaaattg ccaattcaaa      2460
aaagatttca gtggcttgaa ggaagtcatt tatatgaccc ggcattgttt acccgagcaa     2520
tcaaatatca atcaggtttc cctgcatggc ttccccaac ttttctacct gacccatcaa      2580
atggaaatct aagttgaagg ttaataacaa gcggatctct ggatttcgag gtttgagtct     2640
```

-continued

```
cacttaagga ttttccagac ttcccattaa acgaagaaa tgtataacaa acatgtacat    2700
atcattctga cttgagcagt tgtcctctga acctttaggc acattctgat ctgatttcag   2760
ttgatctgaa attatattat gatgctagta tactactgat tttggattct atttatgtga   2820
catattgagt cttggtattg agcaggttgc ttaatatcat aaaccagaca ctagcatctg   2880
tgggagtgga tccttcactg gccgatgtta gagtacagct tgatatcagc aaaaaaccaa   2940
gcagtggagc cacaactaca acattaagca gtgaagagaa ctatgatggt gctcctaaaa   3000
ggcttaggac agaaggtagt atgtgattgt caatctagca tggttccact cctaattttt   3060
ctgcatcttg tcattgtttc gatggggaga tacttgaagt ggttggtctc tgtggatgag   3120
gtggtgcaca aacagcttat ggttgtccag ttaggtttcc atttaaatat gagaagctgc   3180
attgtcattc ttaagggtat ttagatagtc gactttggaa attctgtcag tgtgatgtgg   3240
ttatgcctat cgatttgaga tgcctccatg gatctggttt catagttgat atttaaacag   3300
ggaaatttga agttgtttca aatgtcagca tgaagaattt tatgtacatt accaaatctt   3360
ttccttttca gtattttgtg attagttcac ttaaacagga tgctggcttt tcaattgtgt   3420
tttcagaaat aaaagtcagc acttgtatca ttgtgaaaaa ctgaaaattt tggtctttaa   3480
gtcgaatcaa caacataatg caagtattta ctgataacgg cgtttggtca gatgaatacg   3540
gcagtttcac aatgattgca tatgaatatg ctcatgttag tccatggtat atattgtaat   3600
tttatcctaa agatatcgta atgagaagtt agatgagttt gatgcgatga actgatgaag   3660
cattggtaat gggttattgg tttagcagtt ttgctaattc tcatttatat ttgggatatc   3720
cgttgtcaaa tgtttgaggt tcttttctta acacattaat cgaattaata aattaaactc   3780
tcggctattc tactaggtgc caatatttgc ttttgagcaa gatgcaatat gtcgttcatt   3840
tggtttgtca ccttgtttct aagtgagttt taatctataa cagaatgttt gttggtaaa   3899
```

<210> SEQ ID NO 17
<211> LENGTH: 990
<212> TYPE: DNA
<213> ORGANISM: Solanum tuberosum

<400> SEQUENCE: 17

```
atgccaagtt tagggtgtt ttcaatactt atctctagaa tggcttgcta tattgttgtt     60
aatttaagtt ctcttattgc tattagaagc actcctgggc ccgtggaagg ctctgttgaa   120
cattctcaaa taatcagaaa cggctctact catgaggatg atattgtcat taacgcaaca   180
ttgctttcga gtgcccagag ctttgtagaa ccgaacttga ctgctgctgc tttatataga   240
gcaacacacg attctcatat ggcagcggat gaagcaattg cctttaacat gccactgcaa   300
cctaatttat ttgaaaatgc atctgttgaa ccatctcctg atgctgagca cccttcccag   360
ccacaatcat tatgttggcc aggtaaacga gatacaattg agtcggaggt tctgagctat   420
ggcagaaatg atcaggaaga agtgaaatgc gatggtgaag cagttgcaag atcacatgcg   480
tatactcaaa ggtaggttgc ttaatatcat aaaccagaca ctagcatctg tgggagtgga   540
tccttcactg gccgatgtta gagtacagct tgatatcagc aaaaaaccaa gcagtggagc   600
cacaactaca acattaagca gtgaagagaa ctatgatggt gctcctaaaa ggcttaggac   660
agaaggtagt atgtgattgt caatctagca tggttccact cctaattttt ctgcatcttg   720
tcattgtttc gatggggaga tacttgaagt ggttggtctc tgtggatgag gtggtgcaca   780
aacagcttat ggttgtccag ttaggtttcc atttaaatat gagaagctgc attgtcattc   840
```

```
ttaagggtat ttagagtcga cttttggaaat tctgtcagtg tgatgtggtt atgcctatcg    900
atttgagatg cctccatgga tctggtttca tagttgatat ttaaacaggg aaatttgaag    960
ttgtttcaaa tgtcagcatg aagaatttta                                     990
```

<210> SEQ ID NO 18
<211> LENGTH: 220
<212> TYPE: DNA
<213> ORGANISM: Artificial Sequence
<220> FEATURE:
<223> OTHER INFORMATION: Synthetic polynucleotide

<400> SEQUENCE: 18

```
atgagtattg taattgatga tgatgaaatc ttctctttac ctagccttga tgaacttgaa     60
tccatcacac atcttcttta tgacgacgat tccgattttt tcgaaactct ttccccaatg    120
agtttagatg ttacaacatt attgcctaat attcctacct ccaattcaat tgaatccccc    180
gtaacaccgg aggaaacaaa agaaccatct gtggcgtgtg                          220
```

<210> SEQ ID NO 19
<211> LENGTH: 251
<212> TYPE: DNA
<213> ORGANISM: Artificial Sequence
<220> FEATURE:
<223> OTHER INFORMATION: Synthetic polynucleotide

<400> SEQUENCE: 19

```
cggatcttct ctcgaactgg tcaagcacat tagaagcagt tcctaaaagt cattgcatcc     60
cagagcatga aagaccatca gatccagttg aaattggcga cagtattcca gtcattgatt    120
tgggaaaagc taatggtgaa gaacgaagtg ttgttgttaa agatctgttg aaagcttttg    180
aagaatatgg gttttttcag ataatcaatc atggagtacc tgtagatcta atggatgaag    240
caatgaaagt g                                                         251
```

<210> SEQ ID NO 20
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 20

```
aaaaagaatt ccggatcttc tctcgaactg gtcaa                                35
```

<210> SEQ ID NO 21
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 21

```
aaaaagaatt ccactttcat tgcttcatcc attagatct                            39
```

<210> SEQ ID NO 22
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 22

```
aaaaagaatt ccttagctta tggccacatc acaccttt                             37
```

<210> SEQ ID NO 23
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 23
aaaaagaatt cactcaagat ttggtgaagc tgtggtt                                37

<210> SEQ ID NO 24
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 24
aaaaaggcgc gccaatcata gagaagaaag aagacg                                 36

<210> SEQ ID NO 25
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 25
aaaaagcggc cgcactcctg caggaattgt catttctc                               38

<210> SEQ ID NO 26
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 26
aaaaagcggc cgcatgagta ttgtaattga tgatgatgaa atc                         43

<210> SEQ ID NO 27
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 27
aaaaggcgcg cccacacgcc acagatggtt ctt                                    33

<210> SEQ ID NO 28
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 28
ggggacaagt ttgtacaaaa aagcaggcta tgagtattgt aattgatgat gatgaaatc        59

<210> SEQ ID NO 29
<211> LENGTH: 54
<212> TYPE: DNA
<213> ORGANISM: Artificial Sequence
<220> FEATURE:

```
<223> OTHER INFORMATION: Synthetic Polynucleotide

<400> SEQUENCE: 29
ggggaccact ttgtacaaga aagctgggtt catactacct tctgtcctaa gcct          54

<210> SEQ ID NO 30
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 30
ggggacaagt ttgtacaaaa aagcaggcta tgaatattgc aattgatgat gatga         55

<210> SEQ ID NO 31
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 31
ggggaccact ttgtacaaga aagctgggtt catttgtatc aacatttgta aattcacac     59
```